(12) United States Patent (10) Patent No.: US 8,349,619 B2
Rossner et al. (45) Date of Patent: Jan. 8, 2013

(54) METHOD FOR DETECTING AND ANALYZING PROTEIN INTERACTIONS IN-VIVO

(75) Inventors: Moritz Rossner, Goettingen (DE); Rico Laage, Schriesheim (DE); Klaus-Armin Nave, Göttingen (DE); Sylvia Gruenewald, Heidelberg (DE)

(73) Assignee: Sygnis Bioscience GmbH & Co. KG, Heidelberg (DE)

( * ) Notice: Subject to any disclaimer, the term of this patent is extended or adjusted under 35 U.S.C. 154(b) by 418 days.

(21) Appl. No.: 12/453,216

(22) Filed: May 1, 2009

(65) Prior Publication Data

US 2009/0298089 A1 Dec. 3, 2009

Related U.S. Application Data

(63) Continuation of application No. 10/507,506, filed as application No. PCT/EP03/02611 on Mar. 13, 2003, now Pat. No. 7,585,635.

(30) Foreign Application Priority Data

Mar. 13, 2002 (DE) .................................. 102 11 063

(51) Int. Cl.
G01N 33/566 (2006.01)
C40B 30/04 (2006.01)
(52) U.S. Cl. ........................................... 436/501; 506/9
(58) Field of Classification Search .................... None
See application file for complete search history.

(56) References Cited

U.S. PATENT DOCUMENTS 6,294,330 B1 9/2001 Michnick et al.
6,303,327 B1 10/2001 Von Melchner et al.

FOREIGN PATENT DOCUMENTS

WO WO 95/29195 11/1995
WO WO 01/94617 A2 12/2001

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Michnick et al, Detection of protein-protein interactions by protein fragment complementation strategies. Methods Enzymol. 2000;328:208-30.*
Ghelis et al, The folding of pancreatic elastase: independent domain refolding and inter-domain interaction. Biochem Biophys Res Commun. Sep. 14, 1978;84(1):31-6.*
Carmel et al, Use of substrates with fluorescent donor and acceptor chromophores for the kinetic assay of hydrolases. FEBS Lett. Feb. 15, 1973;30(1):11-14.*

Kim et al, In vivo determination of substrate specificity of hepatitis C virus NS3 protease: genetic assay for site-specific proteolysis. Anal Biochem. Aug. 15, 2000;284(1):42-8.*
Stevens Design of high-throughput methods of protein production for structural biology. Structure. Sep. 15, 2000;8(9):R177-85. Review.*
Sawyer et al, The atomic structure of crystalline porcine pancreatic elastase at 2.5 A resolution: comparisons with the structure of alpha-chymotrypsin. J Mol Biol. Jan. 15, 1978;118(2):137-208.*
Bazan et al, Viral cysteine proteases are homologous to the trypsin-like family of serine proteases: structural and functional implications. Proc Natl Acad Sci U S A. Nov. 1988;85(21):7872-6.*
Rossner et al, (Applicants) Communication of Sep. 14, 2012.*
Whisstock et al., Prediction of Protein Function from Protein Sequence and Structure, Q. Rev. Biophys. Aug. 2003, 36(3): pp. 306-340.
Michnick et al., Detection of Protein-Protein Interactions by Protein Fragment Complementation Strategies, Methods Enzymol. 2000, 328, pp. 208-230.
Ghelis et al., The Folding of Pancreatic Elastase, Independent Domain Refolding and Inter-Domain Interaction., Biochem biophys Res. Commun., Sep. 14, 1978, 84(1), pp. 31-36.
Carmel et al., Use of substrates with fluorescent donor and acceptor chromophores for the kinetic assay of hydrolases, FEBS Lett. Feb. 15, 1973, 30(1), pp. 11-14.
Stevens Design of High-Throughput Methods of Protein Production for Structural Biology, Structure, Sep. 15, 2000, 8(9): R177-85.
Sawyer et al., The Atomic Structure of Crystalline Porcine Pancreatic Elastase at 2.5 A Resolution: Comparisons with the Structure of Alpha-Chymotrypsin, J. Mol. Biol. Jan. 15, 1978, 118(2), pp. 137-208.
Bazan et al., Viral Cystein Proteases are Homologous to the trypsin-like family of serine proteases, structural and functional implicants, Proc. Natl. Acad. Sci. USA, Nov. 1988, 85(21), pp. 7872-7876.
Mitra et al., Fluorescence resonance energy transfer between blue-emitting and red-shifted excitation derivatives of the green fluorescent protein, Gene, 1996, 173 (1 Spec No), 13-7.
Fields et al., A novel genetic system to detect protein-protein interactions, Nature, Jul. 20, 1989, 340(6230), 245-6.
Allison et al., The nucleotide sequence of the coding region of tobacco etch virus genomic RNA, evidence for the synthesis of a single polyprotein, Virology, Oct. 15, 1986 154(1), pp. 9-20.
GenBank Accession No. AAA47909 gi: 335200 Aug. 3, 1993.
Mattheakis et al., "expression of Cre recombinase as a reporter of signal transduction in mammalian cells," Chemistry and Biology (London), vol. 6, No. 11, Nov. 1999, pp. 835-844, XP002265769, ISSN: 1074-5521.
Dunnwald et al., "Detection of Transient In Vivo Interactions Between Substrate and Transporter During Protein Translocation Into the Endoplasmic Reticulum," Molecular Biology of the Cell (Bethesda, MD, US), vol. 10, No. 2, Feb. 1999, pp. 329-344, XP008006622, ISSN: 1059-1524.
Vidal et al., "Reverse Two-Hybrid and One-Hybrid Systems to Detect Dissociation of Protein-Protein and DNA-Protein Interactions," Proceedings of the National Academy of Sciences of USA, National Academy of Science (Washington, US), vol. 93, Sep. 1, 1996, pp. 10315-10320, XP000749719, ISSN: 0027-8424.
Ashman et al., "Cell Signalling—The Proteomics of it All," pp. 1-6 (2001).

(Continued)

Primary Examiner — Sheridan Swope
(74) Attorney, Agent, or Firm — Foley & Lardner LLP

(57) ABSTRACT

The invention relates to various methods of detecting and analyzing protein interactions in a cell, which methods involve the appearance of a specific protein interaction being converted to a permanent detection signal by means of providing, in a manner dependent on said protein interaction, a recombinase activity or protease activity.

6 Claims, 25 Drawing Sheets

OTHER PUBLICATIONS

Ehrhard et al., "Use of G-Protein Fusions to Monitor Integral Membrane Protein-Protein Interactions in Yeast," *Nature Biotechnology*, pp. 1075-1079 (2000).

Eyckerman et al., "Design and Application of a Cytokine-Receptor-Based Interaction Trap," *Nature Cell Biology*, vol. 3, pp. 1114-1119 (2001).

Fearon et al., "Karyoplasmic Interaction Selection Strategy: A General Strategy to Detect Protein-Protein Interactions in Mammalian Cells," *Proc. Natl. Acad. Sci. USA*, vol. 89, pp. 7958-7962 (1992).

Gavin et al., "Functional Organization of the Yeast Proteome by Systematic Analysis of Protein Complexes," *Nature*, vol. 415, pp. 141-147 (2002).

Haj et al., "Imaging Sites of Receptor Dephosphorylation by PTP1B on the Surface of the Endoplasmic Reticulum," *Science*, vol. 295, pp. 1708-1711 (2002).

Hazzalin et al., Mapk-Regulated Transcription: A Continuously Variable Gene Switch?, *Nature*, vol. 3, pp. 30-40 (2002).

Hubsman et al., "A Novel Approach for the Identification of Protein-Protein Interaction with Integral Membrane Proteins," *Nucleic Acids Research*, vol. 29, No. 4, pp. 1-6 (2001).

Hunter, "Signaling—2000 and Beyond," *Cell*, vol. 100, pp. 113-127 (2000).

Husi et al., "Proteomic Analysis of NMDA Receptor-Adhesion Protein Signaling Complexes," *Nature Neuroscience*, vol. 3, No. 7, pp. 661-669 (2000).

Huttner et al., "Lipids, Lipid Modification and Lipid-Protein Interaction in Membrane Budding and Fission-Insights from the roles of Endophilin A1 and Synaptophysin in Synaptic Vesicle and Endocytosis," pp. 543-551 (2000).

Johnsson et al., "Split Ubiquitin as a Sensor of Protein Interactions in Vivo," *Proc. Natl. Acad. Sci. USA*, vol. 91, pp. 10340-10344 (1994).

Karimova et al., "A bacterial Two-Hybrid System based on a Reconstituted Signal Transduction Pathway," *Proc. Natl. Acad. Sci. USA*, vol. 95, pp. 5752-5756 (1998).

Luban et al., "The Yeast Two-Hybrid System for Studying Protein-Protein Interactions," *Current Opinion in Biotechnology*, pp. 59-64 (1995).

Maroun et al., "A Novel in Vivo Assay for the Analysis of Protein-Protein Interaction," *Nucleic Acids Research*, vol. 27, No. 13, pp. 1-5 (1999).

Marshall, "Specificity of Receptor Tyrosine Kinase Signaling: Transient Versus Sustained Extracellular Signal-Regulated Kinase Activation," *Cell*, vol. 80, pp. 179-185 (1995).

Migaud et al., "Enhanced Long-Term Potentiation and Impaired Learning in Mice with Mutant Postsynaptic Density-95 Protein," *Nature*, vol. 396, pp. 433-439 (1998).

Mohler et al., "Gene Expression and Cell Fusion Analyzed by *lacZ* Complementation in Mammalian Cells," *Proc. Natl. Acad. Sci. USA*, vol. 93, pp. 12423-12427 (1996).

Pawson et al., "Signaling Through Scaffold, Anchoring, and Adaptor Proteins," *Science*, vol. 278, pp. 2075-2080 (1997).

Pelletier et al., "Oligomerization Domain-Directed Reassembly of Active Dihydrofolate Reductase from Rationally Designed Fragments," *Proc. Natl. Acad. Sci.*, vol. 95, pp. 12141-12146 (1998).

Rigaut et al., "A Generic Protein Purification Method for Protein Complex Characterization and Proteome Exploration," *Nature Biotechnology*, vol. 17, pp. 1030-1032 (1999).

Rojo-Niersbach et al., "A New Method for the Selection of Protein Interactions in Mammalian Cells," *Biochem J.*, vol. 348, pp. 585-590 (2000).

Rossi et al., "Monitoring Protein-Protein Interactions in Intact Eukaryotic Cells by β-Galactosidase Complementation," *Proc. Natl. Acad. Sci. USA*, vol. 94, pp. 8405-8410 (1997).

Shioda et al., "A Green Fluorescent Protein-Reporter Mammalian Two-Hybrid System with Extrachromosomal Maintenance of a Prey Expression Plasmid: Application to Interaction Screening," *PNAS*, vol. 97, No. 10, pp. 5220-5224 (2000).

Siegel et al., "Measurement of Molecular Interactions in Living Cells by Fluorescence Resonance Energy Transfer between Variants of the Green Fluorescent Protein," pp. 1-6 (2000).

Simons et al., "Functional Rafts in Cell Membranes," *Nature*, vol. 387, pp. 569-572 (1997).

Ullmann et al., "Identification by in Vitro Complementation and Purification, of a Peptide Fraction of *Escherichia coli* Beta-Galactosidase," J. Mol. Biol. vol. 12, No. 3, pp. 918-923 (1965). [Non-English].

Xu et al., "A Bioluminescence Resonance Energy Transfer (BRET) System: Application to Interacting Circadian Clock Proteins," *Proc. Natl. Acad. Sci. USA*, vol. 96, pp. 151-156 (1999).

Yasukawa et al., "Negative Regulation of Cytokine Signaling Pathways," *Annu. Rev. Immunol.*, pp. 143-164 (2000).

Ehrmann et al., "TnTIN and TnTAP: Mini-transposons for site-specific proteolysis in vivo," *Proc. Natl. Acad. Sci.*, vol. 94, pp. 13111-13115 (1997).

\* cited by examiner

TtevEV

EYtevFP

METHOD FOR DETECTING AND ANALYZING PROTEIN INTERACTIONS IN-VIVO

CROSS-REFERENCE TO RELATED APPLICATIONS

This application is a continuation of U.S. patent application Ser. No. 10/507,506, filed on Dec. 13, 2004, now U.S. Pat. No. 7,585,635 which is the National Phase of International Patent Application No. PCT/EP03/02611, filed Mar. 13, 2003, and published as WO 03/076932 on Sep. 18, 2003, which claims priority from German Patent Application No. 10211063.8, filed on Mar. 13, 2002. The contents of these applications are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 23, 2012, is named 85449216.txt and is 756 bytes in size.

FIELD OF THE INVENTION

The invention relates to various methods of detecting and analyzing protein interactions in a cell, which methods involve the appearance of a specific protein interaction being converted to a permanent detection signal by means of providing, in a manner dependent on said protein interaction, a recombinase activity or protease activity. The detection signal is amplified here, compared to reporter gene activation by way of classical transcriptional activation of reporter genes.

The invention furthermore relates to cells selected from the group consisting of bacteria and yeast cells and of cells of higher eukaryotic cell lines from the group consisting of rodents and Homo sapiens, which cells have been transfected, either stably or transiently, with at least one expression vector, comprising at least one construct for expressing the components indispensible for carrying out the method of the invention.

The invention furthermore relates to a kit for carrying out the abovementioned methods.

The method of the invention in particular makes possible detection of the dynamics of specific protein interactions. Both the coming into being and the induced dissociation of interaction partners are detectable. Said interaction partners may be in direct contact or may be part of a protein complex. The method is particularly suitable for detecting transient interactions, very weak interactions or those interactions induced by a cellular stimulus or a substance.

BACKGROUND OF THE INVENTION

Virtually all biological processes in living organisms are controlled by the function of specifically interacting proteins. Specific analysis of protein interactions makes it possible to isolate unknown proteins and to assign them to functional groups and also to elucidate the molecular mechanism of action of known proteins. Cellular signal transduction which comprises the transfer of extracellular signals to specific intracellular alterations is the key mechanism for controlling a cell during development and in the response to environmental changes. The transfer of these signals is controlled by strictly regulated cascades of specifically interacting proteins. In addition, virtually all important cellular functions which are usually coupled to signal transduction are carried out by controlled protein interactions (Pawson and Scott 1997). These include, inter alia, control of the cell cycle, protein synthesis and protein degradation, prevention or induction of apoptosis, transport processes, detection and induction of stimuli, gene expression, mRNA processing, DNA synthesis and DNA repair and the entire energy metabolism. All these processes are very dynamic, i.e. they are subject to alterations which are embedded in the overall state of the cell. This is reflected, at the protein level, by the regulated alteration of the composition of the function-performing complexes (Ashman, Moran et al. 2001).

Proteins and their interactions are subject to great and dynamic alterations in the cell which are frequently brought about by signal transduction cascades. Their function or the composition of protein complexes may also change due to allosteric effects or a change of intracellular location. The regulation of the function of proteins is particularly dependent on activation by enzymes of the signal transduction cascades which catalyze protein modifications on specific target proteins. Post-translational modifications often have a dramatic influence on the activity of a multiplicity of proteins. Regulated protein phosphorylation, protein acetylation, protein methylation, protein sulfation, protein acylation, protein prenylation, protein ribosylation, protein glycosylation, protein ubiquitination or proteolytic activation and inactivation are known modifications some of whose effects and regulatory mechanisms are only little understood. Modification-dependent protein interactions have been described for a multiplicity of transduction pathways in different cellular adaptation events (Hunter 2000).

The activation or deactivation of particular signal transduction cascades must be exactly controlled in the cell, both by way of time and its form. A multiplicity of pathological processes in cells is caused by interference in the control of signal transduction and may lead to metabolic disorders, cancerogenesis, immunological disorders or neurological deficits. Pathological processes of this kind may be caused in particular by specific mutations in the genes coding for proteins having an important function in neuronal signal transduction. Thus, for example, particular mutations in the genes of NMDA receptor subunits alter the composition and signal properties of the NMDA receptor protein complex (Migaud, Charlesworth et al. 1998). Molecular mechanisms responsible for the precise time control of cellular events and often controlled by feedback mechanisms are only beginning to be understood (Marshall 1995). Time-limited protein-protein interactions, controlled, for example, by reversible post-translational modifications exert a key function here (Yasukawa, Sasaki et al. 2000) (Hazzalin and Mahadevan 2002).

Currently there is a lack of suitable methods for identifying and analyzing regulated, time-limited or modification-dependent protein interactions.

A multiplicity of methods of characterizing protein-protein interactions have been described.

Biochemical methods of protein purification, coupled to mass-spectrometric analytical methods, enable protein complexes to be characterized (Ashman, Moran et al. 2001). Thus it was possible, for example, to isolate, with the aid of a tandem affinity purification (TAP) (Rigaut, Shevchenko et al. 1999), denaturing one-dimensional gel electrophoresis and tryptic digestion of single bands in combination with mass-spectrometric analysis, to isolate a multiplicity of protein complexes from yeast and to determine the components thereof (Gavin, Bosche et al. 2002). Using an optimized immunoprecipitation protocol, mass spectrometry and the Western blot technique, a multiplicity of the components of the neuronal NMDA receptor signal processing complex was characterized (Husi, Ward et al. 2000). These biochemical-biophysical methods seem particularly suitable for the analysis of stable and static protein complexes, but have a few experimental disadvantages and disadvantages in principle. Thus, all biochemical methods are experimentally very expensive and require a very large amount of biological starting material. Moreover, already optimized purification methods (e.g. the TAP method) require the corresponding fusion proteins to be transgenically and stably expressed in the organisms of choice. In the analysis of complex tissues, weakly expressed or cell type-specifically expressed proteins may readily be below the limit of detection. A fundamental disadvantage of all biochemical methods arises from the necessity of cell disruption or of the solubilization of large membrane complexes. Weak or transient interactions may readily be lost during the course of the biochemical workup which usually requires a plurality of steps (Ashman, Moran et al. 2001). Analyses of the interactions of proteins with extreme physicochemical properties, such as, for example, membrane proteins or proteins having a high total charge, in each case need an optimized protocol or, in individual cases, are not possible.

Previous mass-spectrometric methods have only limited suitability for characterization of post-translationally modified proteins, since modifications such as specific phosphate radicals may readily be lost during fragmentation (Ashman, Moran et al. 2001). The composition and functional activity of protein complexes are subject to constant dynamics and are controlled by a multiplicity of regulatory mechanisms. Moreover, it became clear recently that specific physicochemical properties or specific environments, such as specific membrane topologies and membrane compositions for example, strongly influence protein-protein interactions. Thus, for example, the lipid composition of the different intracellular membrane systems plays a large part in the assembly of protein complexes (Huttner and Schmidt 2000). Owing to their particular molecular composition, "lipid rafts", subdomains in the cell membrane, allow completely different interactions than neighboring regions in the lipid bilayer (Simons and Ikonen 1997). Biochemical methods have only limited suitability for detailed analysis of the specific interactions or interaction domains of proteins within a complex or for analysis of possible transient interactions of associated proteins, due to the relatively high experimental costs.

Microarrays are another tool for systematically analyzing protein-protein interactions, protein-peptide interactions or the interactions of proteins with low molecular weight substances. This method involves applying in-vitro translated or recombinantly produced proteins or peptides, antibodies, specific ligands or low molecular weight substances to a support material, analogously to DNA microarrays. Complex protein mixtures or substance libraries may thus be simultaneously screened, inter alia, for specific interactions (Ashman, Moran et al. 2001) (Xu, Piston et al. 1999). However, the analyses using protein or substance arrays, which are carried out completely in vitro, likewise have great disadvantages. Thus, proteins are prepared or analyzed under completely artificial conditions in this method. Furthermore, the appearance of high unspecific background signals, the limited sensitivity and difficulties in detecting proteins having particular physicochemical properties greatly limit the number of possible applications of these array-based in-vitro analytic methods for detecting and analyzing protein interactions (Ashman, Moran et al. 2001).

There are furthermore various methods known which involve detecting protein interactions in the cell, and thus in vivo, by indirectly activating genetic reporters. Most of the familiar methods are limited to detection of binary protein interactions in karyoplasma and are based on the functional modularity of transcription factors, such as the 2-hybrid system in yeasts, for example (Fields and Song 1989). The 2-hybrid system involves expressing in yeast cells one or more proteins or protein sections as fusion proteins with a DNA binding protein without transactivation capability and using them as "bait" for detecting interacting components. A second protein or protein fragment is expressed as fusion protein with a transcriptional transactivation domain and is the "prey" component. The "prey" component frequently is a fusion protein which comprises a gene product of a complex cDNA library in addition to the transcriptional transactivation domain. The interaction of the bait and prey fusion proteins results in functional reconstitution of the activating transcription factor. The reporter genes used in the 2-hybrid system are enzymes which can be used to detect said protein interaction either by growth selection or by a simple colorimetric assay and which are very sensitive. A reporter gene frequently used in the 2-hybrid system, which makes possible a positive growth selection of cells with specific protein-protein interactions, is the histidine 3 gene which is an essential enzyme for histidine biosynthesis and whose protein-protein interaction-dependent expression enables the cells to grow on histidine-deficient medium. The most frequently used reporter gene whose protein-protein interaction-dependent expression is detectable by a simple calorimetric assay is the beta-galactosidase gene.

The 2-hybrid system was originally developed in yeast, but subsequently variants of the 2-hybrid system have also been described for application in E. coli and in higher eukaryotic cells (Luban and Goff 1995) (Karimova, Pidoux et al. 1998) (Fearon, Finkel et al. 1992) (Shioda, Andriole et al. 2000).

A substantial disadvantage of classical 2-hybrid-based systems is, inter alia, the relatively high rate of false-negatively and false-positively detected interaction partners. This is due, on the one hand, to the high sensitivity of the reporters, but also to spatial coupling of the interaction and the basal transcription machinery. Recently, interaction systems for yeast cells have been described, which spatially decouple the place of interaction from the activation of the reporter genes used or the selection mechanisms used for detection (Maroun and Aronheim 1999). Related systems in yeast also allow at least one interaction partner which may be an integral or membrane-associated protein to be analyzed (Hubsman, Yudkovsky et al. 2001) (Ehrhard, Jacoby et al. 2000).

The functional complementation of proteins or enzymes which is also the basis of classical 2-hybrid-based systems is a method of analyzing interactions in living cells and bacteria, which has been known and applied for some time (Ullmann, Perrin et al. 1965) (Fields and Song 1989) (Mohler and Blau 1996) (Rossi, Charlton et al. 1997) (Pelletier, Campbell-Valois et al. 1998). Transcomplementation means the separation of an intact and functional protein or protein complex into two artificial subunits at the gene level. The two subunits here are per se inactive with respect to the function of the complete protein but are active with respect to their corresponding subunit function and are incapable of self-reconstitution. By providing in a protein interaction-dependent manner close spatial proximity between the two separated subunits, the fusion of such subunits to proteins or protein domains interacting with one another results in complementation of the divided protein, thereby rendering it functional again. The regaining of the function of the protein (e.g. an enzyme) by protein interaction is utilized here directly or indirectly for detection of said interaction (Mohler and Blau 1996) (Rossi, Charlton et al. 1997). The best-known example is transcomplementation of the transcription factor Gal4 which is the basis of the classical yeast 2-hybrid system (Fields and Song 1989).

In addition, transcomplementations and, coupled thereto, methods of detecting protein interactions have been described for different proteins with enzymatic activity, inter alia beta-galactosidase (bGal), dihydrofolate reductase (DHFR) and beta-lactamase (bLac) (Michnick and Remy 2001) (Rossi, Charlton et al. 1997) (Michnick and Galarneau 2001). Protein interactions can be detected indirectly in these systems after transcomplementation of the abovementioned enzymes by way of growth selection or of fluorimetric or calorimetric enzyme detection assays. Depending on the substrate used, detection may usually be carried out only after disruption of the cells and addition of the substrate in vitro.

In contrast, the DHFR-based system enables the interaction or transcomplementation of proteins to be detected also in vivo. For this purpose, a cell-permeable fluorescently labeled antagonist (methotrexate) is added which binds only to the intact protein. The disadvantage here, however, is the fact that the antagonist is not a substrate of the enzyme but binds the enzyme as a competitive inhibitor. Therefore no enzymatic enhancement of the detection signal whatsoever is produced. This results in a strong reduction in the sensitivity of this detection method compared to detection of positive clones by way of positive growth selection under the appropriate culture conditions. Moreover, the detection signal in the DHFR-based system for analyzing protein interactions is visible only directly after addition of the fluorescently labeled inhibitor, i.e. it is not possible to detect dynamic processes in cells, which are frequently accompanied by dynamic or transient protein interactions, by means of these nonpermanent signals which are detectable only for a short time. In addition, the inhibitor described (methotrexate) is a highly cytotoxic substance which, after application, greatly impairs and alters cell growth, metabolism and other intracellular processes and thus distorts the normal in vivo conditions.

Although a DHFR-based method of analyzing protein interactions, which is based on positive growth selection of cells by transcomplemented DHFR, and not on application of methotrexate, offers correspondingly higher sensitivity, it requires periods of several days and weeks, a fact which makes this method appear not particularly suitable for application in high throughput methods, for example in high throughput screening. Owing to these disadvantages, these systems are also of only very limited suitability for analyzing transient or stimulus-induced interactions, since short-time transcomplementation is insufficient in order to enable positive cells to be selected by growth over a longer period. On the other hand, binding of fluorescent antagonists such as methotrexate by the transcomplemented DHFR can be detected only when finding the exact moment of the transient or stimulus-induced interaction.

These problems in detecting transient, i.e. time-limited, protein interactions also relate to the classical 2-hybrid system and to its variants known according to the prior art, since here too reporter systems are used which do not produce any permanent detection signal.

Only when they appear do transient protein interactions result in short-time expression of the reporter genes used, with the gene products of previously used reporter genes being able to generate a detection signal only during their lifetime, meaning that, for the 2-hybrid system and its variants, and in particular for the analysis of weak and transient protein interactions, only a relatively short time is available for detecting the protein interaction-dependent signals. This is a big problem, in particular when a large number of different potential interaction partners of a bait protein need to be tested simultaneously for interaction, as in screening methods, in particular in high throughput screening methods, for example. Screening methods must enable a multiplicity of different potential interactions which possibly may also take place sequentially and possibly possess different strengths of interaction and lifetimes to be analyzed simultaneously at a defined point in time. However, if particular detection signals are detectable only in a narrow "time window", which possibly do not even overlap for different interactions to be detected, the 2-hybrid system, its variants and the known transcomplementation-based detection systems for analyzing protein interactions may not be able to record certain interactions, in particular weak and transient protein interactions.

Another selection system which is based on a specific type of protein transcomplementation is the split ubiquitin system originally developed for studies in yeast and applied recently also in mammalian cells. This system utilizes the separation of ubiquitin into two nonfunctional moieties, an N- and a C-terminal fragment (Nub and Cub) (Johnsson and Varshavsky 1994) (Rojo-Niersbach, Morley et al. 2000). Ubiquitin is a small protein which labels proteins typically fused to its C terminus for cellular degradation. This biological mechanism is used in the split ubiquitin system for detecting protein interactions. In one embodiment of the split ubiquitin system, a first fusion protein comprising the C-terminal fragment Cub, a selection marker protein or fluorescent protein coupled thereto and a first interaction partner, and a second fusion protein comprising the N-terminal fragment Nub and the second interaction partner are heterologously expressed in the cell. A specific interaction of the corresponding fusion proteins restores a correctly folded ubiquitin which the proteasome can detect and process, with the coupled, initially active reporter then being degraded. Accordingly, the system allows negative growth selection focused on the absence of the selection marker or observation of the disappearance of a fluorescent reporter. These embodiments of the split ubiquitin system, described in scientific publications, thus disclose two very weak points, firstly negative selection making rapid and unambiguous detection of relevant interactions difficult and secondly no signal increase taking place in the cell after the interaction. The latter point makes it virtually impossible to detect weak or transient interactions.

The patent WO 95/29195 discloses an embodiment of the split ubiquitin system in which two different fusion proteins which comprise in each case one interaction partner and one part of the ubiquitin are expressed in a cell. One of the two fusion proteins here furthermore comprises a reporter protein which can be proteolytically removed by a ubiquitin-specific protease. Said reporter protein is removed here by a ubiquitin-specific protease only after a specific protein-protein interaction has occurred, and only then is activated. However, this embodiment of the split ubiquitin system does not overcome the fact that a reporter molecule can be released or activated only once per each interaction which has taken place. The latter makes it virtually impossible to detect weak or transient interactions. In addition, the reporter is coupled directly to one of the interaction partners, meaning firstly that the amount of reporter strongly depends on the level of expression and the stability of the interaction partner to which it has been fused. This leads to the possibility of an unstable or readily degradable protein delivering a false-positive signal in the analysis.

Another system, described for mammalian cells, is based on activation and dimerization of modified type I cytokine receptors (Eyckerman, Verhee et al. 2001). Activation of the STAT3 signal pathway in this system can only take place if an interaction between the bait receptor fusion protein and the prey fusion protein occurs. The prey protein is fused to gp130 which carries STAT binding sites. The receptor-associated Janus kinases phosphorylate gp130 only after bait-prey interaction, resulting in binding, phosphorylation and subsequent nuclear translocation of STAT3 transcription factors. STAT-regulated reporter genes are expressed as a function of the bait-prey interaction. To identify novel intracellular interaction partners, a selection strategy was established which confers puromycin resistance (Eyckerman, Verhee et al. 2001). Although the method allows detection of a protein-protein interaction on the membrane by way of expression of a reporter gene, it nevertheless requires at least one interaction partner to couple to said membrane receptor. Moreover, the complex quaternary structure of the receptor-kinase-GP130 multimer is not suitable for analyzing difficult protein classes such as membrane proteins. Owing to insufficient amplification and stability of the signal, the system is incapable of analyzing transient or weak interactions.

Methods based on the transfer of energy quanta of a donor molecule to an acceptor molecule when said molecules are brought into very close proximity have theoretically few limits. These methods may use various variants of the green fluorescent protein (GFP) from *Aequorea victoria*, which are capable of fluorescence resonance energy transfer (FRET) owing to their specific spectral properties (Siegel, Chan et al. 2000). A similar method is based on an energy coupling of the bioluminescence of the luciferase-luciferin reaction as energy donor and GFP as energy acceptor. The energy transfer is referred to as bioluminescence resonance energy transfer (BRET) effect (Xu, Piston et al. 1999). However, the addition of appropriate luciferase substrates is required here. The substantial disadvantages of these methods are the result of the sensitivity and difficulty of detection. The detection of FRET effects in vivo requires both very strong expression and complicated analysis. Strong overexpression of proteins in heterologous cells often results in the formation of aggregates, wrong folding or misdirected subcellular localization. The method provides no possibility of signal enhancement or signal amplification, a decisive disadvantage which rules out detection of weak interactions or interactions of weakly expressed proteins. In order to be able to detect a protein interaction of spectrally compatible GFP fusion proteins by way of FRET effects in the cell, background subtractions and photobleaching analyses must be carried out (Haj, Verveer et al. 2002). Owing to the complex technique, the method is not suitable for high throughput methods of analyzing protein interactions and, in addition, requires complicated analyses and great experience, this being an obstacle to broad application.

All indirect methods previously described have the fundamental disadvantage of coupling conversion of the protein interaction to a detection method which requires constant activation or allows in particular transient interactions to be analyzed only in a very narrow time window. It is therefore possible only in a very limited way, if at all, to analyze protein interactions in post-mitotic cells or to identify transient interactions. Automatable detection of interactions underlying unknown kinetics is thus not possible.

The methods previously described of analyzing or detecting protein-protein interactions thus has at least one or more of the following disadvantages:

The interactions do not take place in vivo, or at least not in mammalian cells.
Large amounts of biological material are required.
The interactions must be permanent or the analysis must take place at exactly the right time.
Measuring the interaction requires complicated measurements and, respectively, apparatus.
Detection sensitivity is very limited.
The analysis of endogenously very weakly expressed genes is restricted.
Only binary interactions are detected.
The rate of false-positive or false-negative interactions is high.
The analysis of cell type-specifically expressed genes in a complex tissue assemblage or in cell lines is virtually impossible in biochemical methods.
The detection methods are automatable only with difficulty.

SUMMARY OF THE INVENTION

It was the object of the present invention to provide a method of detecting and analyzing protein interactions, which overcomes the disadvantages of the prior art listed above. More specifically, it was the object of the present invention to provide a method which also makes weak protein interactions and/or stimulus-induced protein interactions of a transient nature accessible to analysis by generating in a protein interaction-dependent manner a permanent detection signal which no longer depends on analysis in a narrow time window. More specifically, it was also an object of the invention to provide a method of analyzing protein interactions, which comprises generating a detection signal for detecting specific protein interactions, which signal is increased, i.e. amplified, compared to classical activation of a reporter gene by transient transcription activation.

The object of the invention is achieved by providing a method of detecting and analyzing protein interactions in a cell, which comprises the following steps:
a) provision of the activity of at least one enzyme from the group consisting of recombinases and proteases in the cell as a result of a protein interaction,
b) continual generation of an active reporter protein in the cell in question and, where appropriate, in the daughter cells of said cell, as a result of the enzymatic activity of step a) for a period of time which exceeds the duration of the protein interaction of step a),
c) generation of a detection signal by the reporter proteins generated in b).

The novel method overcomes substantial disadvantages of the prior art, since it is particularly suitable for analyzing protein interactions,
which are of a transient nature
which are very weak
which depend on specific stimuli and take place only in vivo
which depend on the intrinsic properties of particular eukaryotic cells
which depend on a particular cellular state
which depend on specific modifications
which depend on a complex topology and environment
which are coupled to the function of protein complexes.

In the method of the invention, a protein interaction can be detected in any living cells or cell assemblages and may take place completely in vivo. Biochemical intervention here is not absolutely necessary. Furthermore, the detection signal increases not gradually, i.e. as a function of the strength of interaction, but is maximally enhanced by switching on a permanently strongly expressed reporter gene or by constant de novo generation of active reporter proteins, even beyond the existence of said protein interaction.

The analysis can be decoupled in time from the possibly stimulus-dependent and/or transient interaction. This makes possible the synchronized analysis of a multiplicity of potential interaction partners, such as, for example, in a screening method. Furthermore, it is possible to study in one experiment sequential stimuli of different signal transduction pathways and their possible influence on regulated protein interactions, also of unknown partners, or to analyze the influence of low molecular weight active compounds on protein interactions. Detection of the reporters is experimentally easy to carry out and compatible to high throughput methods such as, for example, high throughput screening methods. Protein interaction-dependent short-time activating of the reporter system is already sufficient in order to generate a permanent, stable and long-term in vivo detectable signal in the method of the invention. In addition, continual de novo generation of the active reporter protein for a period of time which exceeds the existence of the protein interaction and the accumulation, possibly occurring as a result thereof, of said active reporter protein in the cell increase the signal enormously. The increase here is subject to an "all or nothing principle", where the detection signal is maximally activated, notwithstanding the original strength of interaction, and this proves an advantage, especially in the case of weak and/or stimulus-induced protein interactions of a transient nature.

Furthermore, spatial separation of the protein interaction from the place of signal generation in the method of the invention has the advantage, in comparison with some methods according to the prior art, that the background of false-positive signals should be reduced. These properties are a marked improvement compared to the existing systems. The modularity and enormous flexibility of the system allow the analyses and experiments to be very finely adjusted to the particular problem or to the strength of the interaction required.

The method of the invention of detecting and analyzing protein interactions in a cell involves providing in step a) the activity of at least one enzyme from the group consisting of recombinases and proteases as a result of a specific protein interaction. The activity of the appropriate enzyme in the cell in question may be provided here preferably either by inducing or increasing expression of said enzyme as a result of said protein interaction, by activating, in particular by proteolytically activating, said enzyme as a result of said protein interaction, or by transcomplementation of said enzyme as a result of said protein interaction. In the case of transcomplementation of the enzyme, the occurrence of a specific protein interaction results in two fusion proteins, both comprising in each case part of the amino acid sequence of the enzyme (i.e. either of the protease or of the recombinase), coming into spatial proximity to one another and thus being able to form a transcomplemented, functional enzyme. Furthermore, the protein interaction-imparted spatial proximity between a protease and its substrate may provide the activity of the enzyme.

In step b), the enzyme activity of step a) results in an active reporter protein being continually generated in the cell in question and, where appropriate, in the daughter cells of said cell for a period of time which exceeds the existence of the protein interaction of step a). Here, the period of time which exceeds the existence of the protein interaction of step a) is preferably the period which comprises the entire lifetime of the cell in question. More preferably, the active reporter protein is continually generated in the cell in question and additionally also in the daughter cells of said cell in question over such a period of time which comprises the entire lifetime of the daughter cells. This period which is usually very long and in which the active reporter protein in the cell in question or additionally even in its daughter cell is continually generated de novo preferably also results in a certain accumulation of said active reporter protein in said cell in question and/or in its daughter cell.

In method step c), the active reporter protein generated in step b) generates a detection signal which is measured. Accumulation of the active reporter protein ultimately results in the generation in the method of the invention of a detection signal which is increased compared to a detection signal generated by a reporter protein which has been generated merely during the course of the protein interaction, and which therefore has accumulated less. The detection signal may be the fluorescence of a fluorescent reporter protein such as, in particular, GFP and its variants or luciferase. However, the detection signal may also be the substrate converted by an enzyme functioning as reporter, such as, in particular, in a β-galactosidase assay. Furthermore, resistance-conferring genes or else genes for growth selection may be used as reporter proteins and the resistances or growth conditions resulting from expression of said genes may be used as detection signal.

The principle underlying the method is based on a specific protein interaction converting first to a permanent signal for continual de novo generation of an active reporter protein in the cell. The signals are activated by one or more molecular switch systems coupled to one another which involve proteases and/or DNA double strand-specific recombinases. The system may be designed so as to enable the dynamics of protein interactions, their coming into being and their dissociation to be analyzed.

The method of the invention provides in a protein interaction-dependent manner the activity of at least one enzyme from the group consisting of recombinases and proteases in the cell and converts said activity to a permanent detection signal of said cell. The activity of at least one enzyme from the group consisting of recombinases and proteases initiates in the cell a switch-like mechanism which ultimately results in the formation of a permanent and, compared to activation of a reporter gene by classical transcription activation, greatly amplified detection signal of the cell.

Some preferred embodiments of the method of the invention are based only on generation of a permanent signal by providing in a protein interaction-dependent manner the activity of a recombinase.

These embodiments are based on providing in a protein interaction-dependent manner a DNA recognition sequence-specific recombinase and a reporter system coupled to the function thereof.

DNA double strand-specific recombinases of the integrase family may mediate the substitution or integration of various non-homologous DNA molecules (Lewandoski 2001). The integrase protein family comprises more than 100 known members of various species (reviewed in (Nunes-Duby, Kwon et al. 1998) and in (Esposito and Scocca 1997)). The molecular switch used in transgenic animals or in cell culture is essentially the Cre recombinase of P1 bacteriophage and yeast recombinase FLP (Sauer 1998) (Buchholz, Angrand et al. 1998). The activity of a cell type-specific recombinase or a recombinase expressed in a regulated manner during development may activate in vivo a downstream reporter gene. This makes it possible to permanently activate various molecular markers which may be utilized for a multiplicity of analyses in animals (Lewandoski 2001). Cre recombinase was also used in mammalian cells as reporter gene for analyzing signal transduction mechanisms (Mattheakis, Olivan et al. 1999). Furthermore, Cre recombinase-based gene regulation systems have been described in which target genes can be inducibly switched on or inactivated and which are based on ligand-controlled nuclear import of fusion proteins of Cre recombinase with ligand-binding domains of various nuclear receptors. (Kellendonk, Tronche et al. 1996) (Feil, Brocard et al. 1996) (Metzger, Clifford et al. 1995). DNA double strand-specific recombinases which can permanently activate a reporter gene in a protein interaction-dependent manner are an ideal molecular switch system in order to convert transient interactions to permanent signals. Recombinases and also the great advantages which they provide by generating permanent and, compared to classical transcription activation, greatly amplified detection signals for analyzing protein interactions have not been described previously in connection with the analysis of protein interaction.

In the method of the invention, the activity of a recombinase may be expressed by transcomplementation, by protein interaction-dependent transport from the cytoplasm into the nucleus or transcription factor-dependent as reporter gene. Transcription of the recombinase may be induced by in a protein interaction-dependent manner by transcomplementation, for example by functional reconstitution of a transcription factor, or by protein interaction-dependent transport of a functional transcription activator from the cytoplasm into the nucleus.

A multiplicity of studies exist on regulation of the activity of Cre recombinase as transcriptional reporter gene or by controlled nuclear import, both for in vitro and for in vivo applications for activating downstream genes (Lewandoski 2001). However, none of these studies utilizes Cre recombinase as transcriptional reporter gene or by way of controlled nuclear import for analyzing new or known protein interactions. Likewise no studies about transcomplementation of a recombinase or recombinase activity in connection with the analysis of protein interactions have been described. Cre recombinase binds, as a protein dimer, in each case to a double-stranded DNA recognition sequence the "loxP" recognition sequence. The active, recombination-mediating complex is formed by a homotetramer and two loxP recognition sequences. Intermolecular transcomplementations of mutant Cre proteins, characterized by the loss of different functions, have been described (Shaikh and Sadowski 2000). These studies lead to the conclusion that intermolecular transcomplementation of various Cre mutants is a possible strategy for analyzing protein interactions. Likewise, an intramolecular transcomplementation strategy seems possible, owing to functional analyses of chimeric proteins of the FLP and Cre recombinases and, in particular, owing to the known crystal structure of the protein (Guo, Gopaul et al. 1997). The Cre protein folds into two distinct globular domains (AS 20-129 and AS 132-341) which are connected by a short section.

Depending on the application, the following may be downstream reporter systems activated by the recombinase:

Directly in vivo and in vitro detectable and quantifiable proteins (epifluorescent or autofluorescent proteins such as, for example, green fluorescent protein GFP and its derivatives or Aequorin).

Indirectly in vivo and in vitro detectable and quantifiable enzymes (luciferase, beta-galactosidase, alkaline phosphatase, beta-lactamase, etc.).

Exposed surface proteins which are biochemically detectable or suitable for affinity isolation of cells.

Proteins or enzymes conferring resistance to cytotoxic substances or minimal media (neomycin/G418, puromycin, blasticidin S, zeocin, ampicillin, kanamycin, gentamycin, tetracycline, xanthine-guanine phophoribosyl transferase (XGPT) etc.).

Cytotoxic or pro-apoptotic proteins (diptheria toxin, activated caspases, etc.)

Proteins altering the growth or morphology of the cell in which they are expressed.

In a preferred embodiment of the method of the invention, step a) provides in a protein interaction-dependent manner the activity of a recombinase by transfecting or infecting the cell with the expression vector i), said expression vector i) comprising a recombinase gene under the control of a transcription factor, and continual generation of the active reporter protein in the cell in question according to step b) is carried out via the individual steps b1) to b3):

b1) transfection or infection of the cell with a construct ii) which comprises a stop cassette flanked by recombination sites with the downstream nucleotide sequence of a reporter gene under the control of a constitutive promoter, b2) removal of said stop cassette, flanked by recombination sites, of construct ii) by means of the recombinase of a), b3) constitutive expression of the reporter gene.

The individual transfections or infections of the cell are carried out either transiently or stably according to standard methods.

If expression of the recombinase is induced in such a cell in a protein interaction-dependent manner, said recombinase can excise from the nucleotide sequence of the reporter gene the stop cassette flanked by the recombinase recognition sites. This results in activation of the downstream reporter gene and thus in permanent expression and constant accumulation of the functional reporter protein in the cell.

In a further preferred embodiment of the method of the invention, continual generation of the active reporter protein in the cell in question according to step b) is carried out via the individual steps b1) to b3):

b1) transfection or infection of the cell with a construct ii) which comprises a stop cassette flanked by recombination sites with the downstream nucleotide sequence of a reporter gene under the control of a constitutive promoter, b2) removal of said stop cassette, flanked by recombination sites, of construct ii) by means of a recombinase provided by protein interaction-dependent transcomplementation of a functional recombinase in the nucleus, b3) constitutive expression of the reporter gene.

The protein interaction-dependent transcomplementation of a functional recombinase in the nucleus according to step b2) is carried out by additionally expressing heterologously in the cell a first fusion protein comprising at least one first interaction partner and part of the recombinase, and a second fusion protein comprising at least one second interaction partner and another part of said recombinase.

Accordingly, the occurrence of a specific protein interaction between two interaction partners results in a functional recombinase being reconstituted in the nucleus, which is then in turn capable of removing the stop cassette flanked by plox sites or other recombinase-specific recognition sites from the reporter construct ii), with the reporter gene being activated in the process.

A stop cassette in this connection means a DNA insertion which is inserted into the reporter gene in such a manner that its presence leads to inactivation of said reporter gene. After removing the stop cassette flanked by the recombination sites by means of the recombinase activity provided in a protein interaction-dependent manner, nothing now prevents a permanent activation of the reporter gene and thus constant accumulation of, for example, fluorescent reporter protein or, for example, enzymatic reporter protein. The accumulation of reporter protein furthermore results in a considerable increase in the detection signal in comparison with reporter gene activation by classical transcription activation. The extent of signal amplification here is limited merely by the level of expression of the reporter gene or else by the turnover of the enzymatic activity of said reporter gene, but not by duration or strength of the protein interaction to be detected.

In addition to the molecular switch system based on the protein interaction-dependent recombinase activity, the invention also relates to a further switch system at the molecular level which is based on the activity of a protease, provided in a protein interaction-dependent manner, or on coupling of a protease activity with a reporter activated by proteolytic processing. Similarly to the activity of a recombinase, the short-time activity of a protease may result in generating a permanent detection signal as a result of continual generation of an active reporter protein in the cell beyond duration of the protein interaction.

The invention therefore also relates to embodiments of the method of the invention which utilize both molecular switch systems, one based on a recombinase activity and one based on a protease activity, and to embodiments based only on the activity of one of the molecular switch systems, either the protease activity or the recombinase activity.

In a preferred embodiment based on providing the activity of a protease and of a recombinase, the protease activity is provided by transcomplementation of a functional protease, in particular of the TEV protease.

As example 8 shows, transcomplementation of the TEV protease may be carried out by dividing the protease sequence at arbitrary positions of the protein, but in particular at the positions between amino acids 60 and 80 and at the position between amino acids 95 and 120 of the TEV protease. The two parts of the TEV protease may also overlap here, as likewise shown in example 8. Expression of the two TEV protease fragments to be complemented in each case as fusion protein with a potentially interacting other protein result in fusion proteins comprise protease fragments each of which per se no longer possesses any protease activity. However, if the fusion proteins, owing to an interaction of the two potentially interacting proteins, come into close proximity to one another, the particular protease fragments result in a functional TEV protease.

According to this example of transcomplementation of the TEV protease, other proteases and also other proteins such as, in particular, recombinases or transcription factors, may also be transcomplemented. The ideal positions for dividing the corresponding protein to be transcomplemented must be tested experimentally in each individual case.

This transcomplementation of the functional protease is carried out here via the following steps:

e) expression of
- e1) a first fusion protein comprising the first interaction partner and part of a protease, and
- e2) a second fusion protein comprising the second interaction partner and another part of said protease,
- with, where appropriate, at least one of the two fusion proteins possessing a further domain which causes said fusion protein to be anchored outside the nucleus, and
- e3) expression of a functional recombinase,
  - which, where appropriate, is a further domain of the first or second fusion protein and can be proteolytically removed from the other domains via a recognition and cleavage site for the protease, or
  - expression of a functional recombinase on a third fusion protein which, in addition to the functional recombinase itself which is proteolytically removable via a recognition and cleavage site for the protease, comprises a further domain causing the third fusion protein to be anchored outside the nucleus, in a cell, f) reconstitution of a functional protease due to the first and second interaction partners interacting with one another, g) proteolytic removal of the functional recombinase from its anchoring position outside the nucleus by the reconstituted protease of f), h) transport of the functional recombinase into the nucleus and activation of a recombinase-dependent reporter gene.

The component e3) here possesses preferably a domain for its anchoring outside the nucleus, which results in anchoring on the cell membrane.

In addition, the cytoplasmic structure outside the nucleus, on which at least one of the two fusion proteins is anchored via a domain suitable therefor, may, however, also be any other membrane-enclosed cell organelle, with the exception of the nucleus. Particular proteolytically removable protein targeting domains which effect targeting of the carrier protein into the lumen of a particular cell organelle may be used for fixing at least one of the two fusion proteins outside the nucleus.

In a further, likewise preferred embodiment the activity of a protease is provided in a protein interaction-dependent manner by generating spatial proximity between a functional protease and its substrate by the following steps:

j) expression of
- j1) a first fusion protein comprising the first interaction partner and a functional protease, and
- j2) a second fusion protein comprising the second interaction partner, a functional recombinase domain and a further domain causing anchoring outside the nucleus, with at least said functional recombinase domain being proteolytically removable from the domain which causes the second fusion protein to be anchored outside the nucleus, via a recognition and cleavage site of the protease used, in the cell, k) effecting a spatial proximity, resulting from the interaction of the first and the second interaction partner, between the functional protease of the first fusion protein and the protease recognition and cleavage site on the second fusion protein, l) proteolytically removing the functional recombinase anchored outside the nucleus by cleaving the protease cleavage site with the proximal protease, transporting the free functional recombinase into the nucleus and activating a reporter system.

In another preferred embodiment of the method of the invention, the active reporter protein of step b) is continually generated in the cell in question by providing, as a direct or indirect result of the protein interaction, a specific functional transcription factor in the nucleus of said cell, which induces or increases expression of said reporter protein.

This protein interaction-dependent provision of a specific functional transcription factor in the nucleus of the cell may be accomplished here preferably by the protein interaction-dependent transcomplementation of a functional transcription factor in the nucleus.

Said protein interaction-dependent transcomplementation of a functional transcription factor in the nucleus may be carried out, in particular, via the following individual steps:

m) expression of a first fusion protein comprising the first interaction partner and part of the transcription factor and of a second fusion protein comprising the second interaction partner and another part of the transcription factor,
n) reconstitution of a functional transcription factor due to said first and second interaction partner interacting with one another,
o) induction of expression of a functional recombinase for activation of a recombinase-dependent reporter system in the nucleus.

In another preferred embodiment, the specific functional transcription factor which induces or increases expression of the reporter protein may be provided by the protein interaction-mediated spatial proximity between a protease and its substrate.

Said spatial proximity between a protease and its substrate in the nucleus is preferably generated here by the following steps:
j) expression of
  j1) a first fusion protein comprising the first interaction partner and a functional protease, and
  j2) a second fusion protein comprising the second interaction partner, a functional transcription factor domain and a further domain causing anchoring outside the nucleus, with at least said functional transcription factor domain being proteolytically removable from the domain which causes the second fusion protein to be anchored outside the nucleus, via a recognition and cleavage site of the protease used,
  in the cell,
k) effecting a spatial proximity, resulting from the interaction of the first and the second interaction partner, between the functional protease of the first fusion protein and the protease recognition and cleavage site on the second fusion protein,
l) proteolytically removing the functional transcription factor anchored outside the nucleus by cleaving the protease cleavage site with the proximal protease, transporting the free functional transcription factor into the nucleus and activating a reporter system.

In a further preferred embodiment of the method of the invention, protein interaction-dependent transcomplementation of a protease provides the specific functional transcription factor in the nucleus of the cell.

This protein interaction-dependent transcomplementation of the protease may be achieved, in particular, by the following steps:
p) expression of
  p1) a first fusion protein comprising the first interaction partner and part of a protease, and
  p2) a second fusion protein comprising the second interaction partner and another part of said protease,
  with, where appropriate, at least one of the two fusion proteins possessing a further domain which causes the fusion protein to be anchored outside the nucleus, and
  p3) expression of a functional transcription factor,
    which, where appropriate, is a further domain of the first or second fusion protein and which is proteolytically removable from the other domains of said fusion protein via a recognition and cleavage site for a protease,
    or
    expression of a functional transcription factor on a third fusion protein which, in addition to the functional transcription factor itself which is proteolytically removable via a recognition and cleavage site for said protease, comprises a further domain which causes said third fusion protein to be anchored outside the nucleus;
  in a cell;
q) reconstitution of a functional protease due to the first and second interaction partners interacting with one another;
r) proteolytically removing the functional transcription factor from its anchoring position outside the nucleus by the reconstituted protease of q)
s) providing a functional transcription factor in the nucleus and subsequently inducing expression of a recombinase-dependent or a recombinase-independent classical reporter system.

In a further preferred modification of the method, the functional transcription factor proteolytically removed in step r),
  induces expression of a recombinase-independent, classical reporter system
  and additionally induces expression of the gene of a functional protease for further continual activation of the reporter system employed in the nucleus is step s).

The additional transcriptional activation of the gene of a functional protease by the activity of the functional transcription factor here results in continual generation of an active reporter protein without the use of a recombinase activity.

Another modified embodiment relates to a method of detecting and analyzing protein interactions in a cell, which comprises the following steps:
u) expression of
  u1) a first fusion protein comprising the first interaction partner and part of a protease, and
  u2) a second fusion protein comprising the second interaction partner and another part of said protease, and
  u3) a reporter which can be activated or inactivated by proteolysis, in the cell,
v) reconstitution of a functional protease due to said first and second interaction partner interacting with one another,
w) activation of the proteolysis-activatable or inactivation of the proteolysis-inactivatable reporter by the reconstituted functional protease of step v).

In this embodiment, the component u3) expressed in step u) is preferably a proteolysis-activatable reporter protein whose reporter activity is inactivated by insertion of an additional amino acid sequence and/or by insertion of at least one recognition and cleavage site for a protease and can be proteolytically activated by the activity of a protease.

As an alternative to this, however, it is also possible for the component u3) expressed in step u) to be a proteolysis-inactivatable reporter protein which contains at least one recognition and cleavage site for a protease and whose reporter activity can be proteolytically inactivated.

In this embodiment, providing a protease activity by transcomplementation of a functional protease may alternatively also be provided by the protein interaction-mediated spatial proximity between said protease and its substrate. In this case, the individual method steps of this embodiment are modified as follows.
x) expression of
  x1) a first fusion protein comprising the first interaction partner and a functional protease, and
  x2) a second fusion protein comprising the second interaction partner and a reporter which can be activated or inactivated by proteolysis,
  in the cell;
y) interaction of said first and second interaction partners with one another;
z) activation of the proteolysis-activatable reporter or inactivation of the proteolysis-inactivatable reporter by protein interaction-dependent spatial proximity of the functional protease of the first fusion protein x1) and the proteolysis-activatable or -inactivatable reporter of the second fusion protein x2).

The invention furthermore relates to a method of detecting and analyzing protein interactions in a cell, which comprises the following steps:

J) expression of
- J1) a first fusion protein comprising the first interaction partner and part of a protease, and
- J2) a second fusion protein comprising the second interaction partner and another part of said protease, and
- J3) constitutive expression of a reporter protein which is anchored via a suitable domain outside the nucleus and which can be proteolytically removed from said anchoring position, and additionally comprises a further domain which, after proteolytic removal, effects localization of said reporter protein into a particular compartment of the cell, in the cell, K) reconstitution of a functional protease due to said first and second interaction partners interacting with one another, L) proteolytically removing the reporter protein together with its domain which causes localization of the free reporter protein into a particular compartment of the cell, by the functional protease of step K), M) detecting the altered location of the reporter protein.

Detection systems based on the proteolytic removal of membrane-bound transcription factors have already been developed for application in yeast to isolate new proteases or protease-regulating proteins or molecules (Kamada, Kusano et al. 1998) (Hirowatari, Hijikata et al. 1995) (Broad 1999). The use of exogenous proteases in connection with the analysis of protein interactions has not been described previously.

A proteolytic activity of this kind may take place, as described in detail above, by transcomplementation or by spatially bringing together (proximity) the enzyme and its substrate in a protein interaction-dependent manner. Depending on the application, the following proteins or enzymes may be activated by proteolytic cleavage:

- A recombinase bound outside the nucleus, which enters the nucleus and can become active there only after proteolytic removal.
- A transcription factor fixed outside the nucleus which enters the nucleus and can become active there only after proteolytic removal.
- A GFP variant fixed outside the nucleus which enters the nucleus only after proteolytic removal. Detection is carried out by way of the altered morphology of the fluorescence signal.
- An enzyme or protein or molecule or protein pair or molecule pair activatable or inactivatable by proteolytic cleavage. These may be recombinases, proteases, GFP variants, enzymes or cellular signal proteins.
- A modified protease which likewise can become active only after proteolytic cleavage. The latter results in permanent and maximum signal activation due to a cascade of successive proteolytic cleavages.
- A transcription activator whose nuclear localization signal is masked by a protein domain which is located on the same or on another protein and contains a protease recognition site so as for the nuclear localization signal of said transcription activator to be recognized only after proteolytic cleavage and the latter to be able to enter the nucleus only then.

An essential feature of the present invention is the fact that protein interactions in the cell are recorded at those places where they also naturally occur, for example in the case of ER residence proteins, in the ER or, in the case of surface receptors, on the plasma membrane.

The type of anchoring and the localization resulting therefrom of a proteolytically removable transcription activator, a recombinase or another protease sensor such as, for example, a proteolytically activatable or inactivatable enzyme or a proteolytically activatable or inactivatable fluorescent protein make it possible to specifically detect protein interactions at their natural location within the cell and, in addition, to investigate at which locations within the cell said interaction takes place. The method of the invention therefore comprises various methods of specific anchoring or localization of the abovementioned protease sensors. The proteolytically removable proteins which display their activity in the nucleus, such as transcription activators or transcription factors or recombinases, must be anchored in such a way that they are located on the cytoplasmic side of membranes or cell compartments in order to be able to enter the nucleus after proteolytic removal from the anchoring position. Depending on the application, this involves the following anchorings, for example:

- For localizations on the ER membrane, fusion of the proteolytically removable transcription activator or of the recombinase or of a protease sensor (summarized as proteins to be anchored) to the C terminus of a type I or type III membrane protein with ER retention signal, which resides in the ER, with a protease cleavage site being located between the anchoring protein and the anchored protein.
- For localizations in the Golgi apparatus, fusion to Golgi-residing membrane proteins or, alternatively, isoprenylation of the protein to be anchored or of the protease sensor by appending a protease cleavage site followed by a geranylgeranylization signal, e.g. CVIL, or a farnesylation signal, e.g. CIIM, to the C terminus.
- For localizations on the plasma membrane, fusion of the protein to be anchored to the C terminus of a type I or type III membrane protein or to the C terminus of the transmembrane region of such a membrane protein, with a protease cleavage site being located between the anchoring protein and the anchored protein.
- For localizations on the plasma membrane, fusion of the protein to be anchored to the N terminus of a type II membrane protein or to the N terminus of the transmembrane region of such a membrane protein, with a protease cleavage site being located between the anchoring protein and the anchored protein.

Further, for localizations on the plasma membrane, fusion with protein domains carrying lipid modifications such as myristoylation or palmitoylation, with a protease cleavage site being located between the anchoring protein and the anchored protein.

For localizations on peroxysomes or mitochondria, fusion to a membrane protein located in the peroxysomal membrane or the outer mitochondrial membrane in such a way that the anchored protein is located on the cytoplasmic side and can be removed via a protease cleavage site.

Suitable for analyzing the interaction of cytoplasmic proteins are anchorings of the proteolytically removable transcription activator or of the recombinase or of a protease sensor on the cycoskeleton of the cell, for example by fusion to actin.

Protease sensors capable of directly generating a measurable signal, independently of their localization, such as proteolytically activatable or inactivatable fluorescent proteins or enzymes, may, in addition to the methods mentioned above, also be anchored by appropriate protein fusions on the inside of organelle membranes or be present in a soluble form in the lumen of said organelles due to organelle-specific signal sequences. Examples of such signal sequences are the peroxysome-specific signal, peroxysomal targeting signal 1 (PTS1, SKL), on the C terminus of proteins or N-terminal mitochondrial targeting sequences such as, for example, the first 31 amino acids of the prepeptide of cytochrome C oxidase subunit VIII.

Proteolytic enzymes which are particularly suitable for intracellular use are the potyvirus NIa proteases such as, in particular, the 27 kDa NIa protease of the Tobacco Etch Virus (referred to as "TEV protease" hereinbelow). The TEV protease is very well tolerated in eukaryotic cells and exhibits specific activity in the cytosol (Faber, Kram et al. 2001) (Uhlmann, Wernic et al. 2000). The TEV protease is a member of the C4 family of cysteine proteases, and the primary structure is distinguished by the characteristic distribution of the amino acids of the catalytic triad, histidine (position 46), aspartate (position 81) and cysteine (position 151), (Ryan and Flint 1997). The three-dimensional structure, in contrast, is little known but a secondary structure prediction and comparison with other proteases whose 3D structure has already been resolved implicate a large homology to the trypsin-like serine proteases (Bazan and Fletterick 1988) (Bazan and Fletterick 1989). Their characteristic structural feature is the high proportion of β-sheet domains in the secondary structure which fold to give a typical bilobal overall structure. In the process, the catalytic amino acids histidine and arginine are distributed to the N-terminal lobe and the serine (or cysteine) is located on the C-terminal lobe. This distribution of the three catalytic amino acids to the two "hemispheres" of the protease serves as the basis for the transcomplementation strategy. Several variants are conceivable here which involve dividing the protein into two fragments on which then in each case one or two of the amino acids of the triade can be found. The independent folding of said fragments is crucial for functional transcomplementation. In order to ensure this folding, it may be necessary to generate overlapping fragments and to test these for activity. The aim of transcomplementation is to choose the fragments in such a way that they possess per se no activity and regain this activity only when being fused to interacting proteins, interacting protein domains or other interacting molecules.

Owing to their large structural homology (alignment in (Barrett-A J, Rawlings-N D et al. 1998)), all proteases are suitable in principle for the method. It is required, however, that their presence in the corresponding cells or cell compartments is tolerated. Within the framework of the invention, the protease renin which is usually secreted into the blood stream was also expressed in PC-12 cells. It was possible to detect the intracellular activity with a reporter gene construct equipped with the specific recognition site from the renin substrate angiotensinogen. renin is theoretically very well suited to a transcomplementation strategy, since this protease is very homologous to HIV protease 1 which in turn is known for the functional molecule being composed of two identical subunits.

In addition, it is also possible to carry out transcomplementation of a protease on the cell surface or extracellularly. For this purpose, the fragments and possibly reporters would have to be fused to membrane proteins, proteins of the extracellular matrix or secreted proteins in such a way that they project into the medium outside the cell or are secreted. In such a version of the method, the activity may be detected by adding a substrate or by coexpressing an appropriately modified reporter. Conversion of a specific substrate (e.g. by fluorescently coupled substrate peptides or enzymes whose activity is destroyed by specific proteolysis) ultimately allows transcomplementation to be analyzed in a completely cell-free manner by studying recombinantly or in-vitro produced fusion proteins in the reaction vessel.

The protein interaction-dependent activity of a recombinase and/or activity of a protease in the above-described embodiment of the invention directly or indirectly leads intracellularly to permanent activation of corresponding reporter genes or reporter proteins in the cell. A combination of both systems (the recombinase-based and the protease-based switch systems) allows high sensitivity and provides many possibilities for finely regulating the detection limit or the signal-to-background ratio.

The molecular switch systems are based either on a recombinase activity or a protease activity, or a combination of both systems may then also involve molecular feedback mechanisms which ultimately result in a virtually endless activation of the reporter.

A preferred embodiment of the method of the invention, which comprises such a molecular feedback mechanism for virtually endless signal increase, includes the following individual steps:
A) expression of
   A1) a first fusion protein comprising the first interaction partner and part of a protease, and
   A2) a second fusion protein comprising the second interaction partner and another part of said protease, and
   A3) a protease which can be activated by proteolysis or inactivated by proteolysis,
   in the cell,
B) transcomplementation of a functional protease by the first and second interaction partners interacting with one another,
C) activation of the proteolytically activatable proteases by the transcomplemented functional protease of step B),
D) activation of a proteolytically activatable or a proteolytically inactivatable reporter system by the functional proteases of steps B) and C).

In this embodiment, the occurrence of a specific protein interaction firstly causes transcomplementation of the protease. The functional protease transcomplemented due to protein interaction may then activate by proteolysis both a protease which is constitutively expressed in the cell and which itself is proteolytically activatable and the likewise proteolytically activatable, constitutively expressed reporter protein. Finally, the, similarly to a chain reaction, increasing number of functional protease molecules activated by proteolysis may result in the proteolytically activatable, likewise constitutively expressed reporter protein being provided permanently and virtually endlessly. Alternatively, it is also possible in this embodiment for a proteolysis-inactivatable reporter protein to be constitutively expressed in the cell.

The classical reporter genes which in this embodiment are expressed in the cell in a proteolytically activatable or proteolytically inactivatable form include in this connection the following reporters:

Directly in vivo and in vitro detectable and quantifiable proteins (epifluorescent or autofluorescent proteins such as, for example, green fluorescent protein GFP and its derivatives or Aequorin).

Indirectly in vivo and in vitro detectable and quantifiable enzymes (luciferase, beta-galactosidase, alkaline phosphatase, beta-lactamase, and the like).

Exposed surface proteins which are biochemically detectable or suitable for affinity isolation of cells.

Proteins or enzymes conferring resistance to cytotoxic substances or minimal media (neomycin, puromycin, blasticidin S, zeocin, ampicillin, kanamycin, gentamycin, tetracycline, xanthine-guanine phosphoribosyl transferase (XGPT) and the like).

Cytotoxic or pro-apoptotic proteins (diptheria toxin, activated caspases, and the like).

Proteins altering the growth or morphology of the cell in which they are expressed.

In a modification, the interaction may be detected locally in the nucleus independently of the described reporter system by using alternative reporters. A protease transcomplemented due to protein interaction activates a proteolytically activatable protease and a proteolysis-activatable reporter protein such as GFP, for example. Immediately after synthesis, the constitutively expressed components, the proteolytically activatable protease and the proteolytically activatable reporter protein, are cleaved again, resulting in continual activation. The detection may take place in principle in each compartment and outside the cell. After fusion to appropriate signal sequences, the components are sorted into the corresponding compartments and are processed and activated there. The detection is carried out in situ.

Further modifications of the method above of analyzing protein interactions with virtually endless signal increase are the following embodiments 1.) and 2.) which are discussed in more detail below:

1. In this modification, a protease transcomplemented due to a specific protein interaction proteolytically activates a transcription factor which then, in addition to a conventional reporter gene such as, for example, beta-galactosidase, luciferase, GFP variants, etc. also switches on expression of an intact version of the same protease. Activation of the components is thus followed by continual activation of the complete reporter system: immediately after its synthesis, the constitutively expressed proteolytically activatable transcription factor is independently cleaved again by another protease activity provided by transcomplementation, since the protease coexpressed with the reporter gene is permanently available and can accumulate in the cell.

2. In this further modification, a protease transcomplemented due to protein interaction activates a proteolytically activatable protease and a proteolysis-activatable reporter protein such as, for example, GFP or its variants. The proteolytic activatability of the reporter protein and of the protease, respectively, may be achieved, for example, by inserting one or more recognition sites for the protease into the corresponding protein at the DNA level. After their synthesis, the constitutively expressed components, the proteolytically activatable protease and the proteolytically activatable reporter protein, are proteolytically cleaved and thus activated. In this way there are subsequently always sufficiently functional proteases available which in turn can activate continuously the constitutively expressed proteolytically activatable reporter proteins. The detection signal thus increases itself and is thus permanent.

Detection may take place in principle also in any compartment of the cell and also outside the cell. After fusion with appropriate signal sequences, the components are sorted here into the corresponding compartments and processed and activated there. Detection is carried out here in situ.

3. In this modification of the method, a reporter protein which can be activated or inactivated by proteolysis is constitutively expressed in the cell and is then proteolytically cleaved by protein interaction-dependent transcomplementation of a protease activity and thus, depending on the design of the system, either activated or inactivated. In this embodiment too, the detection signal is increased to a certain extent, since the constitutively expressed proteolytically activatable or inactivatable reporter protein can accumulate in the cell and is thus present in excess. The signal strength may be further increased by using as reporter gene, for example, enzymes with quantifiable activity and with a high turnover rate.

4. In this modification, which is very closely related to the embodiment 3.), a first fusion protein comprising the first interaction partner and a functional protease, and a second fusion protein comprising the second interaction partner and a reporter which can be activated or inactivated by proteolysis are heterologously expressed in the cell.

If a specific protein-protein interaction takes place between the first and the second interaction partner, a close spatial proximity is formed between the functional protease and the reporter protein activatable or inactivatable by proteolysis. Proteolytic activation or inactivation of the reporter protein then, like in embodiment 3.), results in an interaction-dependent detection signal.

The invention furthermore relates to screening methods for identifying a specific interaction partner of a bait protein by carrying out any of the mentioned methods of the invention. Particular preference is given here to screening methods which make use of a cDNA library or an "ORF" (open reading frame) library.

The inventive methods of detecting protein interactions also permit detection of the dissociation of specific protein-protein interactions. Here, the protease activity or recombinase activity is functionally coupled directly to the protein-protein interaction, this being done in such a way that the occurrence of said protein-protein interaction initially does not effect any activation of said protease or recombinase and therefore does not yet cause any permanent activation of the reporter system used. Only the active dissociation then results in activation of the proteases or recombinases and subsequently in activation of the downstream reporter system.

All of the above-described inventive embodiments of analyzing and detecting associations between two interacting proteins may therefore also be used in their "reverse" embodiment. The present invention therefore also relates expressly to these "reverse" embodiments which likewise comprise the generation of permanent detection signals which are increased compared to the classical transcription activation of reporter systems. In some embodiments, even virtually endlessly increased detection signals are generated which indicate the induced dissociation of a specific interaction.

The "reverse" embodiments are especially suitable for those problems concerning the analysis of the dynamics of a specific protein-protein interaction involving two known interaction partners. They are moreover suitable for determining substances having an influence on the constancy of said interaction, thus in particular inhibitors or else activators of said interaction. Thus it would be possible, in particular, to carry out a high throughput screening method, in particular using a library of low molecular weight substances, in order to identify a specific, possibly therapeutically usable inhibitor of a physiologically important protein interaction, which may also be relevant to diseases.

The reverse embodiments of the method of the invention accordingly comprise providing a recombinase activity or protease activity in the cell as a result of the induced dissociation of a defined interaction between interaction partners, in particular between proteins or protein complexes, which are ultimately converted in the cell to a permanent detection signal, i.e. which results, in particular, in activation of a recombinase-dependent reporter system or in activation of a classical reporter system, where appropriate with coexpression of a functional protease, for permanent activation of the complete reporter system.

Accordingly, the invention also relates to a method of detecting and analyzing the dissociation of a defined protein interaction in a cell, which method comprises the steps P) provision of the activity of at least one enzyme from the group consisting of recombinases and proteases in the cell as a result of the dissociation of a protein interaction, Q) continual generation of an active reporter protein in the cell in question or, where appropriate, additionally in the daughter cells, as a result of the enzyme activity of step P) for a period of time which exceeds the duration of the dissociated state of the protein interaction, R) generation of a detection signal by the reporter proteins generated in Q).

In this method too, preference is given to continually generating the active reporter protein in step Q) for such a period of time which comprises the entire lifetime of the cell in question.

This method involves generating the active reporter protein in step Q) in particular not only in the cells in question themselves, but additionally also in the daughter cells of the cell in question, so as to comprise the entire lifetime of said daughter cells.

In all reverse embodiments of the method of the invention, preference is given to detecting stimulus-induced dissociations of a transient nature of the interaction partners in question, since the continual generation of an active reporter protein in this method for a period of time which exceeds the duration over the duration of the dissociated state of the protein interaction, and the accumulation of said reporter protein, resulting therefrom, and also the increased detection signal generated thereby entail particular advantages for dissociations of a transient nature.

The induced dissociation of the defined interaction between proteins or protein complexes is preferably caused by the presence of a specific inhibitor of a protein interaction or by the presence of a specific stimulus which influences the stability or lifetime of a protein interaction.

The classical reporter systems include within the scope of the present invention fluorescent reporter proteins such as GFP and all its commercially available variants, enzymes with detectable activity, such as luciferase, beta-galactosidase, etc., or genes conferring resistance or genes whose expression is required for the cells to grow under particular deficiency conditions. It is furthermore possible to use in the embodiments of the invention all proteolytically activatable and proteolytically inactivatable forms of the abovementioned reporter gene systems.

In a preferred reverse embodiment of the method of the invention, steps a) and b), as a result of the induced dissociation of a protein interaction, are carried out via the following individual steps:

S) expression and interaction of
    S1) a first fusion protein comprising the first interaction partner and a functional recombinase, and
    S2) a second fusion protein comprising the second interaction partner and an inhibitor of said recombinase, in the cell, T) induced dissociation of the interacting fusion proteins, thereby removing the proximity between the recombinase and its inhibitor, U) activation of a recombinase-dependent reporter system by the functional recombinase of step T).

This reverse embodiment of the method may also be modified in such a way that, as a result of the dissociation of a defined protein interaction, the activity of a recombinase is provided and that continual generation of the active reporter protein according to step b) is carried out by providing, as a function of said dissociation of said defined protein interaction, a specific transcription factor in the nucleus of the cell, which then induces expression of a recombinase and, as a result of this, activates a recombinase-dependent reporter gene.

In detail, this embodiment may preferably be accomplished via the following individual steps:

V) expression and specific interaction of
    V1) a first fusion protein comprising the first interaction partner and a functional protease, and
    V2) a second fusion protein comprising the second interaction partner and an inhibitor for said functional protease, and
    with, where appropriate, at least one of the two fusion proteins possessing a further domain resulting in the anchoring of the fusion protein outside the nucleus, and
    V3) expression of a functional protein selected from the group consisting of transcription factors, recombinases and proteolytically activatable or inactivatable reporter proteins,
    which protein, where appropriate, is a further domain of the first or the second fusion protein and which is proteolytically removable from the remaining domains by a recognition and cleavage site for the protease,
    or which, where appropriate, is a further constitutively expressed fusion protein and a domain for anchoring outside the nucleus and which is proteolytically removable from its anchoring position via a recognition and cleavage site for said protease,
    V4) where appropriate, expression of a proteolytically activatable protease,
    in the cell, W) induced dissociation of the interacting fusion proteins, thereby removing the proximity between the protease and its inhibitor and providing a functional protease, X) proteolytically removing the functional recombinase or the functional transcription factor of R3) from its anchoring position outside the nucleus by the functional protease of step W) and transport into the nucleus, Y) activation of a recombinase-dependent reporter system or
    proteolytic activation of the proteolytically activatable protease of Rd) by the functional protease of step W), Z) activation or inactivation of the proteolytically activatable or inactivatable reporter proteins of R3) by the functional proteases of step W) and of step Y).

The fusion of a functional protease to an interaction partner A and fusion of a specific protease-inhibiting protein or peptide to interaction partner B block the proteolytic activity. Said interaction partners may also be components of a protein complex. After dissociation, the protease becomes active and can activate the reporter system. Coupling to a permanently activated reporter system may also detect transient dissociation.

A constitutively expressed functional protein component which is initially anchored outside the nucleus and which is particularly suitable here, is a transcription factor suitable for activating a reporter gene or else a recombinase whose activity induces, by excising a stop cassette flanked by recombination recognition sites from a reporter gene, expression of said reporter gene.

Accordingly, in a modification of the reverse embodiment above, the functional protein V3) expressed in step V) is a functional transcription factor proteolytically removable from its anchoring position outside the nucleus and which is proteolytically removed from its anchoring position in step X) by the functional protease of step W) and which activates in step Y) a recombinase-independent, classical reporter gene.

In another modification of the reverse embodiment above, the further functional protein V3) expressed in step V) is thus a functional recombinase proteolytically removable from its anchoring position outside the nucleus and which in step X) is proteolytically removed from its anchoring position by the functional protease of step W) and which activates in step Y) a recombinase-dependent reporter gene.

Alternatively to expressing a functional protein component anchored outside the nucleus it is also possible to express heterologously a proteolytically activatable or proteolytically inactivatable reporter protein in the cell, which can then be proteolytically activated or inactivated by the protease activity provided in a dissociation-dependent manner. This may be converted into a permanent detection signal by coexpressing a proteolytically activatable protease.

In a further modification of the reverse embodiment above, the further functional protein V3 expressed in step V) is a proteolytically activatable reporter protein or a proteolytically inactivatable reporter protein which is proteolytically activated or proteolytically inactivated in step X) by the functional protease of step W) and which is directly quantified, with step Y) being dispensed with. The proteolytically activatable or proteolytically inactivatable reporter protein need not necessarily be anchored outside the nucleus here.

In a further reverse embodiment of the method of the invention and as a result of the induced dissociation of a specific protein interaction, the activity of a recombinase is provided and converted to a permanent detection signal by the following steps:

expression and specific interaction of
a first fusion protein comprising the first interaction partner and a transcription factor having a DNA binding domain and a weak transcription activation domain, and
a second fusion protein comprising the second interaction partner and a strong transcriptional repression domain,
in the cell,
induced dissociation of the interacting fusion proteins,
induction of transcription of the recombinase gene by the first fusion protein.

In this method, the transcription factor which is functional per se and which is contained in the first fusion protein is kept inactive by the functionally dominating strong transcriptional repression domain on the second fusion protein, until an induced dissociation of the specific protein-protein interaction takes place and thus the proximity between the transcriptional repression domain and the transcription factor is removed. After dissociation of the interacting components, the reporter genes are thus expressed and permanently activate the reporter system.

In a further reverse modification of the method of the invention, the interaction of two fusion proteins may mask a transport signal (e.g. a nuclear import signal of one of the partners). This transport signal is released again only after dissociation of the protein interaction, and the corresponding fusion protein can only then enter the nucleus and, as activating transcription factor, activate reporter gene systems.

The invention furthermore relates to a screening method for identifying and characterizing specific inhibitors of a defined protein interaction or for identifying and characterizing a defined stimulus which influences a defined protein interaction by carrying out any of the reverse methods of the invention mentioned above.

The invention furthermore relates to the cells into which the protein components required in the various embodiments of the invention have been heterologously incorporated at the DNA level in expression vectors. To this end, the cells may be incorporated either stably or transiently with the appropriate expression vectors comprising expression cassettes of the desired protein components.

The invention thus relates to to a cell which has been transfected or infected with at least one expression vector, said expression vector comprising at least one, preferably at least two, in particular at least three, of the constructs i) to vii).

The constructs i) to vii) are defined here as follows:
i) a construct comprising a recombinase gene being under the control of a transcription factor
ii) a construct comprising a stop cassette flanked by recombination sites with the downstream nucleotide sequence of a reporter gene under control of a constitutive promoter,
iii) a construct comprising a recombinase which is anchored outside the nucleus and which can be proteolytically removed,
iv) a construct comprising a transcription factor which is anchored outside the nucleus and which can be proteolytically removed,
v) a construct comprising a proteolytically activatable or inactivatable reporter protein,
vi) a construct comprising a proteolytically activatable protease,
vii) a protease gene under the control of a transcription factor.

The cells used for the method of the invention are either yeast cells, bacterial cells or cells of higher eukaryotic organisms (in particular neuronal cells and mammalian cell lines [e.g. embryonic carcinoma cells, embryonic stem cells, P19, F9, PC12, HEK293, HeLa, Cos, BHK, CHO, NT2, SHSY5Y cells]).

The invention further relates to a kit for detecting and analyzing protein interactions in a cell, which comprises expression vectors comprising the nucleic acid constructs 1a) and 2a) in each case under the transcriptional control of a heterologous promoter:
1a) a first nucleic acid construct coding for a first fusion protein comprising the nucleic acid sequence coding for a first protease fragment and a cloning site suitable for cloning the bait protein in the reading frame of the first protease fragment, and
2a) a second nucleic acid construct coding for a second fusion protein comprising the nucleic acid sequence coding for a second protease fragment and a cloning site suitable for cloning the prey protein in the reading frame of the second protease fragment,
and which, where appropriate, comprises expression vectors comprising at least one of the following constructs:
3a) a nucleic acid construct coding for a functional recombinase or for a functional transcription factor which can be proteolytically removed via a recognition and cleavage site for a protease from a domain for anchoring to a cytoplasmic structure, it being possible for said components to be used either as further moieties of the first or second fusion protein or as separate third fusion protein;
4a) a nucleic acid construct coding for a recombinase under the control of the functional transcription factor of No. 3;
5a) a nucleic acid construct comprising a stop cassette flanked by recognition sites for recombinases with the downstream nucleotide sequence of a reporter gene under the control of a constitutive promoter;

6a) a nucleic acid construct coding for a proteolytically activatable or proteolytically inactivatable reporter protein under the control of a promoter;
7a) a nucleic acid construct coding for a proteolytically activatable protease under the control of a promoter.

The kit may also contain expression vectors which, instead of the abovementioned nucleic acid constructs 1a) and 2a), also comprise modified variants of these two constructs, namely a first nucleic acid construct which comprises a functional protease and a cloning site for cloning the bait protein in the reading frame of said protease and a second nucleic acid construct which comprises a functional, proteolytically removable protein from the group consisting of recombinases or transcription factors and a cloning site for cloning the prey protein in the reading frame of said removal protein.

The kit may furthermore also contain expression vectors which, instead of the nucleic acid constructs 1a) and 2a) above, also comprise further modified variants of these two constructs, namely in particular a first nucleic acid construct which comprises a functional enzyme from the group consisting of proteases and recombinases and a cloning site for cloning the bait protein in the reading frame and a second nucleic acid construct which comprises the sequence for a functional inhibitor or activator for the functional enzyme from the group consisting of proteases and recombinases and a cloning site for cloning the prey protein in the reading frame.

The expression vectors are preferably provided in the kit in such a way that the individual components of a cDNA library have already been cloned into the cloning site of the second nucleic acid construct.

The invention further relates to a kit for detecting and analyzing protein interactions in a cell, which comprises expression vectors comprising the nucleic acid constructs 1b) and 2b) in each case under the transcriptional control of a heterologous promoter:
1b) a first nucleic acid construct coding for a first fusion protein comprising the nucleic acid sequence coding for a functional protease and a cloning site suitable for cloning the first interaction partner into the reading frame of said functional protease, and
2b) a second nucleic acid construct coding for a second fusion protein comprising the nucleic acid sequence coding for a protein selected from the group consisting of recombinases, transcription factors and reporter proteins,
a cloning site suitable for cloning the second interaction partner into the reading frame of said protein,
and, where appropriate, a nucleic acid sequence coding in the reading frame of said protein for a protein domain resulting in the second fusion protein being anchored outside the nucleus,
and, where appropriate, which comprises expression vectors which comprise at least one of the constructs:
3b) a construct for expressing a recombinase gene under the control of the functional transcription factor of No. 2;
4b) a construct which comprises a stop cassette flanked by recognition sites for recombinases with the downstream nucleotide sequence of a reporter gene under the control of a constitutive promoter.

The invention further relates to a kit for detecting and analyzing protein interactions in a cell, which comprises expression vectors comprising at least one of the nucleic acid constructs 1c) and 2c), in each case under the transcriptional control of a heterologous promoter:
1c) a first nucleic acid construct coding for a first fusion protein, comprising the nucleic acid sequence coding for a first part of a protein selected from the group consisting of transcription factors or recombinases and a cloning site suitable for cloning the first interaction partner into the reading frame of said protein,
2c) a second nucleic acid construct coding for a second fusion protein, comprising the nucleic acid sequence coding for a second part of a protein selected from the group of transcription factors or recombinases and a cloning site suitable for cloning the second interaction partner into the reading frame of said protein,
and which comprises, where appropriate, expression vectors comprising at least one of the following constructs:
3c) a construct for expressing a recombinase gene under the control of the functional, transcomplemented protein of No. 1 and 2, said protein being a transcription factor;
4c) a construct comprising a stop cassette flanked by recognition sites for recombinases with the downstream nucleotide sequence of a reporter gene under the control of a constitutive promoter.

The invention further relates to a kit for detecting and analyzing protein interactions in a cell, which comprise at least one expression vector comprising at least one of the nucleic acid constructs 1d) and 2d) in each case under the transcriptional control of a heterologous promoter:
1d) a first nucleic acid construct coding for a first fusion protein comprising a functional enzyme from the group consisting of proteases or recombinases and a bait protein, and
2d) a second nucleic acid construct coding for a second fusion protein comprising a functional inhibitor for an enzyme of the group consisting of proteases and recombinases and a prey protein.

All of the required protein components of the methods of the invention may be incorporated here into the test cells both by transient and by stable transfection or infection. Incorporation into the test cells may be carried out by way of appropriate expression vectors by any of the transformation and transfection techniques known to the skilled worker but, alternatively, also by infection with retroviruses or by other viral-based methods.

The present invention furthermore also relates to the use of at least one enzyme from the group consisting of recombinases and proteases for protein interaction-dependent generation of a permanent and increased detection signal in the cell.

The embodiments and reverse embodiments described of the method of the invention of analyzing the association and dissociation, respectively, of interaction partners or of components of a protein complex are particularly suitable for
A) isolating unknown proteins from cDNA or ORF (open reading frame) libraries, which interact with a known partner in a stimulation-dependent manner, or characterizing novel interactions of known proteins and identifying interaction domains and regulatory mechanisms.
B) elucidating biological mechanisms which control the formation of protein complexes and the dynamic composition thereof.
C) isolating substances which interfere directly or indirectly with specific protein interactions, i.e. which inhibit or promote said protein interactions.
D) characterizing stimulus-dependent protein-protein interactions for a multiplicity of different signal transduction pathways. Said interactions may then be utilized as detection methods for activation of the corresponding cellular signaling mechanisms or for analysis of the physiological state of cells, for example after addition of active compounds or after a change in culturing conditions.

The following strategies and techniques are suitable for identifying and characterizing novel protein interactions:

1.) cell lines which stably express relevant components of the reporter system may be infected with a complex mixture of retroviruses, said retroviruses being constructed in such a way that, after integration, a known bait fusion protein and an unknown prey fusion protein can be coexpressed in a cell. The prey fusion proteins may be prepared by molecular cloning of tissue- or celltype-specific complex cDNAs. The bait and prey fusion proteins may be coexpressed via bicistronic RNAs, using internal ribosomal entry sites, the IRES elements (such as, for example, the EMC virus), (Vagner, Galy et al. 2001) (Pestova, Kolupaeva et al. 2001). The use of bidirectional promoters likewise enables two proteins to be simultaneously coexpressed (Baron, Freundlieb et al. 1995). Unknown interaction partners may be identified by amplifying and sequencing the expressed cDNAs from cells or cell clones selected by growth or isolated by fluorescent-activated-cell-sorting (FACS).

2.) Cell lines which stably express relevant components of the reporter system may be infected with a complex mixture of retroviruses, said retrovirus being constructed in such a way that, after integration, in each case one unknown bait-prey pair is coexpressed in a cell. The bait and prey fusion proteins may be prepared by molecular cloning and combination of defined complex cDNA pools. Coexpression and identification of the unknown partners may be carried out as described under 1.).

3.) Cell lines which stably express relevant components of the reporter system may be infected with a complex mixture of retroviruses, said retroviruses being constructed in such a way that, after integration, in each case one unknown prey fusion protein is expressed in a single cell. After transient transfection or infection of an appropriately large number of cells with expression plasmids coding for one or more bait fusion proteins, it is possible to isolate novel interaction partners, as described under 1.).

4.) The strategy described under 3.) may also be carried out in cells expressing no or only one component of the relevant reporter system. In the case of transient transfection or infection of the bait expression plasmid, the missing components must also be introduced into the cell.

5.) Various cell types which express, but need not necessarily express, components of the reporter system in a stable manner may be analyzed in high throughput transfections or transformations of complex libraries of characterized prey expression plasmids together with one or more known bait expression plasmids. In the case of unmodified cells, components of the preferred reporter system may have to be cotransfected. Complex plasmid libraries with a continually increasing number of defined cDNAs having an open reading frame (ORF) are offered by several suppliers (Brizuela, Braun et al. 2001). The format of these libraries is designed in such a way that the desired N- or C-terminal fusion proteins may be expressed in appropriate plasmid vectors by simple recombination (Simpson, Wellenreuther et al. 2000). Detection requires that, with a given transfection efficiency, a sufficiently large number of cells per reaction mixture has been transfected. Detection may be carried out via automated image analysis, when fluorescent reporters are used, or by established methods according to the prior art, when enzymatic or bioluminescent reporters are used.

6.) As described under 5.), cells may be transfected with a combination of appropriate expression plasmids for analyzing protein interactions, said transfection being achieved by applying the plasmid DNA or plasmid DNA mixture to an appropriate surface and treatment with particular transfection agents. This method is referred to as "reverse transfection" and makes possible simultaneous high throughput analysis of appropriate ORF expression libraries (Ziauddin and Sabatini 2001).

7.) It is furthermore possible, by using the detection methods described herein, which may convert transient effects to a permanent signal, to utilize common methods of introducing peptide or protein fusions into cells, although the stability of exogenous proteins or peptides in the cell may be very brief. Common methods of introducing peptides or fusion proteins have been described by Prochiantz (Prochiantz 2000). The appropriate fusion proteins which can enter cells may have been modified beforehand in various ways, for example by coupling of low molecular weight active compounds, by coupling of particular lipids or of other substance classes.

BRIEF DESCRIPTION OF THE DRAWINGS

The method of the invention will be further illustrated by the drawings:

In order to make clear the molecular switch mechanisms, the diagrammatic drawings depict inactive elements in gray, with activated elements having a black background.

In the drawings,

FIG. 1 depicts the diagrammatic representation of the plasmid construct used for the Cre recombinase-dependent two-hybrid system in mammalian cells;

FIG. 2 depicts a flowchart of the Cre recombinase-dependent two-hybrid system for detecting constitutive protein-protein interactions;

FIG. 3 depicts GFP-fluorescence and phase contrast images of the stable PC12 cell line #20 after transfection with CMV-STOP/EGFP and GV;

FIG. 4 depicts GFP-fluorescence and phase contrast images of the stable PC12 cell line #20 after transfection with CMV-STOP/EGFP and GV, three days after neuronal differentiation by NGF;

FIG. 5 depicts GFP-fluorescence and phase contrast images of the stable PC12 cell line #20.4 after transfection with GV;

FIG. 6 depicts GFP-fluorescence and phase contrast images of the stable PC12 cell line #20.4 after transfection with GV and BlasticidinS selection for four weeks;

FIG. 7 depicts GFP-fluorescence and phase contrast images of the stable PC12 cell line #20.4 after transfection with GV, G-ME2bHLH and V-ND;

FIG. 8 depicts GFP-fluorescence and phase contrast images of the stable PC12 cell line #20.4 after transfection with GV, G-ME2bHLH and V-ND, after addition of TSA;

FIG. 9 depicts GFP-fluorescence and phase contrast images of the stable PC12 cell line #20.4 after transfection with GV, G-GBR2cc, V-GBR2cc, G-GBR2ccDel and V-GBR2ccDel;

FIG. 10 depicts the evaluation of FACS analysis of the stable PC12 cell line #20.4 after transfection with GV, G-GBR2cc, V-GBR2cc, G-GBR2ccDel and V-GBR2ccDel;

FIG. 11 depicts a flowchart of the Cre recombinase-dependent two-hybrid system for detecting induced and transient protein-protein interactions;

Figure 12:
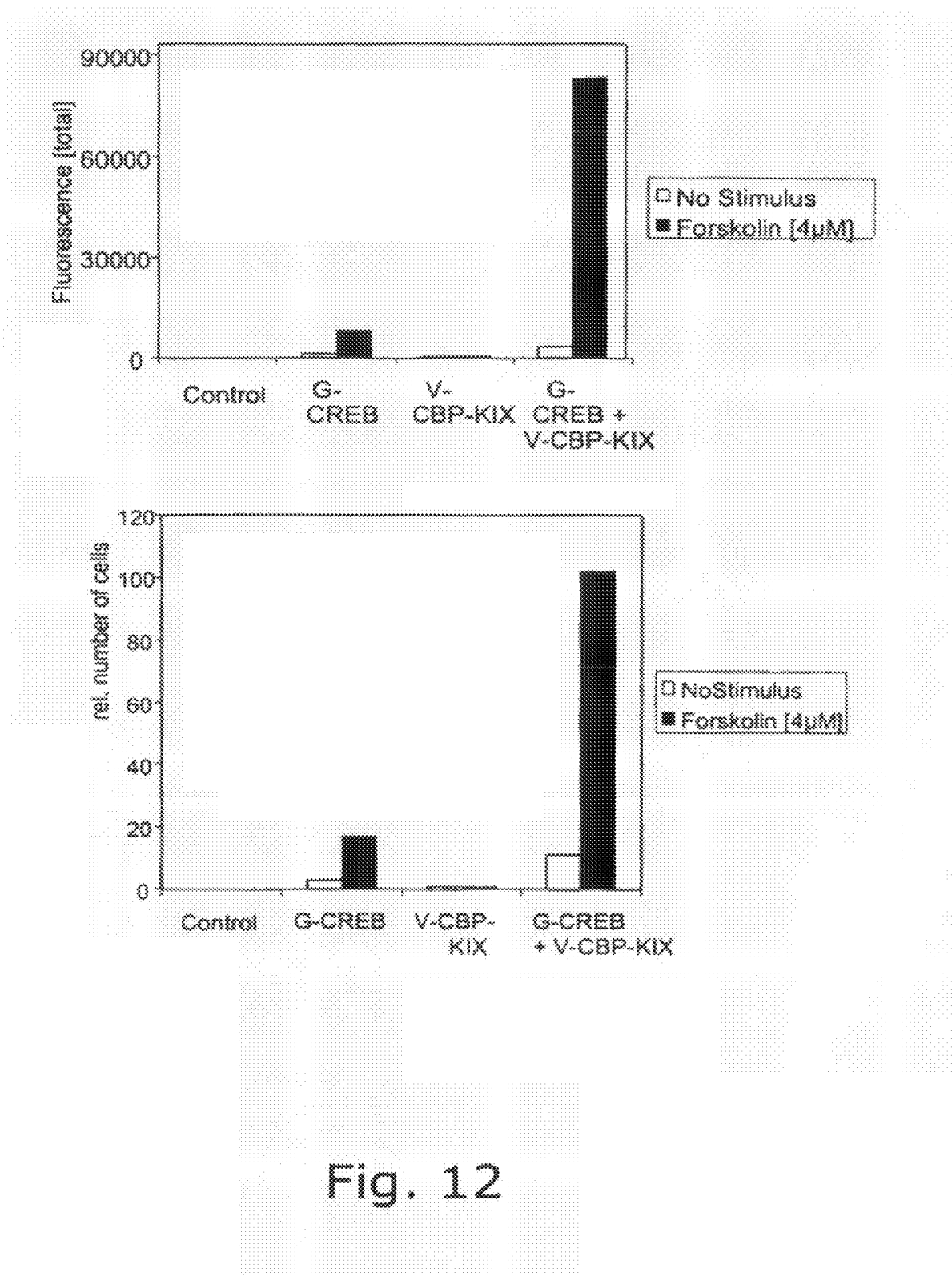
Figure 13:
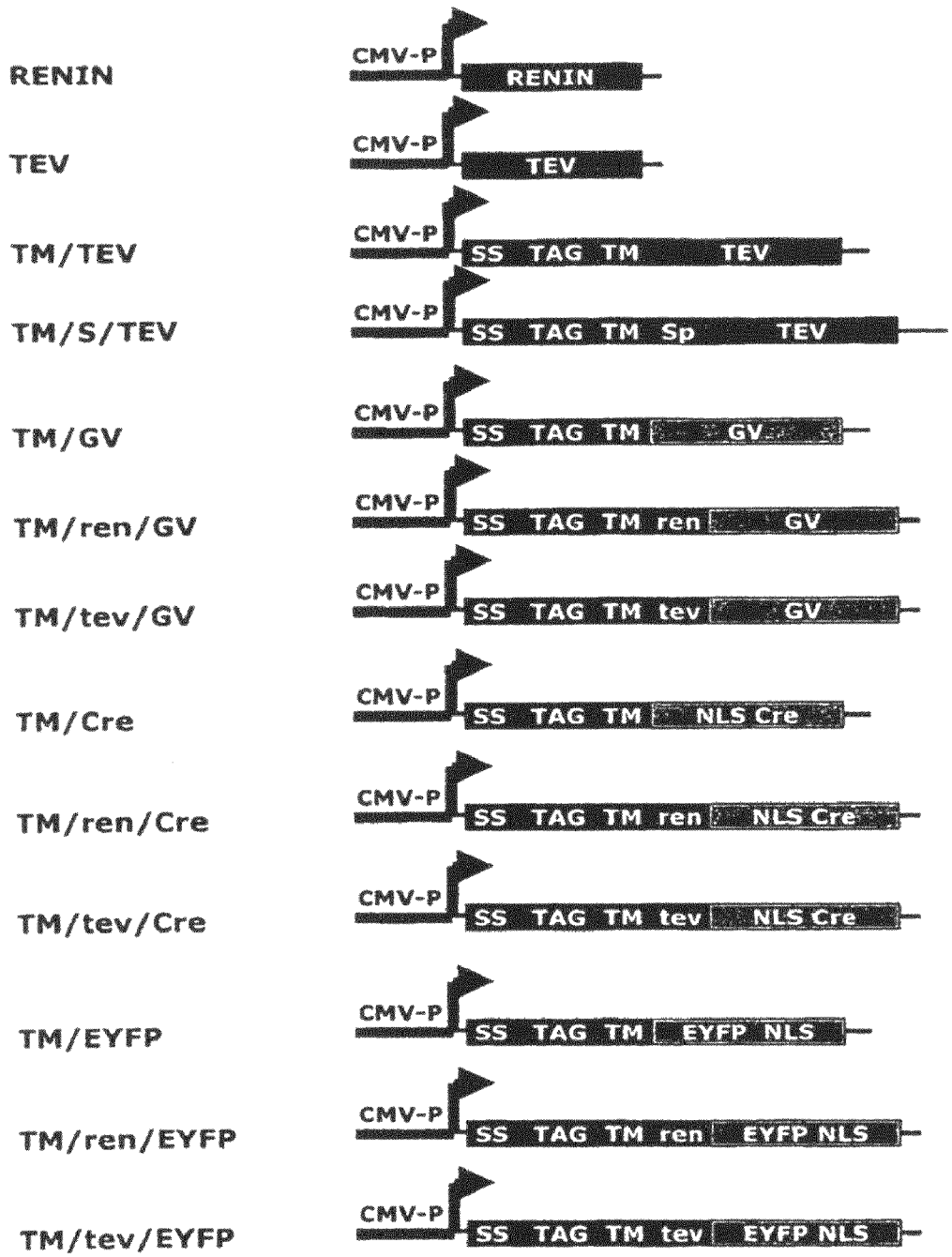
Figure 14:
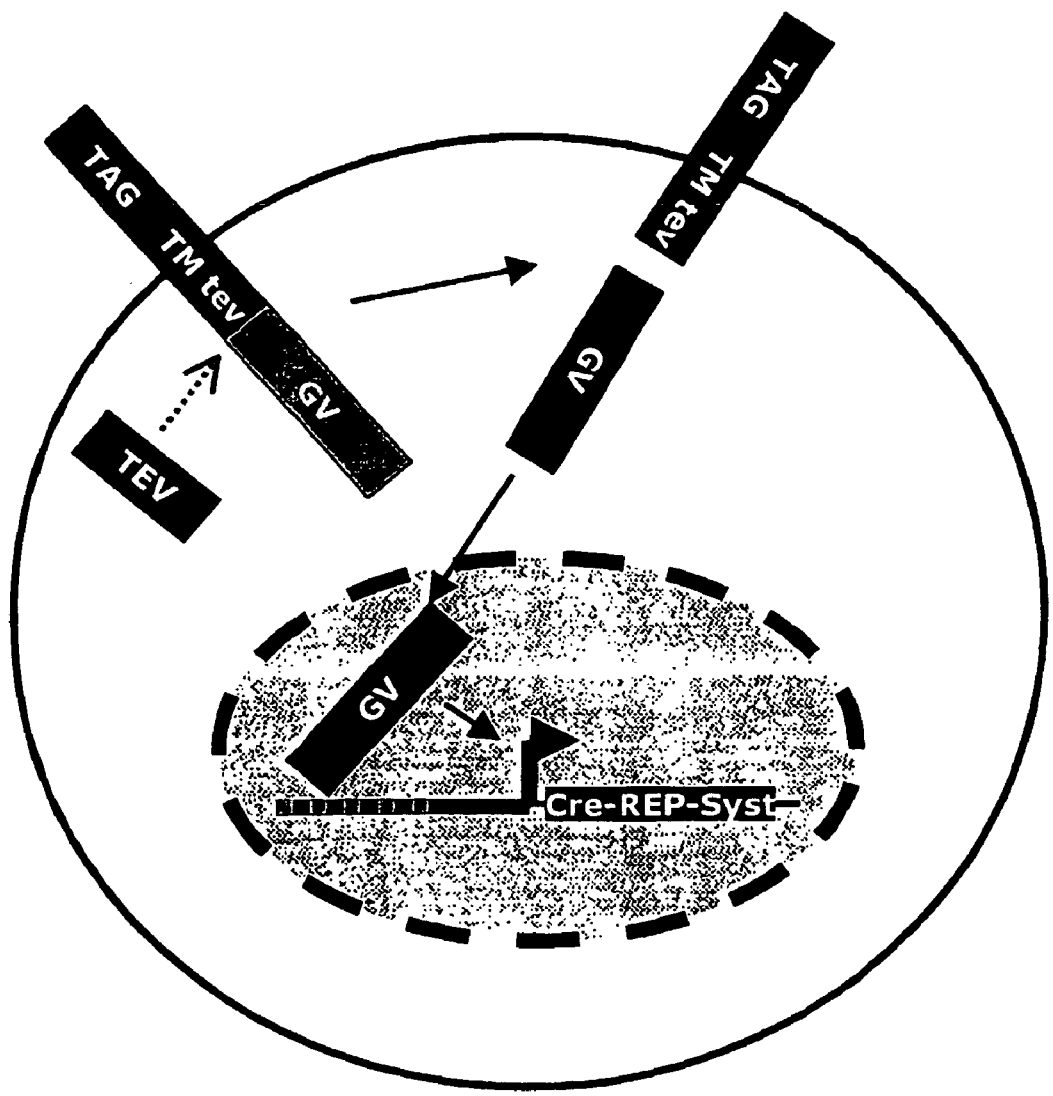
Figure 15:
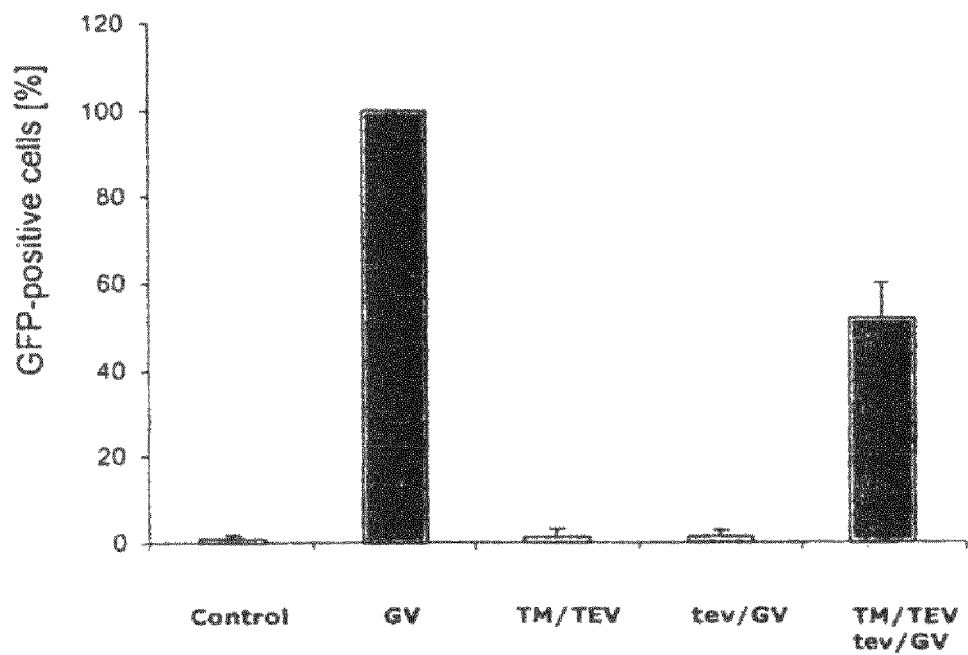
Figure 16:
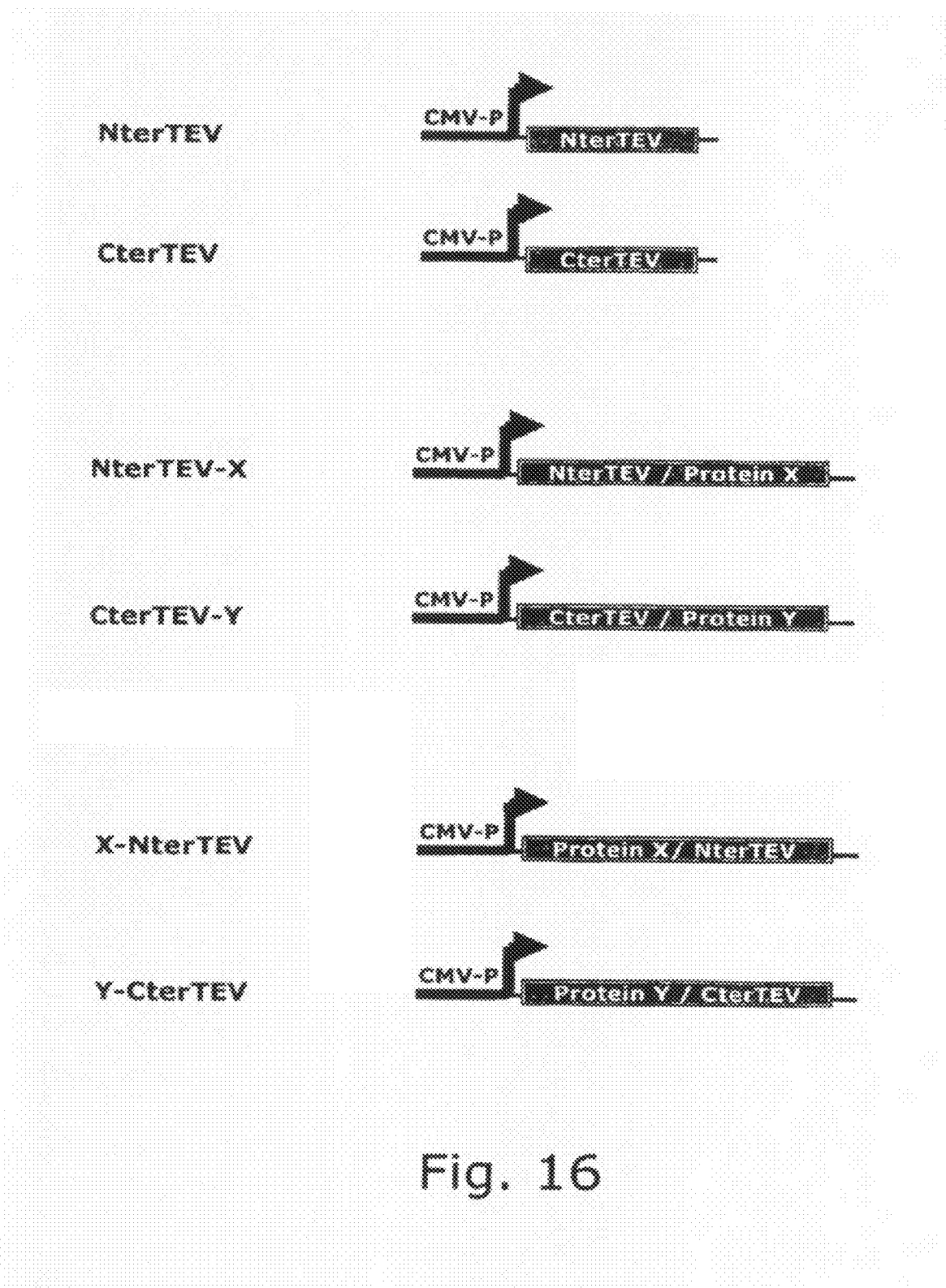
Figure 17:
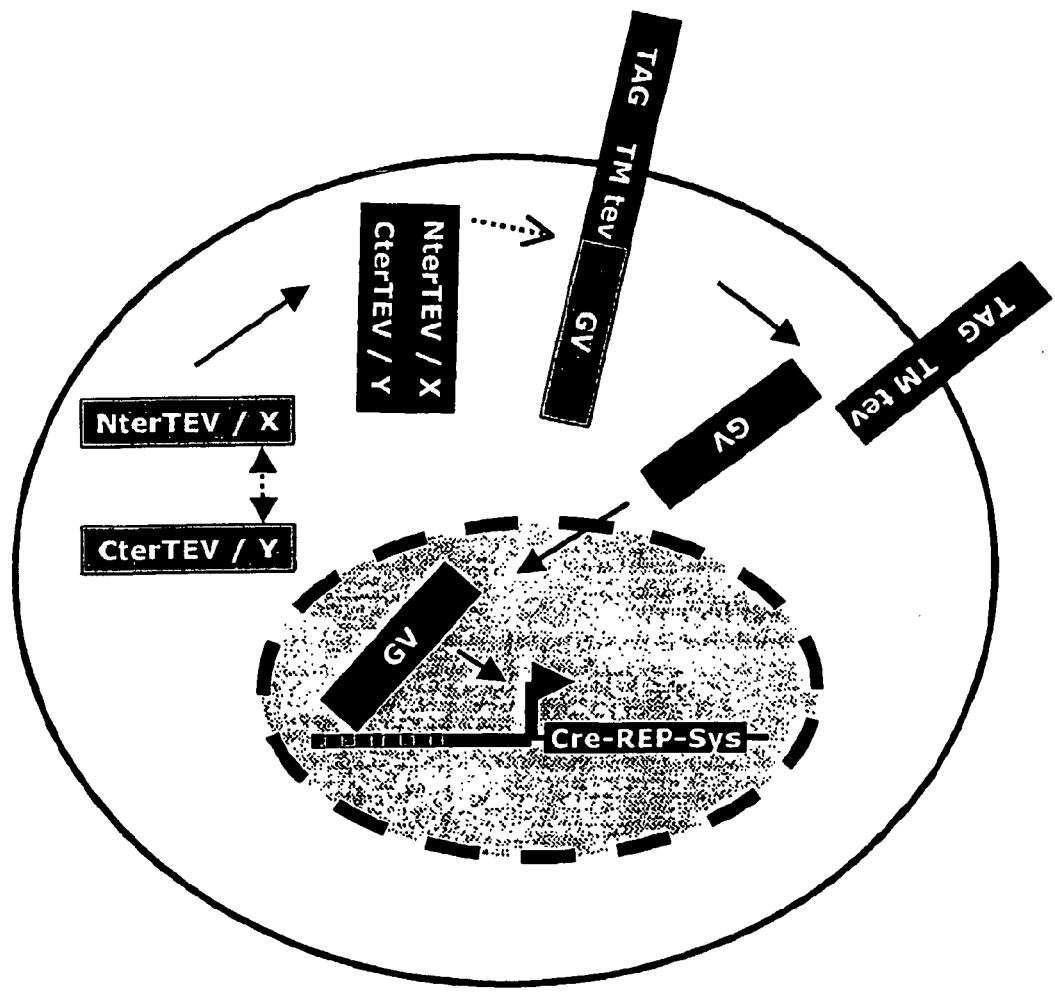
Figure 18:
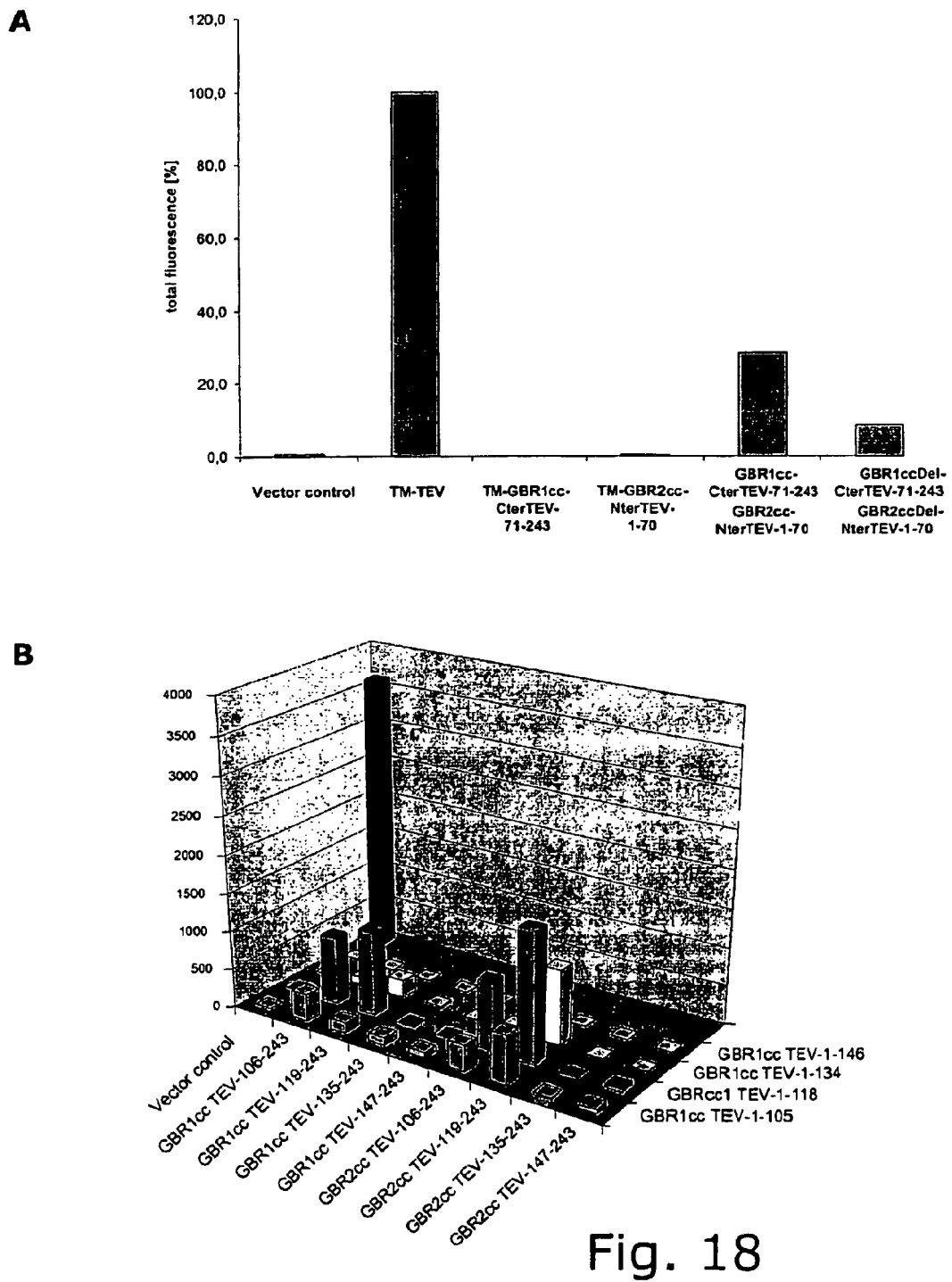
Figure 19:
Figure 19:
Figure 20:
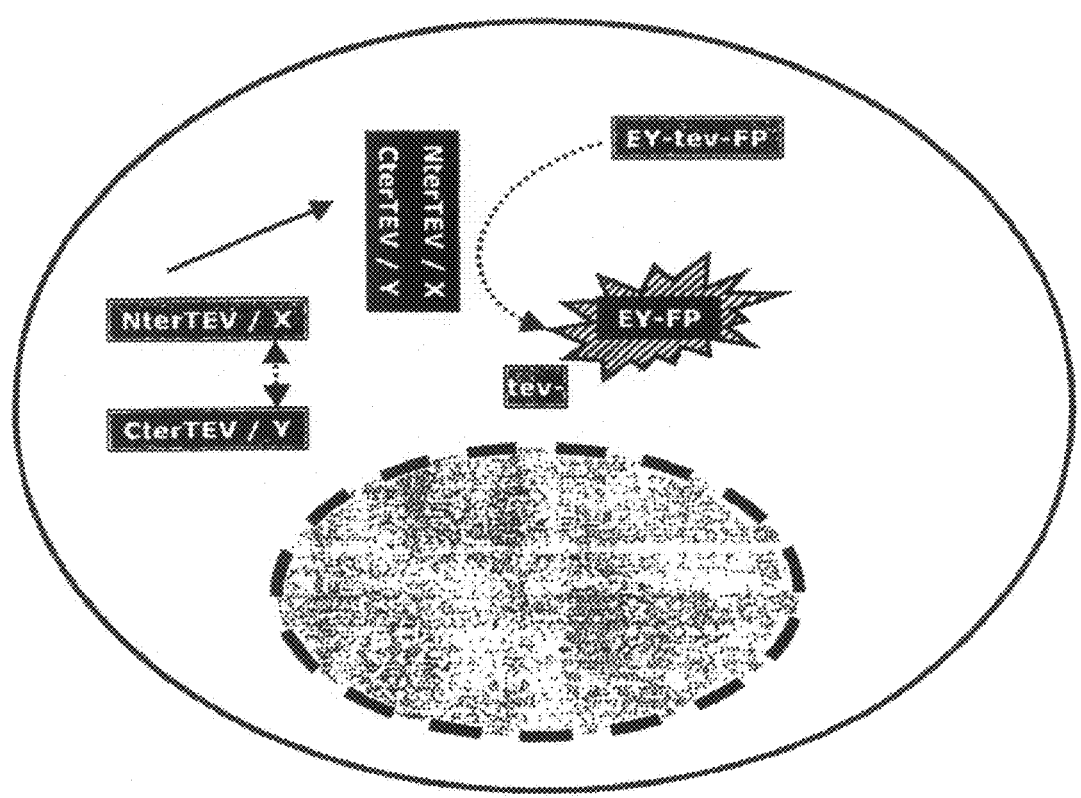
Figure 21:
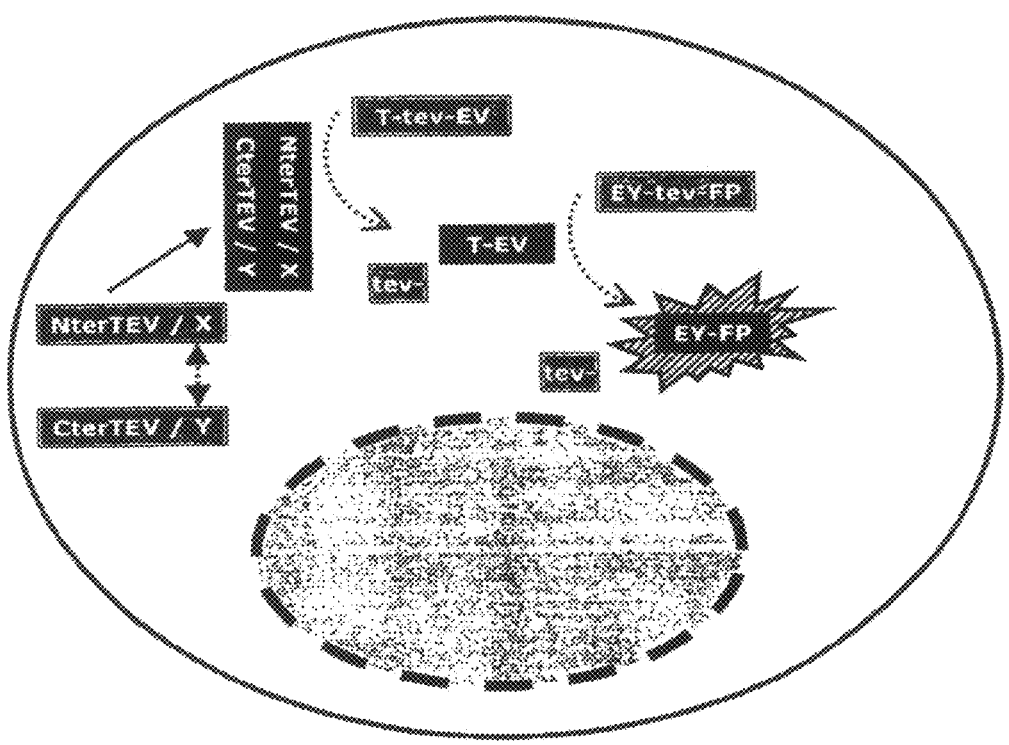
Figure 22:
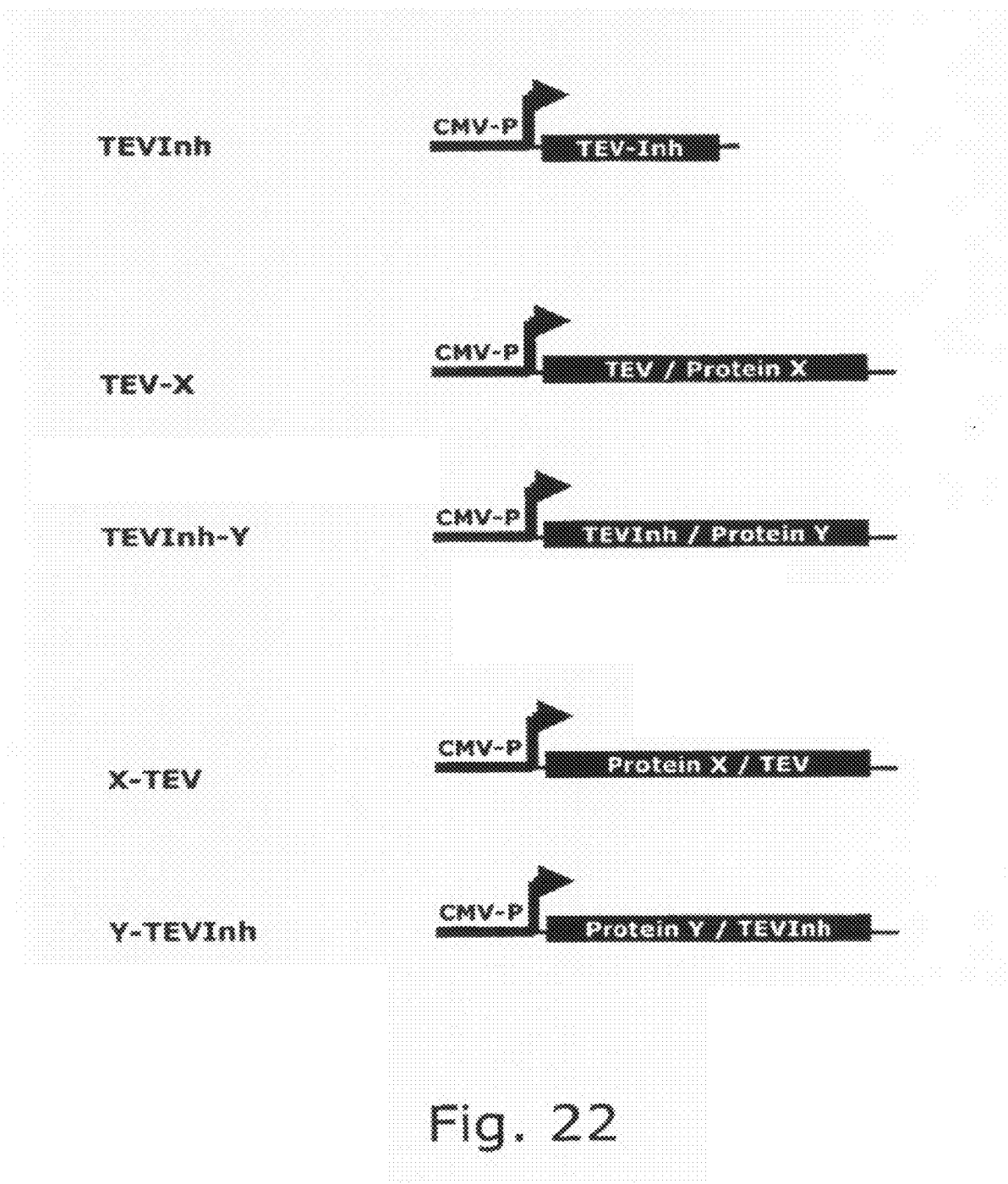
Figure 23:
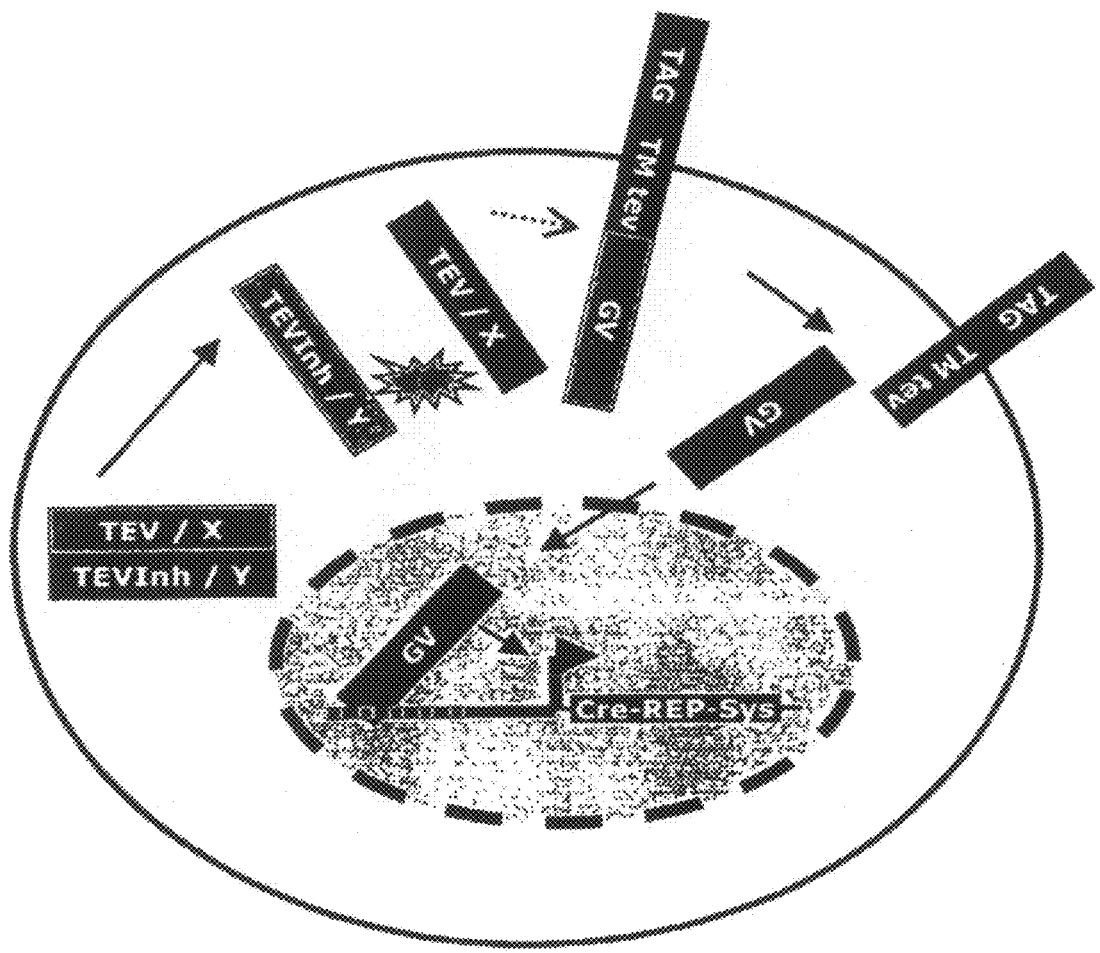
Figure 24:
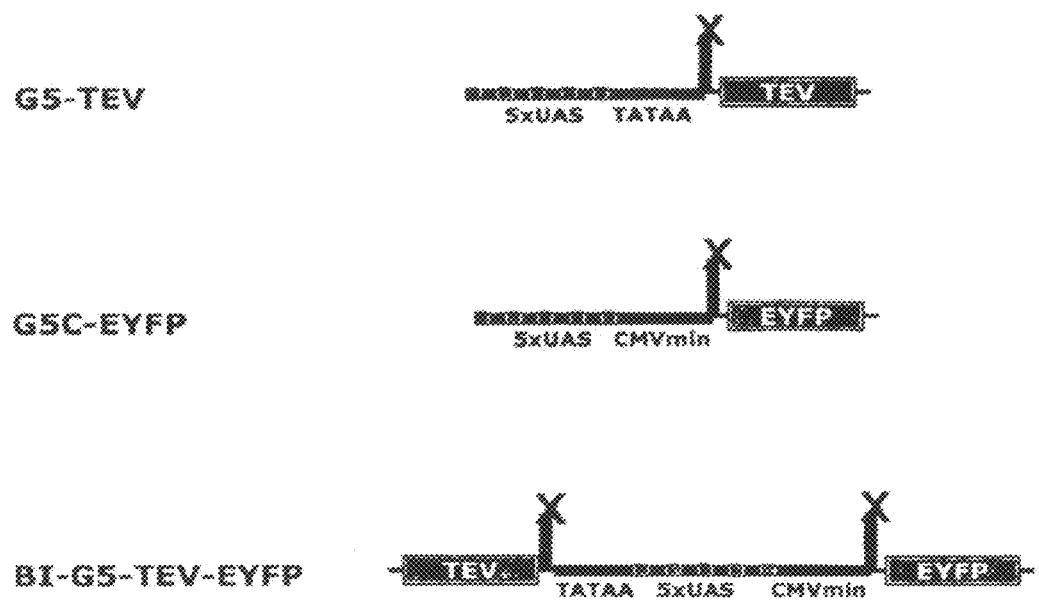
Figure 25:
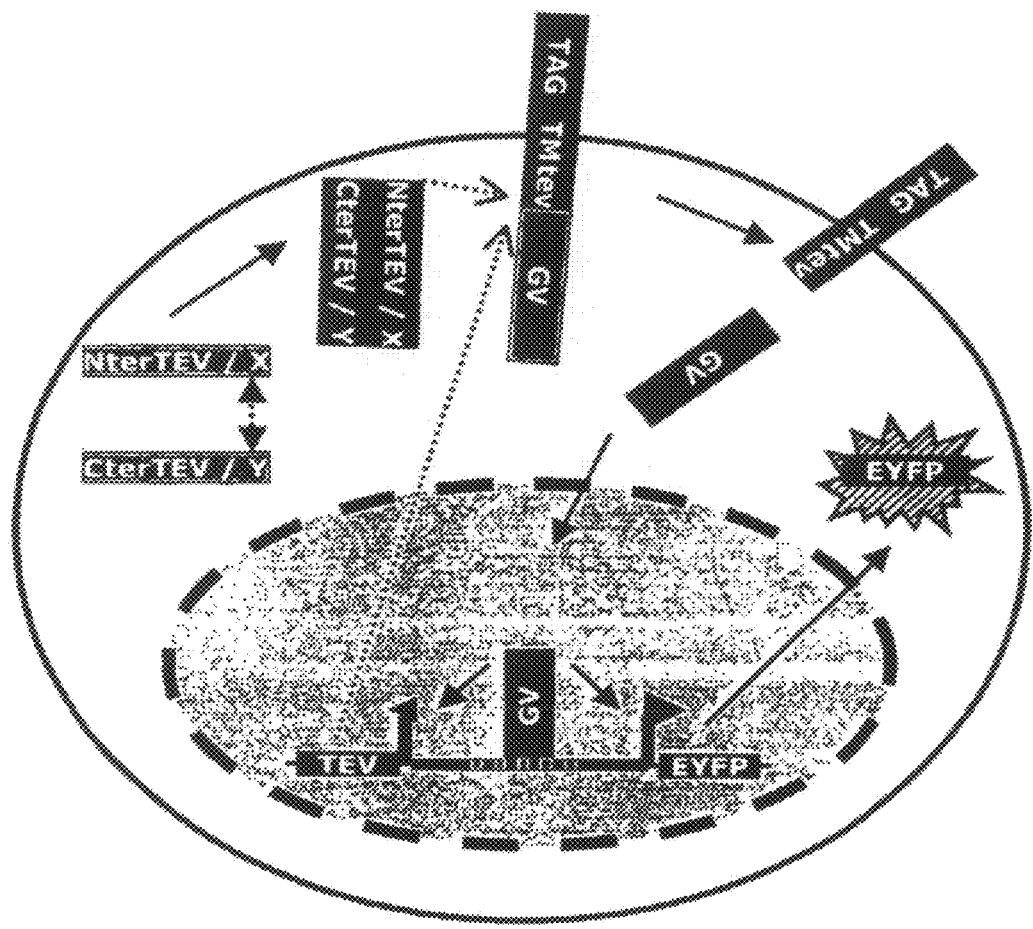

FIG. 12 depicts the evaluation of FACS analysis after transfection of the stable PC12 cell line #20.4 with a vector control, G-CREB, V-CBP/KIX and G-CREB with V-CBP/KIX under control conditions and after forskolin stimulation;

FIG. 13 depicts the diagrammatic representation of the plasmid construct used for the Cre recombinase-coupled two-switch system in mammalian cells;

FIG. 14 depicts a flowchart of the protease-dependent molecular switch for activating a membrane-bound transcription factor;

FIG. 15 depicts the evaluation of FACS analysis after transfection of the stable PC12 cell line #20.4 with a control, GV, TM/Tev, tevGV and TM/Tev with tev/GV;

FIG. 16 depicts the diagrammatic representation of the plasmid construct used for protein interaction-coupled transcomplementation of fragments of TEV protease in mammalian cells;

FIG. 17 depicts a flowchart of the protease-dependent molecular switch for activating a membrane-bound transcription factor after protein interaction-coupled functional reconstitution of the TEV protease fragments;

FIG. 18 depicts the evaluation if FACS analysis after cotransfection of the stable PC12 cell line #20.4 with TMtevGV and with a control, TM-tev-GV, GBR1cc-Cter-TEV-71-243, GBR2cc-CterTEV-1-70;

FIG. 19 depicts the diagrammatic representation of the plasmid constructs used for the protease-coupled endless switch system;

FIG. 20 depicts a flowchart of the protease-dependent molecular switch for activating a proteolytically activatable, nonfluorescent GFP variant, after protein interaction-coupled functional reconstitution of the TEV protease fragments;

FIG. 21 depicts a flowchart of the protease-dependent molecular endless switch for activating a proteolytically activatable, inactive TEV protease and a proteolytically activatable nonfluorescent GFP variant, after protein interaction-coupled functional reconstitution of the TEV protease fragments;

FIG. 22 depicts the diagrammatic representation of the plasmid constructs used for the protease-coupled reverse switch system;

FIG. 23 depicts a flowchart of the reverse switch system after induced dissociation of the known interaction of protein X fused to a TEV inhibitor and protein Y fused to the intact TEV protease, coupled to the two-switch system;

FIG. 24 depicts the diagrammatic representation of the plasmid constructs used for the protease expression feedback-coupled system for endless activation;

FIG. 25 depicts a flowchart of the protein interaction-regulated protease expression feedback-coupled system for endless activation.

DETAILED DESCRIPTION OF THE INVENTION

Figure 1:
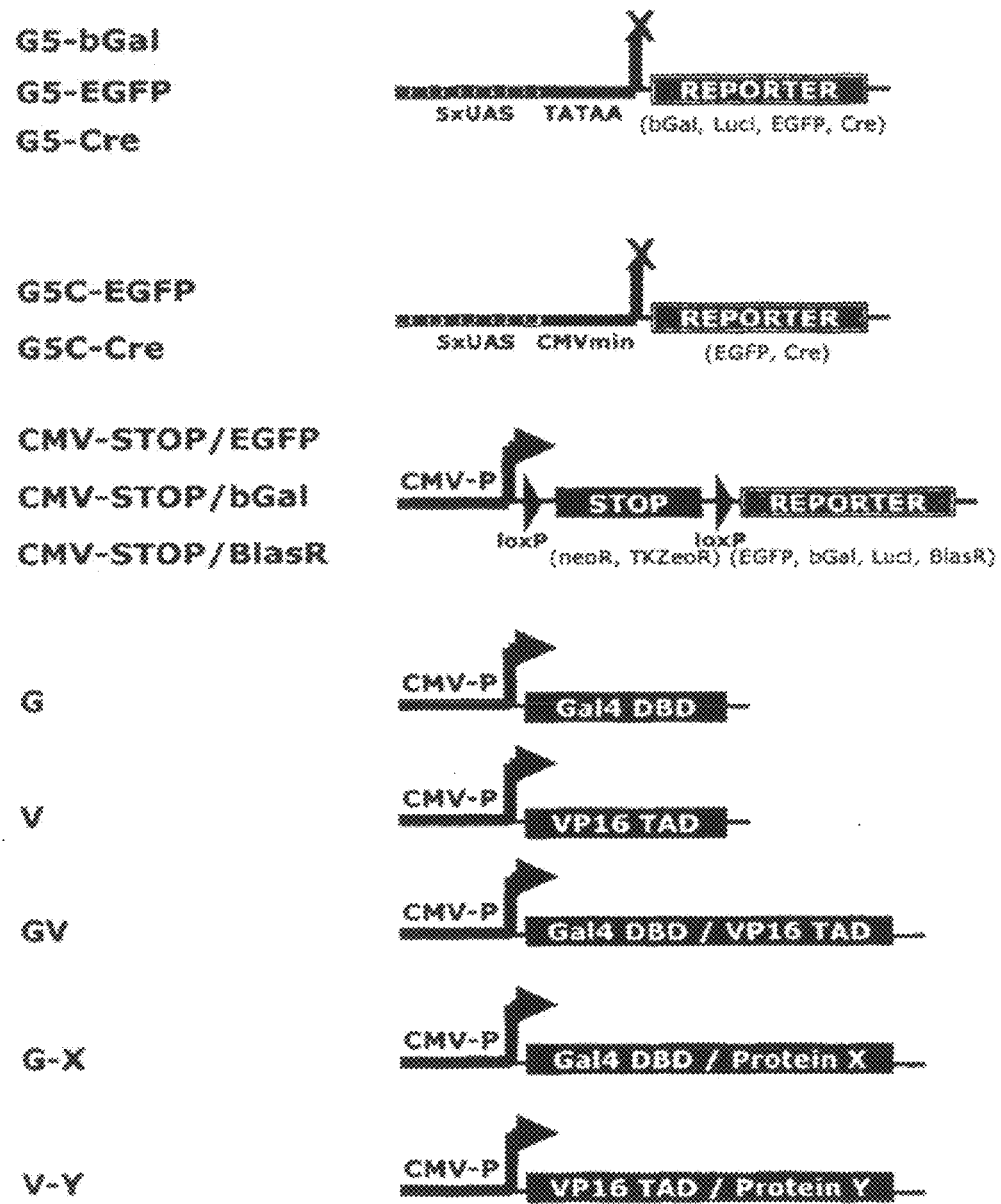

In detail, FIGS. 1 to 25 illustrate the following points and embodiments:

FIG. 1 depicts the diagrammatic representation of the plasmid construct used for the Cre recombinase-dependent two-hybrid system in mammalian cells, with, in detail, the constructs referred to as G5 reporters, G5-bGal, G5-EGFP and G5-Cre, expressing beta-galactosidase, the enhanced green fluorescent protein and Cre recombinase, respectively, under the control of a minimal promoter, the E1B-TATA box, and five successive Gal4-dependent enhancer elements from yeast (upstream activating sequence, UAS);

the constructs referred to as G5C reporters, G5C-EGFP and G5C-Cre, expressing the enhanced green fluorescent protein and Cre recombinase, respectively, under the control of the human CMV minimal promoter (CM-Vmin) and five successive Gal4-dependent enhancer elements from yeast (upstream activating sequence, UAS);

the constructs referred to as CMV-STOP reporters, CMV-STOP/EGFP, CMV-STOP/bGal and CMV-STOP/BlasR, being able to express the enhanced green fluorescent protein, beta-galactosidase and the enzyme conferring resistance to BlasticidinS under the control of a human CMV promoter, if the STOP cassette flanked by loxP sequence elements has been removed after Cre recombinase activity;

the components of the transcription factor used for the two-hybrid system in mammalian cells being depicted.

G refers to the construct for expressing the DNA-binding domain of of the yeast Gal4 transcription factor (Gal4 DBD) under the control of the human CMV promoter.

V refers to the construct for expressing the transcription activation domain of the Herpes simplex virus protein VP16 (VP16 TAD) under the control of the human CMV promoter.

GV refers to the construct for expressing the fusion of the DNA binding domain of the yeast Gal4 transcription factor (Gal4 DBD) and the transcription activation domain of the Herpes simplex virus protein VP16 (VP16 TAD) under the control of the human CMV promoter.

GX refers to the construct for expressing the DNA-binding domain of the yeast Gal4 transcription factor (Gal4 DBD) fused to protein X under the control of the human CMV promoter.

VY refers to the construct for expressing the transcription activation domain of Herpes simplex virus protein VP16 (VP16 TAD) fused to protein Y under the control of the human CMV promoter.

Figure 2:
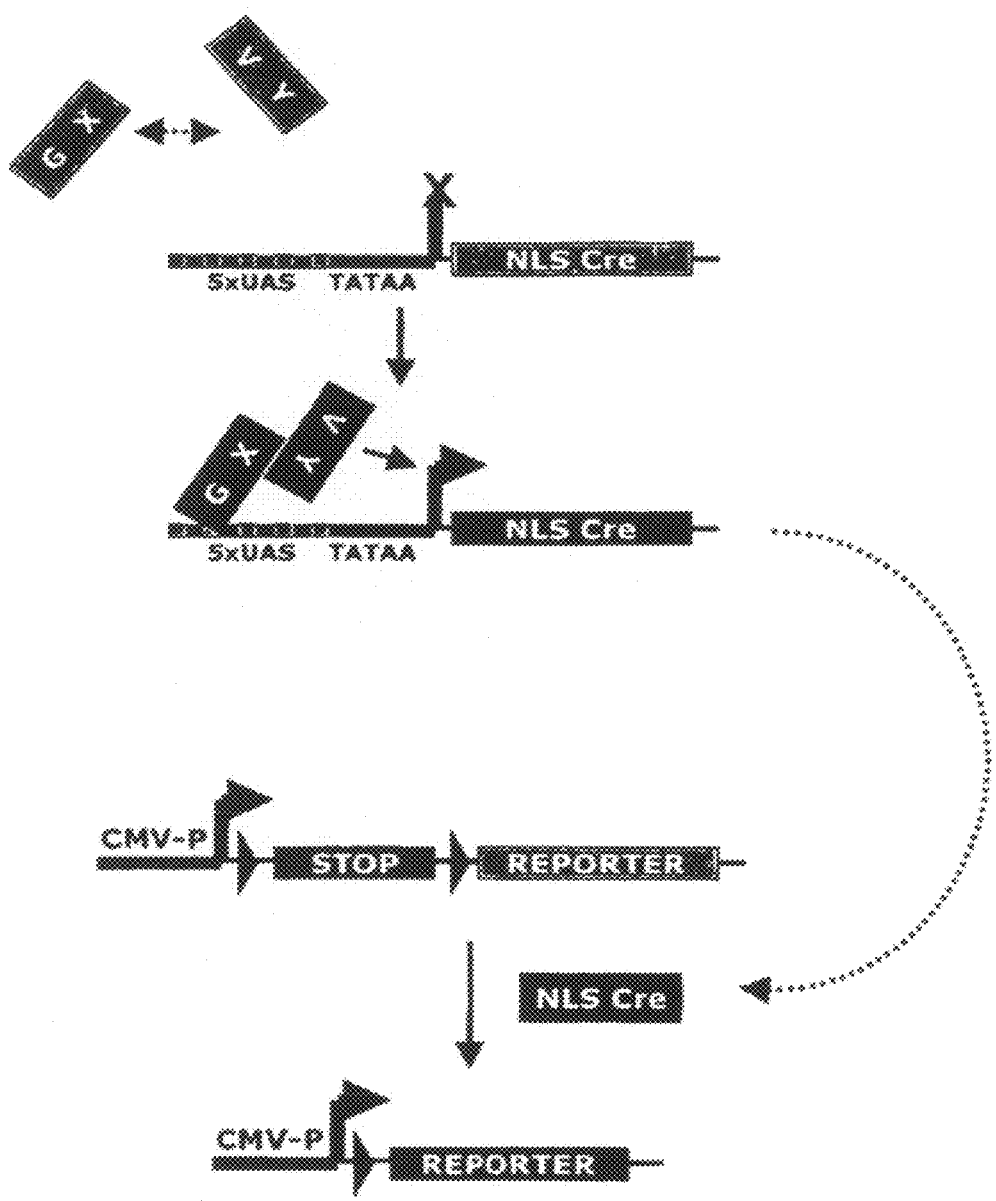

FIG. 2 depicts a flowchart of the Cre recombinase-dependent two-hybrid system for detecting constitutive protein-protein interactions. In the case of a specific interaction of GX and VY which is mediated by the protein domains X and Y, the result is functional reconstitution of a transcription factor which induces Gal4-dependent expression of the Cre recombinase. The activity of the Cre protein which is located in the nucleus results in the removal of the transcriptional inactivation element (STOP) and in permanent activation of downstream reporter genes.

Figure 3:
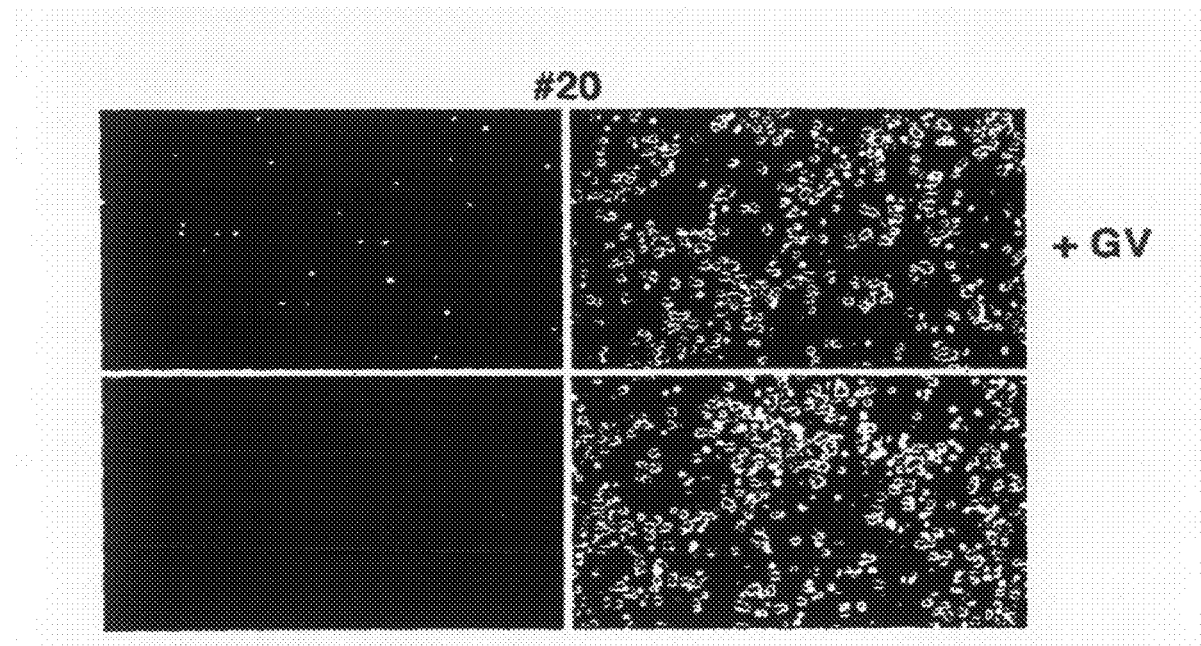

FIG. 3 depicts GFP-fluorescence and phase contrast images of the PC12 cell line #20 after transfection with CMV-STOP/EGFP and transcription factor GV. The cell line #20 contains the construct G5C-Cre in a stably integrated form and shows no EGFP expression after cotransfection with the Cre-dependent reporter construct CMV-STOP/EGFP (bottom left). After cotransfection of CMV-STOP/EGFP with transcription factor GV, a GFP fluorescence can be detected (top left). The phase contrast images (right) depict a comparable number of cells.

Figure 4:
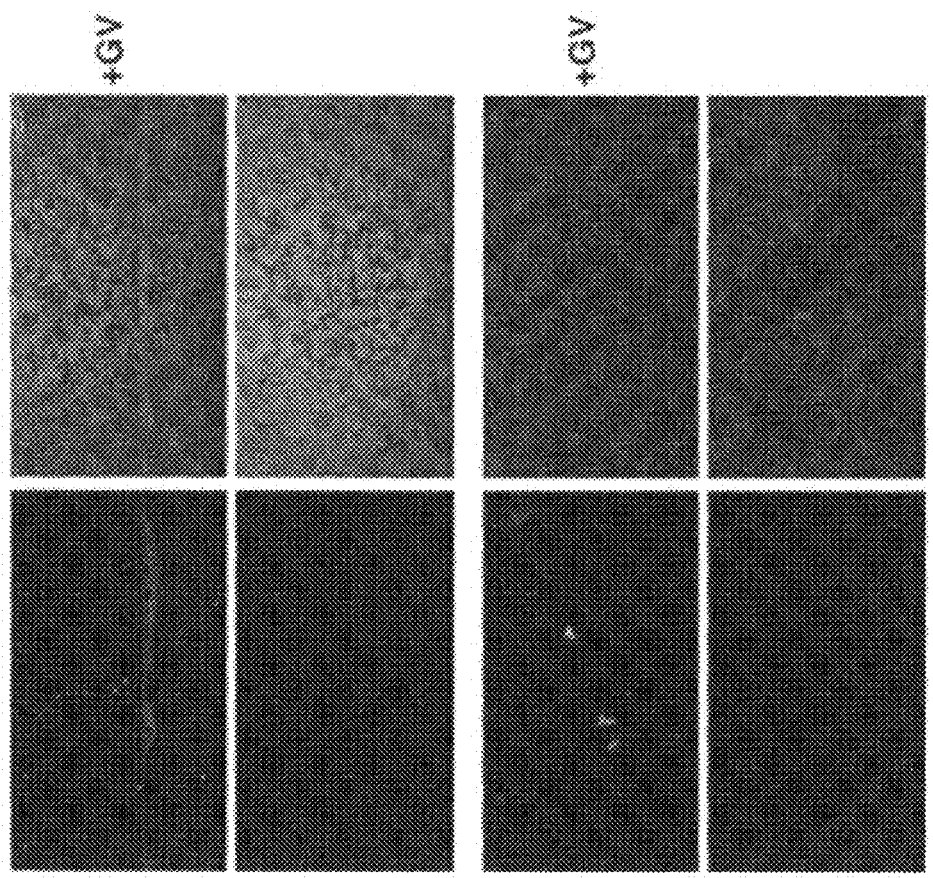

FIG. 4 depicts GFP-fluorescence and phase contrast images of the stable PC12 cell line #20 after transfection with CMV-STOP/EGFP and GV, three days after neuronal differentiation by NGF. The induction of neuronal differentiation and, connected therewith, prevention of further cell divisions have no influence on the activation of Cre recombinase-mediated GFP fluorescence after cotransfection of CMV-STOP/EGFP with transcription factor GV in the PC12 cell line #20 (top left). The GFP-positive cells depicted under higher magnification show the neuronal morphology (bottom left).

Figure 5:
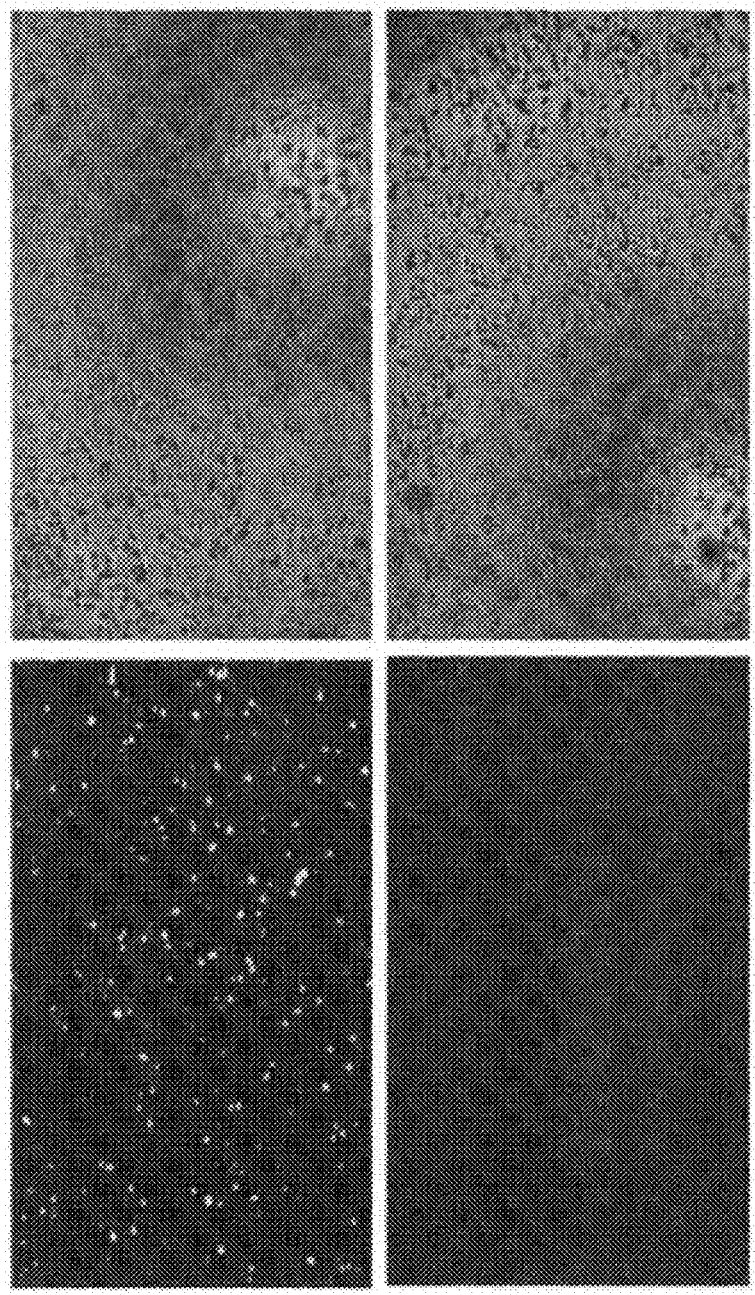

FIG. 5 depicts GFP-fluorescence and phase contrast images of the stable PC12 cell line #20.4 after transfection with GV. The cell line #20.4 contains the constructs G5C-Cre, CMV-STOP/EGFP and CMV-TkZeo/BlasR in a stably integrated form and shows GFP fluorescence only after transfection of transcription factor GV (top left). Under control conditions, no GFP fluorescence is detectable (bottom left). The phase contrast images depict a comparable number of cells (right).

Figure 6:
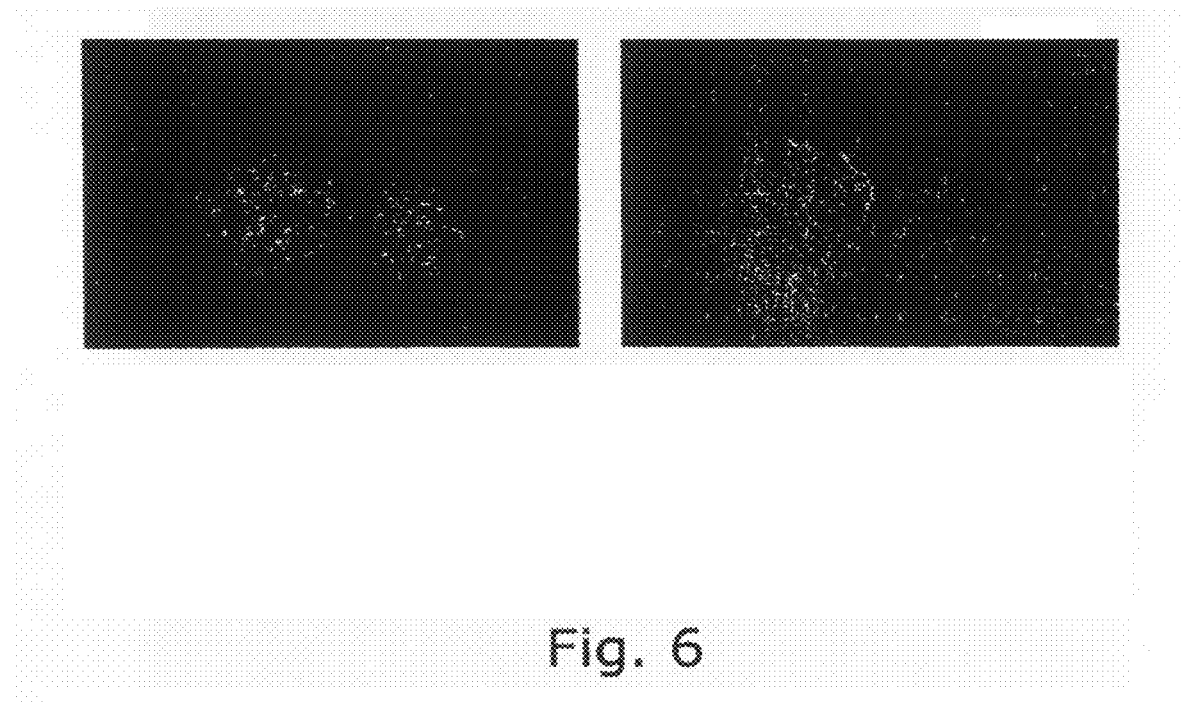

FIG. 6 depicts GFP-fluorescence and phase contrast images of the stable PC12 cell line #20.4 after transfection with GV and BlasticidinS selection for four weeks. All cells of the BlasticidinS-resistant cell clones show a comparable GFP fluorescence, all resistant cell clones are GFP-positive.

Figure 7:
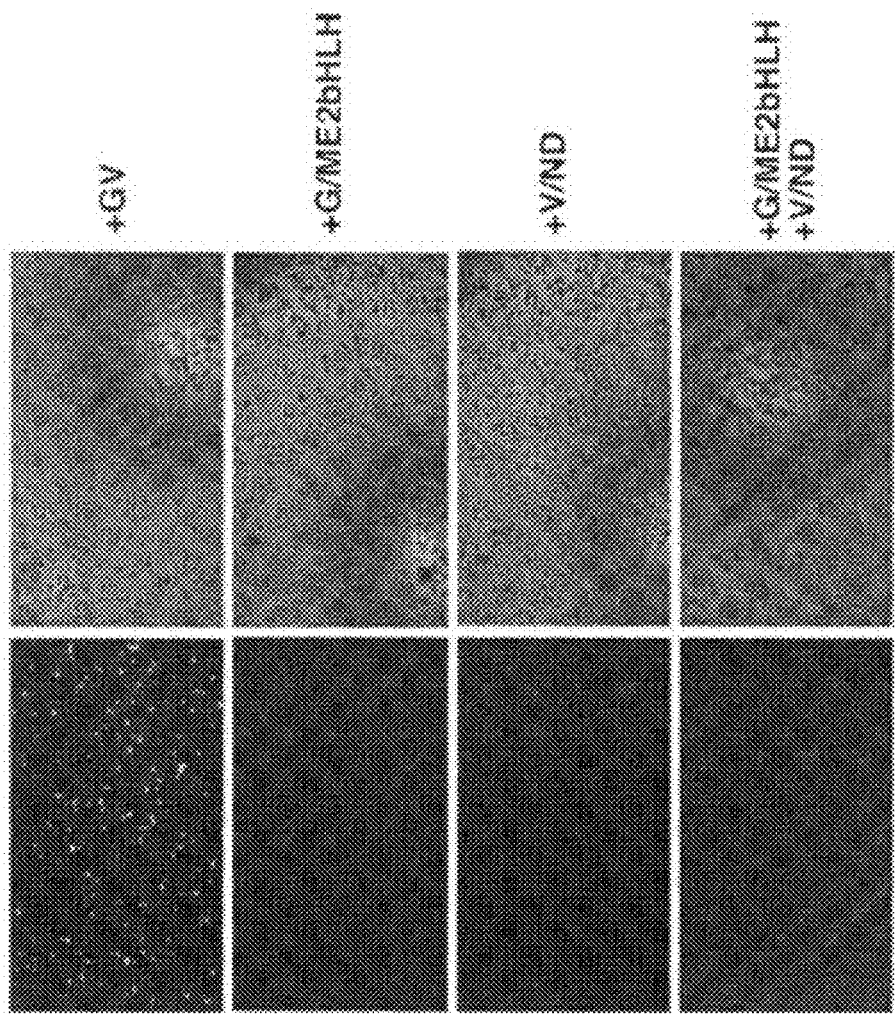

FIG. 7 depicts GFP-fluorescence and phase contrast images of the stable PC12 cell line #20.4 two days after transfection with GV, G-ME2bHLH, V-ND and G-ME2bHLH with V-ND. The cell line #20.4 shows GFP fluorescence only after transfection of transcription factor GV (top left). After cotransfection of the two-hybrid interaction partners V-ND and G-ME2bHLH, no GFP-fluorescence is detectable (bottom left). Under control conditions, transfection of V-ND or G-ME2bHLH, likewise no GFP fluorescence is detectable (center left). The phase contrast images depict a comparable number of cells (right).

Figure 8:
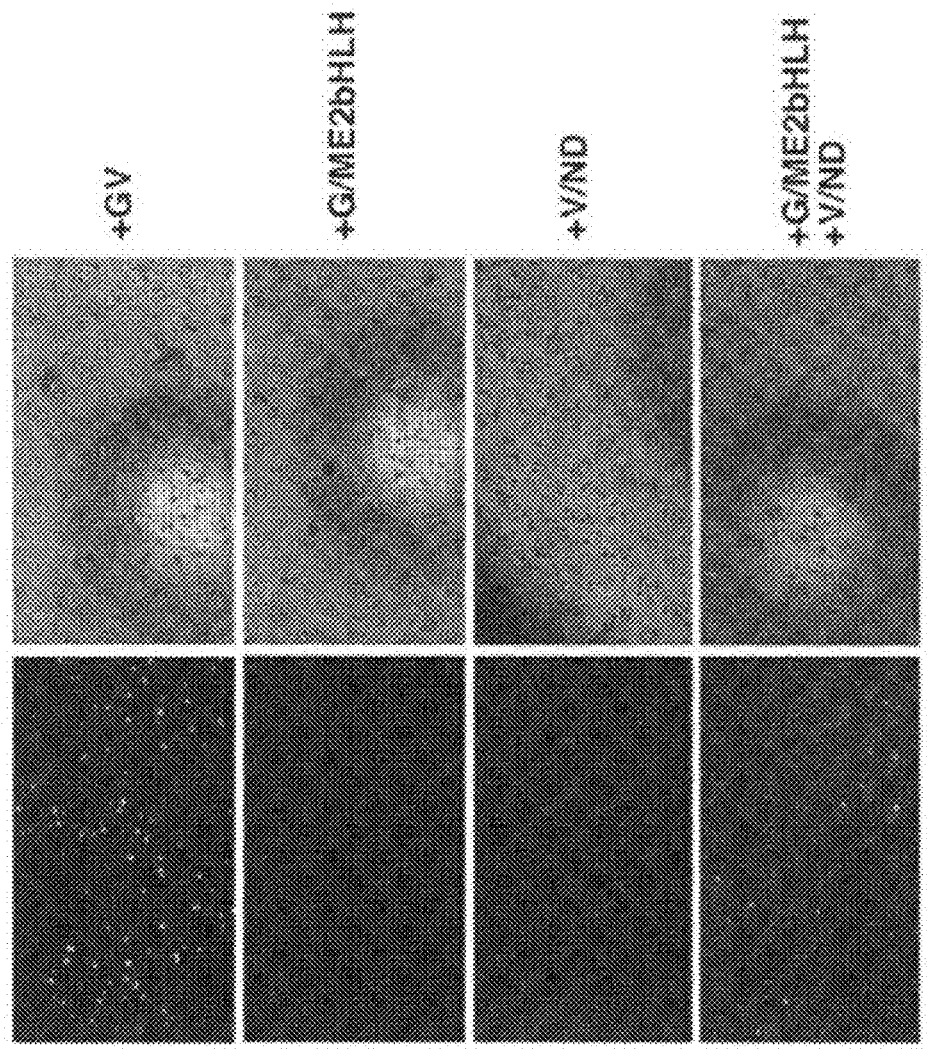

FIG. 8 depicts GFP-fluorescence and phase contrast images of the stable PC12 cell line #20.4 two days after transfection with GV, G-ME2bHLH, V-ND and G-ME2bHLH with V-ND, with addition of TSA. After transfection of transcription factor GV, the cell line #20.4 shows GFP fluorescence (top left). After cotransfection of the two-hybrid interaction partners V-ND and G-ME2bHLH, GFP fluorescence is likewise detectable under the TSA culturing conditions (bottom left). Under control conditions, transfection of V-ND or G-ME2bHLH, no GFP fluorescence is detectable (center left). The phase contrast images depict a comparable number of cells (right).

Figure 9:
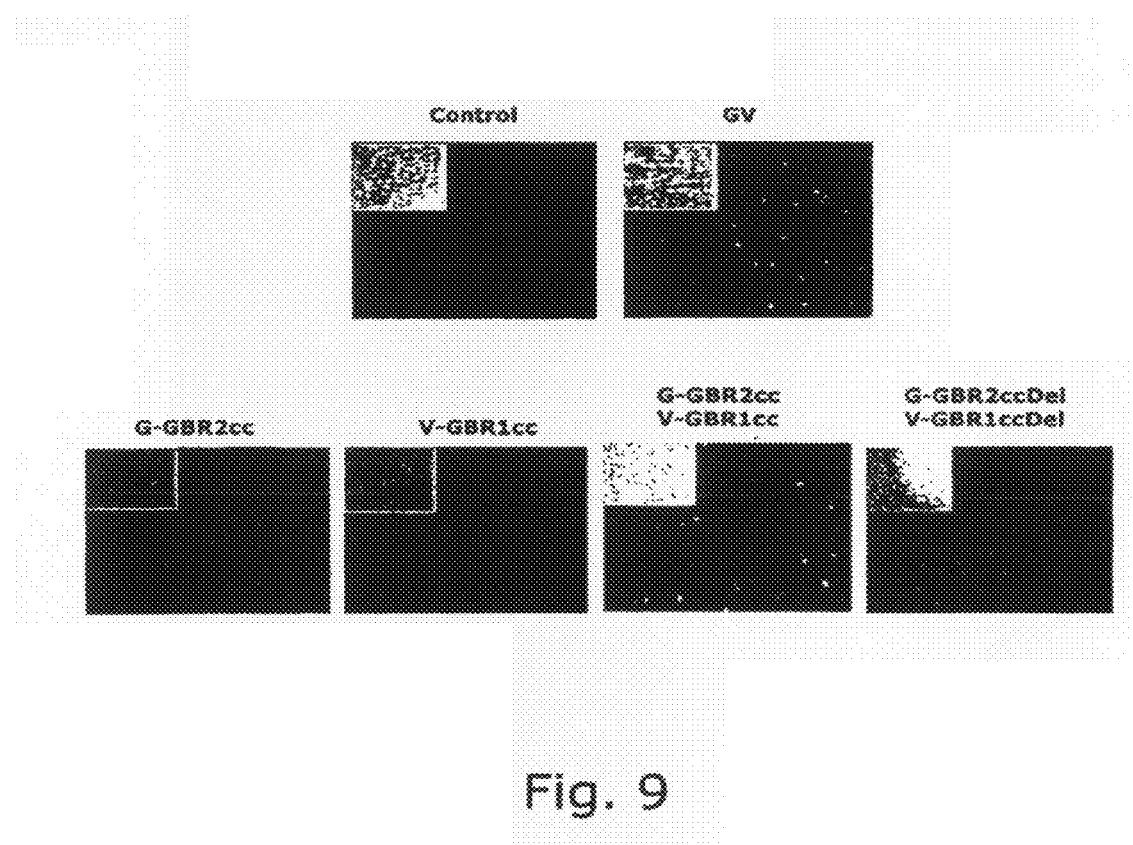

FIG. 9 depicts GFP fluorescence and phase contrast images (small inset image) of the stable PC12 cell line #20.4 after transfection with GV, G-GBR2cc, V-GBR1cc, G-GBR2cc with V-GBR1cc and G-GBR2ccDel with V-GBR1ccDel. After transfection of transcription factor GV the cell line #20.4 shows GFP fluorescence (top right). After cotransfection of the two-hybrid interaction partners G-GBR2cc, V-GBR1cc, GFP fluorescence is likewise detectable (bottom left). Under control conditions, transfection of an empty vector (control, top left) and of the individually transfected interaction partners (G-GBR2cc or V-GBR1cc, bottom left), no GFP fluorescence is detectable (center left). After cotransfection of plasmids coding for coiled-coiled deletion mutants of the intracellular domains of GBR1 and GBR2, likewise no GFP fluorescence is detectable (G-GBR2ccDel and V-GBR1ccDel, bottom inside right). The phase contrast images depict a comparable number of cells (small inset figure).

Figure 10:
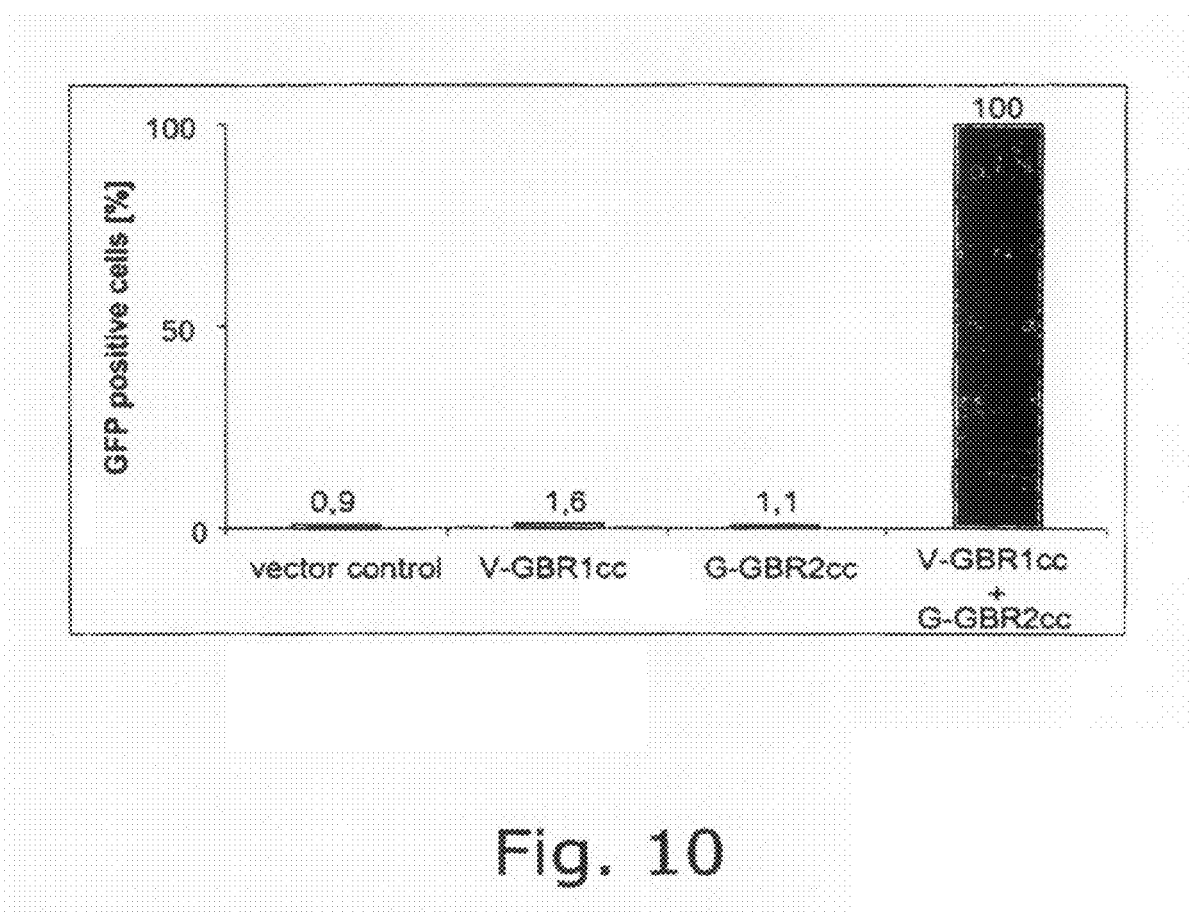

FIG. 10 depicts the quantitative evaluation of FACS analysis of the stable PC12 cell line #20.4 two days after transfection with GV, V-GBR1cc, G-GBR2cc and V-GBR1cc together with G-GBR2cc, depicted as the relative number of GFP-positive cells. Two days after cotransfection of the interaction partners G-GBR2cc and V-GBR1cc, about 100 times more GFP-positive cells can be detected in comparison with the controls, empty vector (vector control) and the individual transfections of G-GBR2cc and V-GBR1cc.

Figure 11:
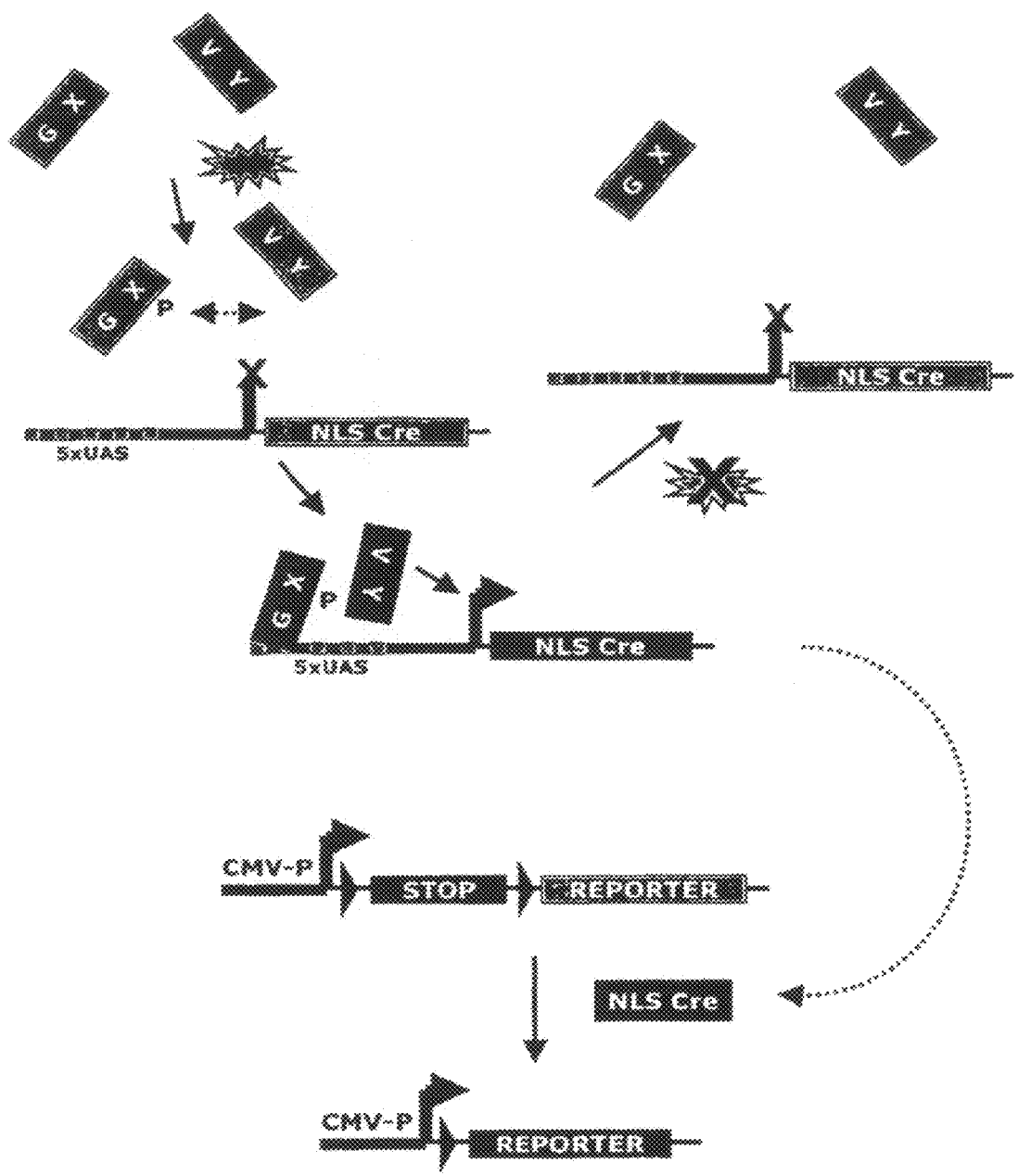

FIG. 11 depicts a flowchart of the Cre recombinase-dependent two-hybrid system for detecting induced and transient protein-protein interactions. In the case of a stimulus-dependent interaction of GX and VY which is mediated by the protein domains X and Y, the result is the functional reconstitution of a transcription factor inducing Gal4-dependent expression of the Cre recombinase. The stimulus is represented by the explosion symbol. The stimulation-dependent modification of protein section X is indicated by P. After removal of the cellular modification (represented by the X above the explosion symbol), the modification and the protein interaction are removed. The activity of the Cre protein which is located in the nucleus results in removal of the transcriptional inactivation element (STOP) and in permanent activation of downstream reporter genes. The activity of the Cre protein may be transient and needs to reach a particular threshold only once.

FIG. 12 depicts the results of FACS analysis three days after transfection of the stable PC12 cell line #20.4 with a vector control, G-CREB, V-CBP/KIX and G-CREB with V-CBP/KIX, with or without forskolin stimulation. The cumulated GFP fluorescence (top) and the relative number of GFP-positive cells (bottom) without forskolin stimulation (framed columns) and after transient forskolin stimulation (black columns) are depicted. After cotransfection of the interaction partners, G-CREB with V-CBP/KIX, the number of detected GFP-positive cells is increased about 12 times after forskolin stimulation. The increase in total fluorescence of the GFP-positive cells is twenty times higher than the unstimulated control. Transfection with V-CBP-KIX shows virtually no background, while transfection with the G-CREB construct has GFP background both in the unstimulated and in the forskolin-stimulated reaction mixture. The likewise strong increase in GFP fluorescence after forskolin stimulation presumably reflects the interaction with endogenously present CBP-like transcriptional cofactors.

FIG. 13 depicts the diagrammatic representation of the plasmid constructs used for the Cre recombinase-coupled two-switch system in mammalian cells. SS refers to the signal sequence, TAG is the extracellular domain encompassing specific epitopes, TM is the PDGF-alpha receptor transmembrane domain. The constructs are described in closer detail:

the construct referred to as renin expresses the human renin protease under the control of the human CMV promoter.

the construct referred to as TEV expresses the NIa protease of tobacco etch virus (TEV protease) under the control of the human CMV promoter.

the construct referred to as TM/TEV expresses a transmembrane-bound form of the TEV protease of the tobacco etch virus under the control of the human CMV promoter.

the construct referred to as TM/S/TEV expresses a transmembrane-bound form of the TEV protease of the tobacco etch virus under the control of the human CMV promoter, said TEV protease being separated from the transmembrane domain by a peptide section (S stands for spacer).

the construct referred to as TM/GV expresses a transmembrane-bound inactive form of the transcription activator GV under the control of the human CMV promoter.

the construct referred to as TM/ren/GV expresses a transmembrane-bound inactive form of the transcription activator GV under the control of the human CMV promoter, said transcription activator GV being separated from the transmembrane domain by a peptide section ren. ren represents a human renin protease-specific recognition and cleavage sequence.

the construct referred to as TM/tev/GV expresses a transmembrane-bound inactive form of the transcription activator GV under the control of the human CMV promoter, said transcription activator GV being separated from the transmembrane domain by a peptide section tev. tev represents a recognition and cleavage sequence specific for the TEV protease.

the construct referred to as TM/Cre expresses a transmembrane-bound inactive form of Cre recombinase under the control of the human CMV promoter.

the construct referred to as TM/ren/Cre expresses a transmembrane-bound inactive form of Cre recombinase under the control of the human CMV promoter, said Cre recombinase being separated from the transmembrane domain by a peptide section ren. ren represents a recognition and cleavage sequence specific for the human renin protease.

the construct referred to as TM/tev/Cre expresses a transmembrane-bound inactive from of Cre recombinase under the control of the human CMV promoter, said Cre recombinase being separated from the transmembrane domain by a peptide section tev. tev represents a recognition and cleavage sequence specific for the TEV protease.

the construct referred to as TM/EYFP expresses a transmembrane-bound form of enhanced yellow fluorescent protein (EYFP) with C-terminal nuclear localization signals (NLS) under the control of the human CMV promoter.

the construct referred to as TM/ren/EYFP expresses a transmembrane-bound form of enhanced yellow fluorescent protein (EYFP) with C-terminal nuclear localization signals (NLS) under the control of the human CMV promoter, said EYFP-NLS protein being separated from the transmembrane domain by a peptide section ren. ren represents a recognition and cleavage sequence specific for the human renin protease.

the construct referred to as TM/tev/EYFP expresses a transmembrane-bound form of enhanced yellow fluorescent protein (EYFP) with C-terminal nuclear localization signals (NLS) under the control of the human CMV promoter, said EYFP-NLS protein being separated from the transmembrane domain by a peptide section tev. ren represents a recognition and cleavage sequence specific for the human renin protease.

FIG. 14 depicts a flowchart of the TEV protease-dependent molecular switch for activating a membrane-bound transcription factor and subsequent activation of a reporter or reporter system. Coexpression of the TEV protease with a transmembrane-bound transcription factor (GV) which N-terminally has a TEV protease-specific recognition and cleavage site (tev) results in the cleavage and subsequent translocalization of transcription factor GV into the nucleus. GV-dependent reporter genes or reporter systems are activated.

FIG. 15 depicts the quantitative evaluation of FACS analysis two days after transfection of the stable PC12 cell line #20.4 with a control vector (control), GV, TM/Tev, tevGV and TM/Tev together with tev/GV. The relative number of GFP-positive cells in comparison with transfection with the soluble transcription factor GV is shown. The number of detected cells after single transfection with the empty vector, with the transmembrane-bound TEV or with the transmembrane-bound GV is below 1%. After cotransfection of the transmembrane-bound TEV with the transmembrane-bound transcription factor GV, the soluble GV can detect on average half of GFP-positive cells, in comparison with transfection under comparative conditions.

FIG. 16 depicts the diagrammatic representation of the plasmid constructs used for protein interaction-coupled transcomplementation of fragments of the TEV protease in mammalian cells, with, in detail, the construct referred to as NterTEV expressing an N-terminal fragment of the TEV protease of tobacco etch virus under the control of the human CMV promoter, the construct referred to as CterTEV expressing an N-terminal fragment of the TEV protease of tobacco etch virus under the control of the human CMV promoter, the construct referred to as NterTEV-X expressing an N-terminal fragment of the TEV protease of tobacco etch virus as fusion protein with the N terminus of a protein X under the control of the human CMV promoter, the construct referred to as CterTEV-Y expressing a C-terminal fragment of the TEV protease of tobacco etch virus as fusion protein with the N terminus of a protein Y under the control of the human CMV promoter, the construct referred to as X-NterTEV expressing an N-terminal fragment of the TEV protease of the tobacco etch virus as fusion protein with the C terminus of a protein X under the control of the human CMV promoter, the construct referred to as Y-CterTEV expressing a C-terminal fragment of the TEV protease of the tobacco etch virus as fusion protein with the C terminus of a protein Y under the control of the human CMV promoter.

FIG. 17 depicts a flowchart of the protease-dependent molecular switch for activating a membrane-bound transcription factor after protein interaction-coupled functional reconstitution of TEV protease fragments. After coexpression of plasmids which, on the one hand, code for an N-terminal TEV fragment-protein X fusion protein and for a C-terminal TEV fragment-protein Y fusion protein, the proteolytic activity is functionally reconstituted in the case of the specific interaction of the proteins or protein sections X and Y. This is followed by a stably expressed or transiently cotransfected membrane-bound transcription factor (GV) which contains a TEV-specific recognition and cleavage sequence (tev) being detached from the membrane. The result is translocalization of GV into the nucleus and activation of a reporter gene or reporter system.

FIG. 18 Part A depicts the quantitative evaluation of FACS analysis two days after transfection of the stable PC12 cell line #20.4 with an expression vector coding for the membrane-bound transcription factor GV containing an N-terminal TEV-specific recognition and cleavage sequence (TM-tev-GV). The cumulated fluorescence relative to the activity of the membrane-bound TEV protease is shown in %. Expression vectors were cotransfected with TMtevGV, which code for:

control: membrane-bound TEV (TM-TEV), a membrane-bound GBR1cc domain fused to a C-terminal TEV protease fragment, from amino acid 71-243 (GBR1cc-CterTEV-71-243), a membrane-bound GBR2cc domain fused to an N-terminal TEV protease fragment, from amino acid 1-70 (GBR2cc-CterTEV-1-70) and a membrane-bound GBR1cc domain fused to a C-terminal TEV protease fragment, from amino acid 71-243 (GBR1cc-CterTEV-71-243) together with a membrane-bound GBR2cc domain fused to an N-terminal fragment of said TEV protease, from amino acid 1-70 (GBR2cc-CterTEV-1-70).

After cotransfection of the TEV fragments as fusion proteins of the interaction domains GBR2cc and GBR1cc about 30% of the activity of the membrane-bound TEV protease is obtained.

B depicts combinations of further TEV fragments fused to the coiled-coil interaction domains of GBR1 and GBR2. The constructs were cotransfected into PC12 cells with the membrane-anchored TM-tev-GV, a plasmid transcriptionally activatable by GV and coding for Cre recombinase, and a reporter plasmid coding for firefly luciferase under the control of a strong promoter. However, transcription of said luciferase was interrupted by a stop cassette located between gene and promoter and flanked by pLox. The system was activated by specific transcomplementation of the TEV protease, ultimately leading to production of luciferase at the end of the cascade. The bar diagram depicts this activity in RLU (relative luminescence units) and compares it with the signal of the intact protease.

FIG. 19 depicts the diagrammatic representation of the plasmid constructs used for the protease-coupled endless switch system, with, in detail, the construct referred to as TtevEV being an inactive TEV protease under the control of the human CMV promoter. Insertion of a peptide sequence containing at least one TEV-specific recognition and cleavage sequence renders this modified TEV protease inactive. After specific proteolytic cleavage by an active TEV protease, the modified TEV protease TtevEV is activated, the construct referred to as EYtevFP being an inactive, nonfluorescent enhanced green fluorescent protein (EYFP) under the control of the human CMV promoter. Insertion of a peptide sequence containing at least one TEV specific recognition and cleavage sequence renders this modified EYFP inactive. The modified EYtevFP is activated after specific proteolytic cleavage by an active TEV protease.

FIG. 20 depicts a flowchart of the protease-dependent molecular switch for activating a proteolytically activatable nonfluorescent EYFP variant after protein interaction-coupled functional reconstitution of TEV protease fragments. After coexpression of plasmids which, on the one hand, code for an N-terminal TEV fragment-protein X fusion protein and for a C-terminal TEV fragment-protein Y fusion protein, the proteolytic activity is functionally reconstituted in the case of specific interaction of the proteins or protein sections X and Y. A stably expressed or transiently cotransfected inactive, proteolytically activatable reporter protein, such as, for example, an appropriately modified EYFP (EY-tev-FP), is then specifically proteolytically cleaved and activated.

FIG. 21 depicts a flowchart of the protease-dependent molecular endless switch for activating a proteolytically activatable, inactive TEV protease and a proteolytically activatable, nonfluorescent GFP variant after protein interaction-coupled functional reconstitution of TEV protease fragments. After coexpression of plasmids which, on the one hand, code for an N-terminal TEV fragment-protein X fusion protein and for a C-terminal TEV fragment-protein Y fusion protein, the proteolytic activity is functionally reconstituted in the case of specific interaction of the proteins or protein sections X and Y. A stably expressed or transiently cotransfected inactive, proteolytically activatable TEV protease (TtevEV) is then specifically proteolytically cleaved and permanently activated. Subsequently, a stably expressed or transiently cotransfected inactive, proteolytically activatable reporter protein such as, for example, an appropriately modified EYFP (EY-tev-FP) is specifically proteolytically cleaved and activated. Activation of the constitutively expressed proteolytically activatable functional elements results in a molecular endless loop.

FIG. 22 depicts the diagrammatic representation of the plasmid constructs used for the protease-coupled reverse switch system, with, in detail, the construct referred to as TEVInh expressing a protein inhibitor or peptide inhibitor of the TEV protease of tobacco etch virus under the control of the human CMV promoter.

the construct referred to as TEV-X expressing a fusion protein of the intact TEV protease of tobacco etch virus and a protein X under the control of the human CMV promoter. The protein X is fused to the C terminus of the TEV protease.

the construct referred to as TEVInh-Y expressing a fusion protein of a TEV inhibitor and a protein Y under the control of the human CMV promoter. The protein Y is fused to the C terminus of the TEV inhibitor.

the construct referred to as X-TEV expressing a fusion protein of the intact TEV protease of tobacco etch virus and a protein X under the control of the human CMV promoter. The protein X is fused to the N terminus of the TEV protease.

the construct referred to as Y-TEVInh expressing a fusion protein of a TEV inhibitor and a protein Y under the control of the human CMV promoter. The protein Y is fused to the N terminus of the TEV inhibitor.

FIG. 23 depicts a flowchart of the reverse switch system after induced dissociation of the known interaction of protein X fused to a TEV inhibitor and of protein Y fused to the intact TEV protease, coupled to the two-switch system. The protein X and protein Y-mediated interaction of the TEV inhibitor with the intact TEV protease results in inactivation of the TEV protease. After induced removal of the interaction, represented by the explosion symbol, the TEV protease is activated. The downstream reporter system depicted here is the two-switch system (see FIG. 14).

FIG. 24 depicts the diagrammatic representation of the plasmid constructs used for the protease expression feedback-coupled system for endless activation, with, in detail, the constructs referred to as G5-TEV expressing the TEV protease under the control of a minimal promoter, the E1B-TATA box, and five successive Gal4-dependent enhancer elements from yeast (upstream activating sequence, UAS).

the constructs referred to as G5C-TEV expressing the TEV protease under the control of the human CMV minimal promoter, and five successive Gal4-dependent enhancer elements from yeast (upstream activating sequence, UAS).

FIG. 25 depicts a flowchart of the protein interaction-regulated protease expression feedback-coupled system for endless activation. After coexpression of plasmids which, on the one hand, code for an N-terminal TEV fragment-protein X fusion protein and for a C-terminal TEV fragment-protein Y fusion protein, the proteolytic activity is functionally reconstituted in the case of specific interaction of the proteins or protein sections X and Y. A stably expressed or transiently cotransfected membrane-bound transcription factor (GV) containing a TEV-specific recognition and cleavage sequence (tev) is then detached from the membrane. The result is a translocalization of GV into the nucleus and activation of two coregulated or independent reporter genes one of which is the intact TEV protease. The GV-regulated expressed TEV protease results in further cleavage of the constitutively expressed TM-tev-GVs and results in permanent activation of the complete reporter system.

The following examples describe the individual embodiments of the method of the invention in more detail.

All molecular cloning and transfections were carried out using standard protocols according to Sambrook et al (Sambrook-J and Russell-D W 2001).

Example 1

Preparation of the Plasmid Vectors of the Cre Recombinase-Based Reporter System

The functional elements of the plasmid vectors for carrying out the Cre recombinase-based reporter system and the application in the two-hybrid system in mammalian cells are diagrammatically depicted in FIG. 1.

Construction of the reporter plasmids: the plasmid G5-CAT carries, 5' of the chloramphenicol transferase (CAT) reporter gene, the TATAA box of the human E1B gene and five successive enhancer elements (upstream activating sequence, UAS) having the optimal recognition sequence for the *Saccharomyces cerevisiae* Gal4 transcription factor. The G5-CAT plasmid DNA served as starting vector for preparing the G5 reporters used and was cut using combinations of restriction enzymes in such a way that it was possible to remove the CAT gene 5' and 3' from the vector backbone and to insert the appropriately prepared reporter gene DNA fragments. For this purpose, the Cre recombinase of bacteriophage P1 (Cre) was amplified by the polymerase chain reaction (PCR) using specific oligonucleotides and modified 5' by a start codon flanked by the Kozak sequence (Kozak 1989) (Kozak 1987). The plasmid vectors G5C-EGFP and G5C-Cre were cloned using the plasmids tetO-EGFP and tetO-Cre and G5-Cat as backbone. The E1B-TATAA box and the CAT reporter were removed and replaced with the human cytomegalievirus (CMV) minimal promotor and the corresponding reporter gene.

Coding regions of the DNA binding domain (DBD) of the yeast transcription factor Gal4 and of the transactivation domain (TAD) of the Herpes simplex protein VP16 were amplified by means of PCR from corresponding yeast two-hybrid vectors and cloned into the eukaryotic expression vectors pCMV. The oligonucleotides were designed so as to introduce 5' a restriction cleavage site and a Kozak sequence-flanked ATG and for the last codon 3' to be in the reading frame with another introduced restriction cleavage site without stop codon. Stop codons of the three possible reading frames are located in the vector pCMV 3' of the multiple cloning sequences (MCS) so that it was possible to utilize the vectors pCMV-Gal4 DBD (G) and pCMV-VP16 TAD (V) (see FIG. 1) as starting vectors for C-terminal fusions with further proteins or protein sections. The vector GV which codes for a fusion protein of Gal4 DBD and VP16 TAD was prepared starting from the pCMV-Gal4 plasmid vector and the PCR product coding for V16 TAD, taking into account a continuous reading frame (see FIG. 1).

The Cre-activatable CMV-STOP/REPORTER constructs were prepared by sequential cloning into pCMV. First, the STOP cassettes were generated by PCR, incorporating in each case two loxP sites (recognition and recombination elements of Cre recombinase) in the same orientation 5' and 3' of a neomycin resistance- and of a zeocin-resistance-conferring element (neoR and TKZeoR, see FIG. 1). The corresponding reporter gene downstream of Cre was then cloned in 3' of the STOP cassette. EGFP and bGal were introduced 3' of the neoR STOP cassette and an element conferring resistance to BlasticidinS was introduced 3' of the TKZeoR STOP cassette. The functionality of the STOP-REPORTER cassettes was analyzed via transient transfections in Cos7 cells. For this purpose, said cassettes were cotransfected together with a control vector or with a CMV-Cre plasmid vector, it being possible to observe the activity of the downstream reporters, EGFP, bGal and BlasR, only after cotransfection with CMV-Cre.

Example 2

Functional Analysis of the Components of the Cre Recombinase-Based Reporter System via Transient Transfection into PC12 and Cos7 Cells The reporter plasmids or combinations of reporter plasmids were tested via transient transfections into the PC12 and Cos7 cell lines. For this purpose, between $10^5$ and $10^6$ PC12 or Cos7 cells were electroporated using a GenePulser II with Capacity Extender module (BioRad, Munich, Germany). Plasmid DNA was purified using the Qiafilter method (Qiagen, Hilden, Germany). For each electroporation, a total of 5 µg of plasmid DNA was always used, filling up with plasmid DNA of an empty vector, depending on the reaction mixture. The electroporation was carried out in special cuvettes (PeqLab) in the appropriate cell growth medium and using the following parameters: Cos7 cells, $10^5$ cells in 300 µl per reaction mixture, pulses with 250 mV at 500 µF; PC12 cells, $10^6$ cells in 300 µl per reaction mixture, pulses of 220 mV at 960 µF. After electroporation, the cells were transferred to 6 cm or 24 well cell culture dishes and cultured. Analysis was carried out usually 12-72 h after transfection, depending on the reporter used, using fluorescence microscopy, FAC sorting (EGFP) or by colorimetric detection with X-Gal in fixed cells (bGal). The average transfection efficiency was about 40% for Cos7 cells and about 30% for PC12 cells. The amount of DNA of the reporter plasmids G5-bGal, G5-EGFP, G5C-EGFP, CMV-STOP/EGFP and CMV-STOP/bGal was always 1 µg per reaction mixture, with the amounts of the Cre recombinase reporters, G5-Cre and G5C-Cre being varied. The functionality of the reporters was tested via cotransfection with the expression plasmid of the complete transcription activator GV (1 µg per reaction mixture). The results were comparable between PC12 and Cos7 cells, with a slightly stronger background but overall higher signal intensity in Cos7 cells compared to PC12 cells.

The Cre-based reporter system used herein is based on the Gal4-dependent transcriptional activation of a Cre reporter plasmid. The expressed Cre protein can then catalyze the excision of a transcriptional STOP cassette flanked by Cre recognition and recombination sequences (loxP sites) in the same orientation. The activated reporter gene is now under the control of the constitutive human CMV promoter which is very strong in most cell lines, resulting in an enormous increase in the signal.

After cotransfection of GV with the G5-bGal reporter, X-Gal staining was detected in a multiplicity of cells after only 12 h. After cotransfection of GV with the G5-EGFP reporter, GFP fluorescence was detected only in Cos7 cells in a small number of cells after 72 h. Transfections of the G5-bGal and G5-EGFP reporters exhibited no background activity. After cotransfection of the G5C-EGFP reporter plasmid with GV, a markedly higher number of GFP-positive cells, compared to the control transfection without GV, was detected after only 48 h. Some GFP-positive cells, however, were also detected in the control transfection. Transfection of GV together with CMV-STOP/EGFP or CMV-STOP/bGal exhibited no background. Cotransfection of in each case 1 µg of G5-Cre and CMV-STOP/EGFP showed a very high number of GFP-positive cells after 48 h. The first GFP signals were detected after only 12 h. The best ratio of GV-induced signal to background was obtained by transfection of 50 ng of G5-Cre with in each case 1 µg of CMV-STOP/EGFP or CMV-STOP/bGal and GV. The increased basal promoter activity of the G5C-Cre construct made it impossible to reduce the background by reducing the amounts used, as for G5-Cre.

The evaluation of the transient transfections for analyzing the components of the Cre-based reporter system showed the following:

1) The reporter system is characterized by a very high sensitivity. 2) Due to said high sensitivity, it is not possible to completely remove the background of components of the system in transient transfections. 3) Using the Cre recombinase, it is possible to use EGFP as downstream Cre reporter with a sensitivity and kinetics comparable to bGal. 4) When using a relatively strong basal minimal promoter (CMVmin), EGFP is also less sensitive as reporter than bGal.

Example 3

Application of the Cre-Recombinase-Based Reporter System After Transient Transfection into PC12 and Cos7 Cells as Two-Hybrid System for Analyzing Constitutive Protein Interactions The application of the Cre recombinase-based reporter system in the two-hybrid system in mammalian cells was tested via analysis of known interaction partners (see FIG. 2, flowchart of the Cre recombinase-dependent two-hybrid system). Most basic helix-loop-helix (bHLH) proteins form heterodimeric complexes. The interaction is mediated via two amphipathic helices which form a characteristic four-helix bundle (Ma, Rould et al. 1994) (Baxevanis and Vinson 1993). The interaction between the bHLH proteins ME2 and Nex and, respectively, NeuroD served as a test system. For this purpose, the bHLH domain of ME2 was amplified by PCR and expressed as fusion protein with Gal4-DBD (G-ME2bHLH). Full length NEX and NeuroD were expressed as fusion proteins with VP16 TAD (V-ND and V-Nex, respectively).

Another known motif which mediates specific protein-protein interactions is the leucine zipper motif in coiled-coil (cc) domains (Lupas 1996). Another test system used were parts of the intracellular sections of GBR1 and GBR2 which in each case contain a cc domain via which they form heterodimers (Kuner, Kohr et al. 1999). GBR1cc (L859-K960) and GBR2cc (I744-G849) were amplified and cloned by means of PCR using specific oligonucleotides. GBR1cc was fused to the C terminus of VP16 (V-GBR1cc), and GBR2cc was fused to the C terminus of Gal4 (G-GBR2cc). Deletion mutants of said protein domains, GBR1 (L859-K960 ΔS887-L921) and GBR2 (I744-G849ΔS785-Q816) (V-GBR1ccDel and G-GBR2ccDel) were used as negative control, and these mutations had previously been shown, by immunoprecipitation and by means of yeast two-hybrid technique, not to interact.

An interaction was detected both for the interaction partners G-ME2bHLH and V-NEX and, respectively, V-ND and for G-GBR2cc and V-GBR1cc in PC12 and Cos7 cells, using the Cre reporter system and GFP fluorescence as measure. The controls, individual transfections and the coiled-coil deletion constructs (V-GBR1ccDel and G-GBR2ccDel), showed no or substantially weaker signals. The following relative strength of interactions was obtained from the experiments: GBR2cc/V-GBR1cc>>G-ME2bHLH/V-ND>>G-ME2bHLH/V-NEX. The results were confirmed using bGal as two-hybrid reporter.

Example 4

Preparation of Stable PC12 and Cos7 Cell Lines Containing the Components of the Cre Reporter System The results from the experiments of the Cre recombinase-based two-hybrid system after transient transfection in mammalian cells indicated that 1) the sensitivity of the system was comparable to a beta-galactosidase reporter, even when using an EGFP downstream of Cre, and 2) owing to the increased sensitivity and to the switch mechanism of the Cre activity, it was not possible to completely reduce the background. In order to be able to control the background of the system, first a component of the tetracyclin-dependent gene regulation system, which enables expression of the interaction partners to be finally regulated, was stably incorporated into PC12 and Cos7 cells (Gossen, Freundlieb et al. 1995). For this purpose, a DNA fragment coding for the tet-dependent transactivator (tTA) under the control of the CMV promoter was cotransfected with a linearized DNA element, neoR, which confers resistance to the aminoglycoside G418. G418 selection (400 μg/ml) was started three days after transfection, and after 3-4 weeks cell clones were identified and isolated. The latter were analyzed independently for functional tTA expression via cotransfection with a tTA-dependent reporter (tetO-EGFP). In each case one PC12 cell clone and one Cos7 cell clone with tetracycline-dependent regulation of the GFP reporter were used for the further steps.

In the next step, the G5-Cre or G5C-Cre DNA fragments were cotransfected with a fragment conferring resistance to HygromycinB. Four weeks after HygromycinB selection (60 μg/ml), cell clones were isolated and analyzed for GV-dependent Cre activity. For this purpose, the Cos7 and PC12 cell clones were in each case transfected with CMV-STOP/EGFP and cotransfected with CMV-STOP/EGFP and GV and analyzed for GV/Cre-dependent induction of GFP fluorescence. All of the Cos7 and most of the PC12 cell clones which showed an increase in Cre activity due to GV likewise exhibited a certain Cre background activity. PC12 cell clone #20 showed absolutely no constitutive Cre expression, i.e. no GFP-positive cell was detectable after transfection with CMV-STOP/EGFP (see FIG. 3, bottom left). After cotransfection of CMV-STOP/EGFP and GV on the other hand, a multiplicity of GFP-positive cells were detected (see FIG. 3, top left).

PC12 cells are an established cultured cell line of a rat pheochromocytoma and thus originate from sympathoadrenergic tissue of the adrenal medulla (Greene and Tischler 1976). These cells can be stimulated with nerve growth factor (NGF) and differentiate in an NGF-dependent manner to a neuron-related cell type which is postmitotic and forms neuronal processes. In order to test the Cre-based reporter system under these postmitotic conditions, GV-transfected PC12 cells of the line #20 were stimulated with NGF (2.5 S NGF, 5 ng/ml, Promega) immediately after transfection and analyzed three days after GV-induced GFP-fluorescence (see FIG. 4). The efficiency of the Cre reporter system (lower magnification, FIG. 4 top) was not influenced by NGF-induced differentiation (lower magnification, FIG. 4 top). The neuronal morphology of the cells was not impaired by the Cre reporter system (lower magnification, FIG. 4 top). In summary, these results demonstrate that the Cre reporter system functions in stable PC12 cell clones in a background-free manner, even under postmitotic conditions.

In order to stably express all necessary components of the Cre-based reporter system, PC12 cells of the line #20 were cotransfected with the linearized plasmid constructs CMV-STOP/EGFP (STOP=neoR) and CMV-STOP/BlasR (STOP=TKZeoR) and selected with zeocin (500 μg/ml, Invitrogen). GFP-negative and blasticidinS-sensitive cell clones were analyzed via transfection with GV. GFP-positive cells of the cell clone #20.4 were detected two days after GV transfection (see FIG. 5). Three to four weeks after GV transfection and blasticidinS selection (2 μg/ml, Calbiochem), resistant cell clones were identified, and all cells of these clones were GFP-positive (see FIG. 6). In summary, these experiments demonstrate that the cell clone 20.4 has stably integrated and functionally expressed all components of the Cre-based reporter system.

Example 5

Application of the Two-Hybrid System in the PC12 Cell Line 20.4 for Analyzing Constitutive Protein Interactions As described in example 4, the PC12 cell line 20.4 expresses all components of the Cre-based reporter system in a completely functional manner. In order to test whether the cell line 20.4 can be utilized for application in the two-hybrid system (see FIG. 2), the known interaction partners described in example 3 were analyzed. Two days after cotransfection of the interaction partners G-ME2bHLH and V-ND, no GFP-positive cells were detectable (see FIG. 7, bottom left). After single transfections of G-ME2bHLH and V-ND, GFP-positive cells were likewise not detectable (see FIG. 7, central figures, left). The control, after transfection with GV, showed the expected high number of GFP-positive cells (see FIG. 7, top left). This result, together with the observation of complete absence of constitutive background with respect to uninduced Cre expression, suggested that at least the Gal4-dependent Cre reporter had been integrated into a region of the heterochromatin and was thus accessible only by very strong transactivators such as GV. Therefore, the same two-hybrid analysis was carried out in the following experiments, after transient addition of trichostatin A (3 µM, for 12 h, Sigma) (FIG. 8). TSA acts as an inhibitor of deacetylases, and inhibition of deacetylation results in an overall less densely packed, transcriptionally inactive heterochromatin sections. After transient addition of TSA into the culturing medium of PC12 20.4 cells, a multiplicity of GFP-positive cells were now detected, two days after transfection of the interaction partners G-ME2bHLH and V-ND (see FIG. 8, bottom left). After single transfections of G-ME2bHLH and V-ND, no GFP-positive cells were detectable (see FIG. 8, central figures, left). The control, after transfection with GV, showed the expected high number of GFP-positive cells (see FIG. 8, top left). The relatively high concentration of 3 µM TSA for a period of 12 h, however, also resulted in a lower number of surviving cells (cf. FIG. 7 and FIG. 8, right-hand column). The TSA concentration with the best ratio of cell survival and nearly background-free detection of the interaction of G-ME2bHLH and V-ND, was 300 µM for 12 h. For the slightly stronger interaction of GBR2cc and V-GBR1cc (see example 3), the experiments were carried out with TSA concentrations of 200 µM TSA for 12 h (see FIG. 9). Only after cotransfection of the interaction partners GBR2cc and V-GBR1cc, a multiplicity of GFP-positive cells were detected, after single transfection and cotransfection of the cc deletion mutants, GBR2ccDel and V-GBR1ccDel, no GFP-positive cells were microscopically detectable (see FIG. 9, bottom bar). Analysis by Fluorescent Activated Cell Sorting (FACS) confirmed these results (see FIG. 10).

In summary, these results demonstrate that it is possible to carry out a two-hybrid analysis in the PC12 cells of the line 20.4 and to control the sensitivity and, respectively, the background by addition of TSA.

Example 6

Application of the Cre Recombinase-Based Reporter System as Two-Hybrid System for Analyzing Induced and Transient Interactions This example describes utilization of the Cre recombinase-based reporter system in the two-hybrid approach of detecting a stimulus-induced and transient interaction in vivo. As FIG. 11 diagrammatically shows, transient activation of the Cre reporter is sufficient in order to ensure, via the function of the Cre recombinase located in the nucleus, permanent activation of downstream reporter.

A well-characterized example of an induced protein-protein interaction is the phosphorylation-dependent binding of the transcription activators CREB to the transcription coactivator CBP (CREB Binding Protein) (Chrivia, Kwok et al. 1993). For example, protein kinase A (PKA)-mediated phosphorylation of CREB at Ser133, in the "kinase-inducible-domain (KID)", results in specific binding to the "KIX" domain of CBP. PKA may be stimulated by adding the adenylate cyclase-stimulating substance forskolin, leading to a transient increase in the intracellular cAMP level and thus to PKA activation. After removing PKA stimulation by removing the forskolin from the culture medium of cells, CREB-Ser133 is rapidly dephosphorylated via active phosphatases endogenous to the cell. For analysis in the two-hybrid system in the PC12 20.4 cells, CREB was fused C-terminally to Gal4 DBD (G-CREB), and the CBP-KIX domain was fused to the C terminus of VP16 TAD (V-CBP-KIX).

Three days after transfection of PC12 20.4 cells with G-CREB and V-CBP-KIX and corresponding controls, detection of the interaction was analyzed by FACS. Without forskolin stimulation, neither single nor cotransfection of the constructs resulted in significant activation of the Cre/EGFP reporter system (see FIG. 12, top and bottom graph, framed bars). After transient forskolin stimulation immediately after transfection (4 µM for 12 h) and FACS analysis after 3 days, a distinct increase in the total number of GFP-positive cells and in the cumulated total fluorescence after cotransfection of G-CREB and V-CBP-KIX were observed (see FIG. 12, black bar, right). A by far smaller but likewise significant increase in the number of GFP-positive cells and total fluorescence was measured in a forskolin-dependent manner for single transfection with G-CREB. This can be explained by the likewise stimulated interaction of G-CREB with the endogenous CBP or related transcriptional cofactors. The stronger relative increase in total fluorescence with and without stimulation, in comparison with the somewhat smaller relative increase in GFP-positive cells indicates a kinetic component in the system.

In summary, these results demonstrate that it is also possible to carry out two-hybrid analyses in the PC12 20.4 cells, with interactions which are stimulus-dependent and transient. How transient said interaction is, was shown by Chawla and Bading. Their analyses of CREB phosphorylation after short-time calcium signals revealed that S133 phosphorylation results in rapid activation of CREB, but the protein is inactive again due to dephosphorylation only after a few minutes (Chawla and Bading, 2001) (dephosphorylation of S133 results in dissociation of CREB and CBP-KIX).

Example 7

Proteolytic Activation of a Membrane-Anchored Transcription Activator After Transient Cotransfection and, Connected therewith, Activation of the Reporter System in PC12 20.4

Membrane anchoring of the Gal4/VP16 fusion protein in PC12 20.4 and activation of the reporter system after proteolytic removal.

In this example, the feasibility in principle of the protease switch on the membrane in PC12 20.4 cells is described. It was the aim to establish a further intracellular mechanism which transduces proteolytic events at the periphery into permanent signals. For this purpose, the Gal4/VP16 fusion protein required for recombinase activation was anchored on the membrane (TM-GV) and was then intended to activate via a specific proteolytic cleavage the reporter system in the nucleus. Stable localization of Gal4/VP16 on the cell membrane was achieved by fusion to the transmembrane domain of the PDGF (platelet derived growth factor) receptor, with insertion and correct orientation of the construct in the membrane being ensured by an N-terminal signal sequence. The efficacy of activation was analyzed via expression of the EGFP reporter. For this purpose, the transfected cells were trypsinated after 48 h and the proportion of positive cells was quantitatively determined in an FAC analyzer (FACSCalibur from BD Bioscience). For this experiment, in each case $1.5 \times 10^5$ PC12 20.4 cells were plated on a 24-well plate and transfected with in each case 0.5 µg of the corresponding plasmid DNA on the next day (Lipofectamine2000; Invitrogen). Transient expression of the chimeric membrane protein in PC12 20.4 cells resulted in no significant activation of the reporter system (FIG. 15), demonstrating that the GV transcription activator is stably anchored on the membrane. To proteolytically remove the GV transactivator, the bases coding for the 7 amino acid recognition sequence (ENLYFQG) (SEQ ID NO: 1) of the tobacco etch virus (TEV) Nla protease (TEV protease) were inserted into the DNA sequence between PDGF transmembrane segment and Gal4/VP16. Introduction of this or alternative protease cleavage sites did not result in any unspecific release of the Gal4/VP16 fusion protein. Coexpression of the TEV protease, however, led to efficient cleavage of the TM/tev/GV construct and subsequently to distinct activation of the Cre/EGFP reporter system. In another step, it was intended to demonstrate that the TEV protease is active even after membrane anchoring. The latter is a basic requirement for the interaction analysis of membrane proteins. For this purpose, the TEV protease was, analogously to the Gal4/VP16 reporter, N-terminally fused to the transmembrane domain of the PDGF receptor and coexpressed with the TM/tevS/GV construct in PC12 20.4 cells. The result showed no significant difference in the activation of the Cre/EGFP reporter system by soluble and membrane-bound protease. This example underlines the suitability in principle of the method of detecting protein interactions outside the nucleus, in particular on the cell membrane. A precondition for this is the functional coupling of an interaction to the proteolytic cleavage, and this may be carried out by transcomplementation of a protease or, in the case of a low concentration of the partners involved, also by producing a suitable proximity between protease and cleavage site (FIG. 15).

Analogously to the Gal4/VP16 transcription activator construct, the Cre reporter was anchored directly on the cell membrane, with the proteolytic release thereof then leading directly to EGFP activation in the nucleus. In the case of weak interactions of very rare proteins, it is possible that the double strategy described is not sensitive enough in order to transduce an interaction on the membrane into a signal. A substantially higher sensitivity is achieved, if, instead of the Gal4/VP16 activator used before, the Cre recombinase is coupled directly to the membrane by means of a PDGF transmembrane domain and linked by a protease recognition site. Overexpression of the TM-Cre construct initially resulted in increased background activity and had to be compensated for by weaker expression. For this purpose, the TM-Cre construct was stably transfected into PC12 cells and selected for background-free clones. These cell lines, cotransfected with TEV protease and STOP-EGFP reporter plasmid, subsequently turned rapidly and distinctly green.

Example 8

Transcomplementation of TEV Protease

Transcomplementation of the TEV protease provides a possibility of converting a protein interaction into the proteolytic removal of a membrane-bound transcription activator. The N1a protease of tobacco etch virus is a member of the family of C4 cysteine peptidases which are structurally homologous to the trypsin-like serine proteases. They have therefore likewise a bilobal β-barrel structure in which three amino acids are characteristically arranged. Modeling of the TEV protease sequence to a known 3D structure of a related protease (Dengue virus NS3 protease PDB 1bef) with the aid of the Swissmodel Software suggests that these amino acids, the "triads", are spread over the two lobes of the structure and are located opposite each other. Although the two lobes are physically connected with one another, they seem to fold independently of one another, however. The starting point for transcomplementation was the aim to separate the amino acids of the triads in such a way that they are located on different fragments which could per se form a tertiary structure but which exhibit no activity. The DNA for the N- and C-terminal fragments of the TEV protease was amplified by means of specific PCR oligonucleotides, introducing 5' an NheI and a 3' KpnI restriction cleavage site, and cloned in a plasmid via NheI and KpnI to the 3' termini of the "coiled coil" domains of GBR1 and GBR2, which are anchored via the PDGF transmembrane domain (see examples 3 and 5). These constructs were designed in such a way that the interaction of the membrane-anchored "coiled-coil" regions recombine the N- and C-terminal fragments of the TEV protease to an active form, and this may be detected via removal of the likewise membrane-anchored Gal4/VP16 transactivator in PC12 20.4 cells. In order to ensure that none of the two generated TEV "subunits" has proteolytic activity, they were independently transfected and tested. It was also checked, by cloning the particular GBR deletion mutants (see example 5), that the C- and N-terminal lobes do not gain activity after cotransfection. The experiment revealed that several regions in the TEV protease are suitable for transcomplementation, in particular the region between amino acid 60 and 80 and, in particular, the region between 95 and 120. Dividing the protease at these sites led to two inactive fragments, and coexpression of these variants fused to interaction domains in many cases reconstituted the proteolytic activity, with some examples being described in more detail below. The two TEV fragments Gly1-Thr70 and Thr71-Gly243 gained more than 30% of the activity of the intact protease when fused to the membrane-anchored, interacting "coiled coil" domains of GBR1 and GBR2 (FIG. 18). Neither individual expression nor coexpression of the fragments fused to the noninteracting mutants of the GBR domains, resulted in comparably strong activation of the reporter system (FIG. 18a). A combination of the partially overlapping fragments Gly1-Thr70 and His61-Gly243 exhibited a similarly good activation. Parts of a protein intended to result in a functional complete protein by transcomplementation may therefore also partly overlap. Several fragments which gain activity after interaction were found in the region of position 100 (the predicted linker domain of N-terminal and C-terminal lobe). The combination of fragments Gly1-T118 and K119-Gly243, in particular, distinguished itself by very high activity after transcomplementation (FIG. 18b).

REFERENCES

Ashman, K., M. F. Moran, et al. (2001). "Cell signalling—the proteomics of it all." Sci STKE 2001(103): E33.

Baron, U., S. Freundlieb, et al. (1995). "Co-regulation of two gene activities by tetracycline via a bidirectional promoter." Nucleic Acids Res 23(17): 3605-6.

Barrett-A J, Rawlings-N D, et al. (1998). Handbook of Proteolytic Enzymes, Academic Press.

Baxevanis, A. D. and C. R. Vinson (1993). "Interactions of coiled coils in transcription factors: where is the specificity?" Curr Opin Genet Dev 3(2): 278-85.

Bazan, J. F. and R. J. Fletterick (1988). "Viral cysteine proteases are homologous to the trypsin-like family of serine proteases: structural and functional implications." Proc Natl Acad Sci USA 85(21): 7872-6.

Bazan, J. F. and R. J. Fletterick (1989). "Comparative analysis of viral cysteine protease structural models." FEBS Lett 249(1): 5-7.

Brizuela, L., P. Braun, et al. (2001). "FLEXGene repository: from sequenced genomes to gene repositories for high-throughput functional biology and proteomics." Mol Biochem Parasitol 118(2): 155-65.

Broad, e. a. (1999). Protease Based Gene Switching System. PCT WO 99/11801 A2, Zeneca Ltd, GB.

Buchholz, F., P. O. Angrand, et al. (1998). "Improved properties of FLP recombinase evolved by cycling mutagenesis." Nat Biotechnol 16(7): 657-62.

Chawla, S. and Bading, H. (2001). "CREB/CBP and SRE-interacting transcriptional regulators are fast on-off switches: duration of calcium transients specifies the magnitude of transcriptional responses." J. Neurochem November 2001; 79(4):849-58

Chrivia, J. C., R. P. Kwok, et al. (1993). "Phosphorylated CREB binds specifically to the nuclear protein CBP." Nature 365(6449): 855-9.

Ehrhard, K. N., J. J. Jacoby, et al. (2000). "Use of G-protein fusions to monitor integral membrane protein-protein interactions in yeast." Nat Biotechnol 18(10): 1075-9.

Esposito, D. and J. J. Scocca (1997). "The integrase family of tyrosine recombinases: evolution of a conserved active site domain." Nucleic Acids Res 25(18): 3605-14.

Eyckerman, S., A. Verhee, et al. (2001). "Design and application of a cytokine-receptor-based interaction trap." Nat Cell Biol 3(12): 1114-9.

Faber, K. N., A. M. Kram, et al. (2001). "A novel method to determine the topology of peroxisomal membrane proteins in vivo using the tobacco etch virus protease." J Biol Chem 276(39): 36501-7.

Fearon, E. R., T. Finkel, et al. (1992). "Karyoplasmic interaction selection strategy: a general strategy to detect protein-protein interactions in mammalian cells." Proc Natl Acad Sci USA 89(17): 7958-62.

Feil, R., J. Brocard, et al. (1996). "Ligand-activated site-specific recombination in mice." Proc Natl Acad Sci USA 93(20): 10887-90.

Fields, S. and O. Song (1989). "A novel genetic system to detect protein-protein interactions." Nature 340(6230): 245-6.

Gavin, A. C., M. Bosche, et al. (2002). "Functional organization of the yeast proteome by systematic analysis of protein complexes." Nature 415(6868): 141-7.

Gossen, M., S. Freundlieb, et al. (1995). "Transcriptional activation by tetracyclines in mammalian cells." Science 268(5218): 1766-9.

Greene, L. A. and A. S. Tischler (1976). "Establishment of a noradrenergic clonal line of rat adrenal pheochromocytoma cells which respond to nerve growth factor." Proc Natl Acad Sci USA 73(7): 2424-8.

Guo, F., D. N. Gopaul, et al. (1997). "Structure of Cre recombinase complexed with DNA in a site-specific recombination synapse." Nature 389(6646): 40-6.

Haj, F. G., P. J. Verveer, et al. (2002). "Imaging Sites of Receptor Dephosphorylation by PTP1B on the Surface of the Endoplasmic Reticulum." Science 295(5560): 1708-11.

Hazzalin, C. A. and L. C. Mahadevan (2002). "MAPK-regulated transcription: a continuously variable gene switch?" Nat Rev Mol Cell Biol 3(1): 30-40.

Hirowatari, Y., M. Hijikata, et al. (1995). "A novel method for analysis of viral proteinase activity encoded by hepatitis C virus in cultured cells." Anal Biochem 225(1): 113-20.

Hubsman, M., G. Yudkovsky, et al. (2001). "A novel approach for the identification of protein-protein interaction with integral membrane proteins." Nucleic Acids Res 29(4): E18.

Hunter, T. (2000). "Signaling—2000 and beyond." Cell 100 (1): 113-27.

Husi, H., M. A. Ward, et al. (2000). "Proteomic analysis of NMDA receptor-adhesion protein signaling complexes." Nat Neurosci 3(7): 661-9.

Huttner, W. B. and A. Schmidt (2000). "Lipids, lipid modification and lipid-protein interaction in membrane budding and fission—insights from the roles of endophilin A1 and synaptophysin in synaptic vesicle endocytosis." Curr Opin Neurobiol 10(5): 543-51.

Johnsson, N. and A. Varshavsky (1994). "Split ubiquitin as a sensor of protein interactions in vivo." Proc Natl Acad Sci USA 91(22): 10340-4.

Kamada, S., H. Kusano, et al. (1998). "A cloning method for caspases substrates that uses the yeast two-hybrid system: cloning of the antiapoptotic gene gelsolin." Proc Natl Acad Sci USA 95(15): 8532-7.

Karimova, G., J. Pidoux, et al. (1998). "A bacterial two-hybrid system based on a reconstituted signal transduction pathway." Proc Natl Acad Sci USA 95(10): 5752-6.

Kellendonk, C., F. Tronche, et al. (1996). "Regulation of Cre recombinase activity by the synthetic steroid RU 486." Nucleic Acids Res 24(8): 1404-11.

Kozak, M. (1987). "An analysis of 5'-noncoding sequences from 699 vertebrate messenger RNAs." Nucleic Acids Res 15(20): 8125-48.

Kozak, M. (1989). "The scanning model for translation: an update." J Cell Biol 108(2): 229-41.

Kuner, R., G. Kohr, et al. (1999). "Role of heteromer formation in GABAB receptor function." Science 283(5398): 74-7.

Lewandoski, M. (2001). "Conditional control of gene expression in the mouse." Nat Rev Genet 2(10): 743-55.

Luban, J. and S. P. Goff (1995). "The yeast two-hybrid system for studying protein-protein interactions." Curr Opin Biotechnol 6(1): 59-64.

Lupas, A. (1996). "Coiled coils: new structures and new functions." Trends Biochem Sci 21(10): 375-82.

Ma, P. C., M. A. Rould, et al. (1994). "Crystal structure of MyoD bHLH domain-DNA complex: perspectives on DNA recognition and implications for transcriptional activation." Cell 77(3): 451-9.

Maroun, M. and A. Aronheim (1999). "A novel in vivo assay for the analysis of protein-protein interaction." Nucleic Acids Res 27(13): e4.

Marshall, C. J. (1995). "Specificity of receptor tyrosine kinase signaling: transient versus sustained extracellular signal-regulated kinase activation." Cell 80(2): 179-85.

Mattheakis, L. C., S. E. Olivan, et al. (1999). "Expression of cre recombinase as a reporter of signal transduction in mammalian cells." Chem Biol 6(11): 835-44.

Metzger, D., J. Clifford, et al. (1995). "Conditional site-specific recombination in mammalian cells using a ligand-dependent chimeric Cre recombinase." Proc Natl Acad Sci USA 92(15): 6991-5.

Michnick, S. W. and A. Galarneau (2001). A Protein FragmentComplementation Assay (PCA) for the Detection of ProteinProtein Interactions Based on the *E.coli* TEM-1-Beta-Lactamase. PCT WO 01/94617 A2.

Michnick, S. W. and I. Remy (2001). Protein Fragment Complementation Assays for the Detection of Biological or Drug Interactions. U.S. Pat. No. 6,294,330. USA, Odyssey Pharmaceuticals Inc.

Migaud, M., P. Charlesworth, et al. (1998). "Enhanced long-term potentiation and impaired learning in mice with mutant postsynaptic density-95 protein." Nature 396(6710): 433-9.

Mohler, W. A. and H. M. Blau (1996). "Gene expression and cell fusion analyzed by lacZ complementation in mammalian cells." Proc Natl Acad Sci USA 93(22): 12423-7.

Nunes-Duby, S. E., H. J. Kwon, et al. (1998). "Similarities and differences among 105 members of the Int family of site-specific recombinases." Nucleic Acids Res 26(2): 391-406.

Pawson, T. and J. D. Scott (1997). "Signaling through scaffold, anchoring, and adaptor proteins." Science 278(5346): 2075-80.

Pelletier, J. N., F. X. Campbell-Valois, et al. (1998). "Oligomerization domain-directed reassembly of active dihydrofolate reductase from rationally designed fragments." Proc Natl Acad Sci USA 95(21): 12141-6.

Pestova, T. V., V. G. Kolupaeva, et al. (2001). "Molecular mechanisms of translation initiation in eukaryotes." Proc Natl Acad Sci USA 98(13): 7029-36.

Prochiantz, A. (2000). "Messenger proteins: homeoproteins, TAT and others." Curr Opin Cell Biol 12(4): 400-6.

Rigaut, G., A. Shevchenko, et al. (1999). "A generic protein purification method for protein complex characterization and proteome exploration." Nat Biotechnol 17(10): 1030-2.

Rojo-Niersbach, E., D. Morley, et al. (2000). "A new method for the selection of protein interactions in mammalian cells." Biochem J 348(Pt 3): 585-90.

Rossi, F., C. A. Charlton, et al. (1997). "Monitoring protein-protein interactions in intact eukaryotic cells by beta-galactosidase complementation." Proc Natl Acad Sci USA 94(16): 8405-10.

Ryan, M. D. and M. Flint (1997). "Virus-encoded proteinases of the picornavirus super-group." J Gen Virol 78(Pt 4): 699-723.

Sambrook-J and Russell-D W (2001). Cold Spring Harbor, N.Y., CSHL Press.

Sauer, B. (1990). Site Specific Recombination of DNA in Eucaryotic Cells. U.S. Pat. No. 4,959,317. USA, Du Pont.

Sauer, B. (1998). "Inducible gene targeting in mice using the Cre/lox system." Methods 14(4): 381-92.

Shaikh, A. C. and P. D. Sadowski (2000). "Trans complementation of variant Cre proteins for defects in cleavage and synapsis." J Biol Chem 275(39): 30186-95.

Shioda, T., S. Andriole, et al. (2000). "A green fluorescent protein-reporter mammalian two-hybrid system with extrachromosomal maintenance of a prey expression plasmid: application to interaction screening." Proc Natl Acad Sci USA 97(10): 5220-4.

Siegel, R. M., F. K. Chan, et al. (2000). "Measurement of molecular interactions in living cells by fluorescence resonance energy transfer between variants of the green fluorescent protein." Sci STKE 2000(38): L1.

Simons, K. and E. Ikonen (1997). "Functional rafts in cell membranes." Nature 387(6633): 569-72.

Simpson, J. C., R. Wellenreuther, et al. (2000). "Systematic subcellular localization of novel proteins identified by large-scale cDNA sequencing." EMBO Rep 1(3): 287-92.

Uhlmann, F., D. Wernic, et al. (2000). "Cleavage of cohesin by the CD clan protease separin triggers anaphase in yeast." Cell 103(3): 375-86.

Ullmann, A., D. Perrin, et al. (1965). "[Identification, by in vitro complementation and purification, of a peptide fraction of Escherichia coli beta-galactosidase]." J Mol Biol 12(3): 918-23.

Vagner, S., B. Galy, et al. (2001). "Irresistible IRES. Attracting the translation machinery to internal ribosome entry sites." EMBO Rep 2(10): 893-8.

Xu, Y., D. W. Piston, et al. (1999). "A bioluminescence resonance energy transfer (BRET) system: application to interacting circadian clock proteins." Proc Natl Acad Sci USA 96(1): 151-6.

Yasukawa, H., A. Sasaki, et al. (2000). "Negative regulation of cytokine signaling pathways." Annu Rev Immunol 18:143-64.

Ziauddin, J. and D. M. Sabatini (2001). "Microarrays of cells expressing defined cDNAs." Nature 411(6833): 107-10.

---

The invention claimed is:

1. A method of detecting and analyzing protein interactions, which comprises the steps:
   a) expressing in an isolated host cell:
      a1) a first fusion protein comprising a first interaction partner and a functional protease and
      a2) a second fusion protein comprising a second interaction partner, a functional transcription factor domain, and a further domain causing anchoring outside the nucleus, with at least the functional transcription factor domain being proteolytically removable, from the domain which causes the second fusion protein to be anchored outside the nucleus, via a recognition and cleavage site of the functional protease, and
   b) interaction of the first and second interaction partners resulting in cleavage of the functional transcription factor domain from the second fusion protein,
   c) transport of the functional transcription factor domain into the nucleus resulting in activation of a reporter system, and
   d) detecting a signal generated by the reporter system
      wherein, detecting a signal generated by the reporter system in the presence of the first fusion protein, but not in the absence of the first fusion protein, is a means for detecting and analyzing protein interactions.

2. The method as claimed in claim 1, wherein the reporter protein is selected from the group consisting of fluorescent proteins, luciferases, beta-galactosidase, alkaline phosphatase, beta-lactamase, proteins and enzymes conferring resistance to cytotoxic substances or minimal media, cytotoxic or pro-apoptotic proteins, and proteins altering the growth or morphology of cells.

3. The method as claimed in claim 1, wherein the functional transcription factor domain is anchored in such way that it is located on the cytoplasmic side of membranes or cell compartments in order to be able to enter the nucleus after proteolytic removal from the anchoring position.

4. A method of detecting and analyzing protein interactions, which comprises the steps:
   a) expressing in an isolated host cell:
      a1) a first fusion protein comprising a first interaction partner and a functional protease and
      a2) a second fusion protein comprising a second interaction partner and a functional transcription factor domain, wherein the fusion protein is linked to the C terminus of a type I or type III membrane protein or the C terminus of a transmembrane region of such membrane protein, with at least the functional transcription factor domain being proteolytically removable, from said C terminus via a recognition and cleavage site of the functional protease, and
   b) interaction of the first and second interaction partners resulting in cleavage of the functional transcription factor domain from the second fusion protein,
   c) transport of the functional transcription factor domain into the nucleus resulting in activation of a reporter system, and
   d) detecting a signal generated by the reporter system
      wherein, detecting a signal generated by the reporter system in the presence of the first fusion protein, but not in the absence of the first fusion protein, is a means for detecting and analyzing protein interactions.

5. A method of detecting and analyzing protein interactions, which comprises the steps:
   a) expressing in an isolated host cell:
      a1) a first fusion protein comprising a first interaction partner and a functional protease and
      a2) a second fusion protein comprising a second interaction partner and a functional transcription factor domain, wherein the fusion protein is linked to the N terminus of a type II membrane protein or the N terminus of a transmembrane region of such membrane protein, with at least the functional transcription factor domain being proteolytically removable, from said N terminus via a recognition and cleavage site of the functional protease, and
   b) interaction of the first and second interaction partners resulting in cleavage of the functional transcription factor domain from the second fusion protein,
   c) transport of the functional transcription factor domain into the nucleus resulting in activation of a reporter system, and
   d) detecting a signal generated by the reporter system
      wherein, detecting a signal generated by the reporter system in the presence of the first fusion protein, but not in the absence of the first fusion protein, is a means for detecting and analyzing protein interactions.

6. The method as claimed in claim 3, wherein the reporter protein is selected from the group consisting of fluorescent proteins, luciferases, beta-galactosidase, alkaline phosphatase, beta-lactamase, proteins and enzymes conferring resistance to cytotoxic substances or minimal media, cytotoxic or pro-apoptotic proteins, and proteins altering the growth or morphology of cells.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Glu Asn Leu Tyr Phe Gln Gly
1               5
```